United States Patent [19]

Kurimoto et al.

[11] Patent Number: 5,238,598
[45] Date of Patent: Aug. 24, 1993

[54] OPTICALLY ACTIVE AROMATIC COMPOUNDS, PREPARATION PROCESS THEREOF, AND LIQUID CRYSTAL COMPOSITIONS AND ELEMENTS

[75] Inventors: Isao Kurimoto, Toyonaka; Takayuki Higashii, Takatsuki; Shoji Toda, Ibaraki; Masayoshi Minai, Moriyama; Chizu Sekine; Takeshi Tani, both of Tsukuba; Koichi Fujisawa, Tsukuba, all of Japan

[73] Assignee: Sumitomo Chemical Company, Limited, Osaka, Japan

[21] Appl. No.: 626,980

[22] Filed: Dec. 13, 1990

[30] Foreign Application Priority Data

Dec. 18, 1989 [JP] Japan ................... 1-329085
Aug. 29, 1990 [JP] Japan ................... 2-231539

[51] Int. Cl.$^5$ ............ C09K 19/06; C09K 19/00; C07C 69/76; C07C 39/00
[52] U.S. Cl. ............ 252/299.6; 252/299.61; 252/299.66; 252/299.65; 252/299.67; 544/298; 568/647; 568/661; 568/716; 560/102
[58] Field of Search ......... 252/299.61, 299.65, 252/299.66, 299.67, 299.6; 560/62, 65, 76, 102; 544/298; 568/661, 647; 570/129

[56] References Cited

U.S. PATENT DOCUMENTS

| | | | |
|---|---|---|---|
| 4,676,925 | 6/1987 | Inoue et al. | 252/299.65 |
| 4,751,019 | 6/1988 | Saito et al. | 252/299.66 |
| 4,818,432 | 4/1989 | Miyazawa et al. | 252/299.66 |
| 4,886,623 | 12/1989 | Mitsuhashi et al. | 252/299.66 |
| 4,911,863 | 3/1990 | Sage et al. | 252/299.65 |
| 4,917,817 | 4/1990 | Nohira et al. | 252/299.01 |
| 4,918,213 | 4/1990 | Nohira et al. | 558/271 |
| 4,921,632 | 5/1990 | Nakamura et al. | 252/299.1 |

FOREIGN PATENT DOCUMENTS

| | | |
|---|---|---|
| 0294852 | 12/1988 | European Pat. Off. . |
| 0301511 | 2/1989 | European Pat. Off. . |
| 0326086 | 8/1989 | European Pat. Off. . |
| 0328330 | 8/1989 | European Pat. Off. ....... 252/299.61 |
| 0357435 | 3/1990 | European Pat. Off. . |
| 8707980 | 12/1987 | World Int. Prop. O. . |

OTHER PUBLICATIONS

Streitwieser et al., *Intro. to Organic Chemistry*, 3rd ed. p. 819, (1985).
McMurry, J., *Organic Chemistry*, p. 982, (1984).
Japanese Journal of Applied Physics/Part 2: Letters, vol. 26, No. 2, Feb. 1987, pp. L77–L78, Tokyo, JP; K. Yoshino et al.: "Novel ferroelectricity in fluorinated ferroelectric liquid crystal".

*Primary Examiner*—Robert L. Stoll
*Assistant Examiner*—Cynthia Harris
*Attorney, Agent, or Firm*—Stevens, Davis, Miller & Mosher

[57] ABSTRACT

Disclosed in the present invention are the optically active aromatic compounds having a trifluoromethyl group useful as a component of ferroelectric liquid crystal compositions, a process for preparing the above compounds, liquid crystal compositions having the above compounds as an active ingredient, and liquid crystal elements using the above compositions. The optically active aromatic compounds of the Present invention represented by the formula:

$$R^1\text{-}(Y)_k\text{Ar-X-}\underset{=}{\bigcirc}\text{-}(CH_2)_n\overset{*}{C}H(CF_3)\text{-}O\text{-}(C(O))_pR^2$$

have the very excellent properties as a liquid crystal material and are useful for the preparation of liquid crystal compositions and the liquid crystal elements using such compositions.

8 Claims, No Drawings

OPTICALLY ACTIVE AROMATIC COMPOUNDS, PREPARATION PROCESS THEREOF, AND LIQUID CRYSTAL COMPOSITIONS AND ELEMENTS

BACKGROUND OF THE INVENTION

1. Field of the Invention

The present invention relates to the novel organic compounds, a process for preparing such compounds, liquid crystal compositions having said compounds as active ingredient, and liquid crystal elements using such compositions. More particularly, the invention relates to the optically active aromatic compounds having trifluoromethyl groups useful as a primary component of ferroelectric liquid crystal compositions, a process for preparing such compounds, liquid crystal compositions having said compounds as active ingredient, and liquid crystal elements using said compositions.

2. Description of the Prior Art

A TN (twisted nematic) type display system is most popular for use in the liquid crystal display elements at present. The TN liquid crystal display elements have many advantages such as low driving voltage and small power consumption.

This type of display element, however, is inferior to the luminous type display elements such as cathode-ray tube displays, electroluminenscent displays and plasma displays in response speed. A new model of TN type display element having a twisted angle set in the range of 180°-270° has been developed, but this still is inferior to the luminous type display elements in response speed. Thus, in spite of many efforts made for the improvement, there has yet been realized no TN type display element with high response speed.

However a possibility of realizing marked improvement or response speed is noted in the new display system using ferroelectric liquid crystals which are being carefully studied by many researches (Clark et al: Applied Phys. Lett., 36, 899, 1980). This system makes use of a chiral smectic C phase (hereinafter referred to as Sc* phase) which shows ferroelectricity. Sc* phase is not the only phase which shows ferroelectricity. It is known that chiral smectic F phase, G phase, H phase and I phase also exhibit ferroelectricity.

The ferroelectric liquid crystal material used for the actually utilized ferroelectric liquid crystal display elements are required to meet may property requirements. At present, there is available no single compound which can meet these requirements; it is necessary for satisfying these requirements to use a ferroelectric liquid crystal composition obtained by mixing several different liquid crystal compounds or non-liquid crystal compounds.

Beside the ferroelectric liquid crystal compositions composed of ferroelectric liquid crystal compounds alone, it is reported that a ferroelectric liquid crystal composition can be obtained by using as base material a compound or a composition assuming a non-chiral smectic phase, such as non-chiral smectic C, F, G, H or I phase (hereinafter referred to as Sc phase, etc.) and mixing therewith one or more compounds assuming a ferroelectric liquid crystal phase (Japanese Patent Application Kokai (Laid-Open) No. 195187/86). A report has also been made disclosing the obtaining of a ferroelectric liquid crystal composition by using as base material a compound or composition assuming Sc phase, etc., and mixing therewith one or more compounds which don't assume a ferroelectric liquid crystal phase (Mol. Cryst. Liq. Cryst., 89, 327, 1982).

In the light of these disclosures, it is noted that there can be composed a ferroelectric liquid crystal composition by mixing one or more optically active compounds with a base material no matter whether said compounds assume a ferroelectric liquid crystal phase or not.

However, it is desirable that the optically active substance used for forming a ferroelectric liquid crystal composition is the one which assumes a liquid crystal phase, or if it does not assume a liquid crystal phase, its structure is analogous to that of the liquid crystal compounds, that is, it is a "quasi" liquid crystal substance.

For all the efforts made so far in the art, there has not yet been found any liquid crystal material which shows spontaneous polarization required for high speed response which is low in viscosity and displays a liquid crystal phase at low temperature regions.

SUMMARY OF THE INVENTION

In view of the above, the present invention has for its object to provide a ferroelectric liquid crystal material which shows sufficient spontaneous polarization, is capable of high speed response and assumes a liquid crystal phase at lower temperature regions that with the conventional materials.

DETAILED DESCRIPTION OF THE INVENTION

The present invention provides the optically active aromatic compounds having a trifluoromethyl group represented by the general formula (1):

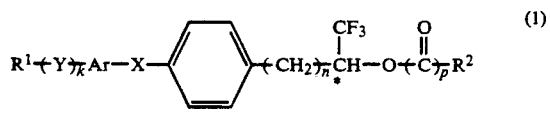

(wherein $R^1$ is an alkyl group having 3-20 carbon atoms; $R^2$ is an alkyl or alkoxyalkyl group having 1-20 carbon atoms; k is a number of 0 or 1; n is an integer of 0-5; p is a number of 0 or 1; Ar is

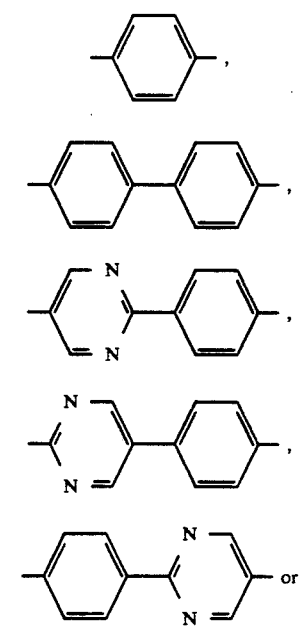

-continued

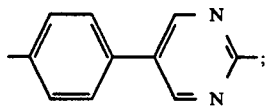

Y is —O—, —COO— or —OCO—; X is —COO— when n is 0 and —COO— or —OCO— when n is an integer of 1-5; and * mark denotes an asymmetric carbon atom), a process for preparing such compounds, the liquid crystal compositions containing said compounds as active ingredient, and the liquid crystal elements using such compositions.

Among the aromatic compounds having a trifluoromethyl group of the formula (1) according to this invention, those of the formula (1) wherein X is —COO— can be produced by reacting a carboxylic acid compound represented by the formula (2):

(wherein $R^1$, k, Ar and Y have the same meaning as those defined above, and R' is a hydroxyl group or a halogen atom) with an optically active phenol derivative represented by the formula (3):

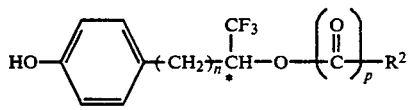

(wherein $R^2$, n, p and * mark have the same meaning as those defined above) in the presence of a catalyst or a condensation agent.

Examples of the carboxylic acid compounds of the formula (2) usable in the above reaction include 4-alkoxybenzoic acid, 4-alkylbenzoic acid, 4-alkoxycarbonylbenzoic acid, 4-alkylcarbonyloxybenzoic acid, 4'-alkoxy-4-biphenylcarboxylic acid, 4'-alkyl-4-biphenylcarboxylic acid, 4'-alkoxycarbonyl-4-biphenylcarboxylic acid, 4'-alkylcarbonyloxy-4-biphenylcarboxylic acid, 2-(4-hydroxycarbonylphenyl)-5-alkoxypyrimidine, 2-(4-hydroxycarbonylphenyl)-5-alkylpyrimidine, 2-(4-hydroxycarbonylphenyl)-5-alkoxycarbonylpyrimidine, and 2-(4-hydroxycarbonylphenyl)-5-alkylcarbonyloxypyrimidine. These carboxylic acids can be used in the form of an acid halide such as acid chloride or acid bromide.

The "alkyl" or "alkoxyl" in the above-mentioned compunds refers to an alkyl group $R^1$ of 3-20 carbon atoms. Examples of said alkyl groups are propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl and eicosyl. Exemplary of the optically active phenol derivatives usable as a reactant in the above reaction are 4-(1-alkoxy-2,2,2-trifluoroethyl)phenol, 4-(2-alkoxy-3,3,3-trifluoropropyl)phenol, 4-(3-alkoxy-4,4,4-trifluorobutyl)phenyl, 4-(4-alkoxy-5,5,5-trifluoropentyl)phenol, 4-(5-alkoxy-6,6,6-trifluorohexyl)phenol, and 4-(6-alkoxy-7,7,7-trifluoroheptyl)phenol. It is also possible to use the compounds in which "alkoxy" in the above-cited derivatives was replaced by alkoxyalkoxy, alkylcarbonyloxy or alkoxyalkylcarbonyloxy.

The alkoxy, alkoxyalkoxy, alkylcarbonyloxy and alkoxyalkylcarbonyloxy mentioned above correspond to

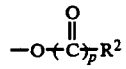

in the above-shown formula (3), and the substituent $R^2$ therein is an alkyl or alkoxyalkyl group of 1-20 carbon atoms which may be substituted with a halogen atom. Such an alkyl or alkoxyalkyl group may be of straight chain or branched. In the latter case, said group may be an optical active group.

Examples of said alkyl or alkoxyalkyl group are methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, methoxymethyl, methoxyethyl, methoxypropyl, methoxybutyl, methoxypentyl, methoxyhexyl, methoxyheptyl, methoxyoctyl, methoxynonyl, methoxydecyl, ethoxymethyl, ethoxyethyl, ethoxypropyl, ethoxybutyl ethoxypentyl, ethoxyhexyl, ethoxyheptyl, ethoxyoctyl, ethoxynonyl, ethoxydecyl, propoxymethyl, propoxyethyl, propoxypropyl, propoxybutyl, propoxypentyl, propoxyhexyl, propoxyheptyl, propoxyoctyl, propoxynonyl, propoxydecyl, butoxymethyl, butoxyethyl, butoxypropyl, butoxybutyl, butoxypentyl, butoxyhexyl, butoxyheptyl, butoxyoctyl, butoxynonyl, butoxydecyl, pentyloxymethyl, pentyloxyethyl, pentyloxypropyl, pentyloxybutyl, pentyloxypentyl, pentyloxyhexyl, pentyloxyoctyl, pentyloxydecyl, hexyloxymethyl, hexyloxyethyl, hexyloxypropyl, hexyloxybutyl, hexyloxypentyl, hexyloxyhexyl, hexyloxyoctyl, hexyloxynonyl, hexyloxydecyl, heptyloxymethyl, heptyloxyethyl, heptyloxypropyl, heptyloxybutyl, heptyloxypentyl, octyloxymethyl, octyloxyethyl, octyloxypropyl, decyloxymethyl, decyloxyethyl, decyloxypropyl, 1-methylethyl, 1-methylpropyl, 1-methylbutyl, 1-methylpropyl, 1-methylbutyl, 1-methylpentyl, 1-methylhexyl, 1-methylheptyl, 1-methyloctyl, 2-methylethyl, 2-methylbutyl, 2,3-dimethylbutyl, 2,3,3-trimethylbutyl, 2-methylpentyl, 3-methylpentyl, 2,3-dimethylpentyl, 2,4-dimethylpentyl, 2,3,3,4-tetramethylpentyl, 2-methylhexyl, 3-methylhexyl, 4-methylhexyl, 2,5-dimethylhexyl, 2-methylheptyl, 2-methyloctyl, 2-trihalomethylpentyl, 2-trihalomethylhexyl, 2-trihalomethylbutyl, 2-haloethyl, 2-halopropyl, 3-halopropyl, 3-halo-2-methylpropyl, 2,3-dihalopropyl, 2-halobutyl, 3-halobutyl, 4-halobutyl, 2,3-dihalobutyl, 2,4-dihalobutyl, 3,4-dihalobutyl, 2-halo-3-methylbutyl, 2-halo-3,3-dimethylbutyl, 2-halopentyl, 3-halopentyl, 4-halopentyl, 5-halopentyl, 2,4-dihalopentyl, 2,5-dihalopentyl, 2-halo-3-methylpentyl, 2-halo-4-methylpentyl, 2-halo-3-monohalomethyl-4-methylpentyl, 2-halohexyl, 3-halohexyl, 4-halohexyl, 5-halohexyl, 6-halohexyl, 2-haloheptyl, and 2-halooctyl, ("Halo" in the above alkyl groups denotes fluorine, chlorine, bromine or iodine.)

When p in the above formula is 1, the substituent $R^2$ may be, beside those mentioned above, halomethyl, 1-haloethyl, 1-halopropyl, 1-halobutyl, 1-halopentyl, 1-halohexyl, 1-haloheptyl, 1-haloocytl and the like.

An ordinary esterification method may be applied for performing the reaction between said carboxylic acid compound (2) and optically active phenol derivative (3). This reaction can be carried out either in the presence or in the absence of a solvent.

In case of using a solvent in this reaction, such a solvent is selected from those which are inert to the reaction, for example, aliphatic or aromatic hydrocarbons, ethers, halogenated hydrocarbons, organic amines and the like. More specifically, they include tetrahydrofuran, ethylether, acetone, methyl ethyl ketone, toluene, benzene, chlorobenzene, dichloromethane, dichloroethane, chloroform, carbon tetrachloride, dimethylformamide, hexane, pyridine and the like. These solvents may be used either singly or in combination. The amount of the solvent(s) used in the reaction is not subject to particular restrictions.

In this reaction, since the optically active phenol derivatives (3) are relatively expensive, it is recommended to use the other reactant, viz. carboxylic acid compound (2), in an excess amount. Usually the compound (2) is used in an amount of 1–4 equivalents, preferably 1–2 equivalents to the derivative (3).

As catalyst, there can be used, for example, organic or inorganic basic substances such as dimethylaminopyridine, triethylamine, tri-n-butylamine, pyridine, picoline, collidine, imidazole, sodium carbonate, sodium methylate, or potassium hydrogencarbonate. It is also possible to use such organic or inorganic acids as toluenesulfonic acid, methanesulfonic acid, sulfuric acid or the like.

The amount of the catalyst used in the reaction is variable depending on the kind of the reaction starting materials, combination thereof with the catalyst used and other factors, but in case of using, for instance, an acid halide as the reactant (2), a basic substance is used (as catalyst) in an amount of more than one equivalent to said acid halide.

In case the carboxylic acid compound of the formula (2) is a carboxylic acid, it is preferred to use a carbodiimide such as N,N'-dicyclohexylcarbodiimide, N-cyclohexyl-4'-(4-diethylamino)cyclohexylcarbodiimide or the like as condensation agent, and if necessary an organic base such as 4-pyrrolidinopyridine, pyridine, triethylamine or the like may be used jointly with said condensation agent.

The condensation agent is used in an amount of usually 1–1.2 equivalents to the optically active phenol derivative (3), and in case of jointly using an organic base, its amount used is usually 0.01–0.2 equivalent to the condensation agent.

The reaction temperature used in the reaction between the carboxylic acid compound (2) and optically active phenol derivative (3) is usually in the range from −30° C. to 100° C., preferably from −25° C. to 80° C. The reaction time is not specifically defined.

After the reaction, the objective optically active aromatic compound having a trifluoromethyl group represented by the formula (1) (where X is —COO—) can be isolated from the reaction mixture by a usual separating means such as extraction, liquid separation, concentration, etc. If necessary the resulting product may be purified by suitable means such as column chromatography, recrystallization, etc.

An optically active phenol derivative (3) used as a starting material can be produced according to any of the processes described below.

(1) In case n in the formula (3) is 0:

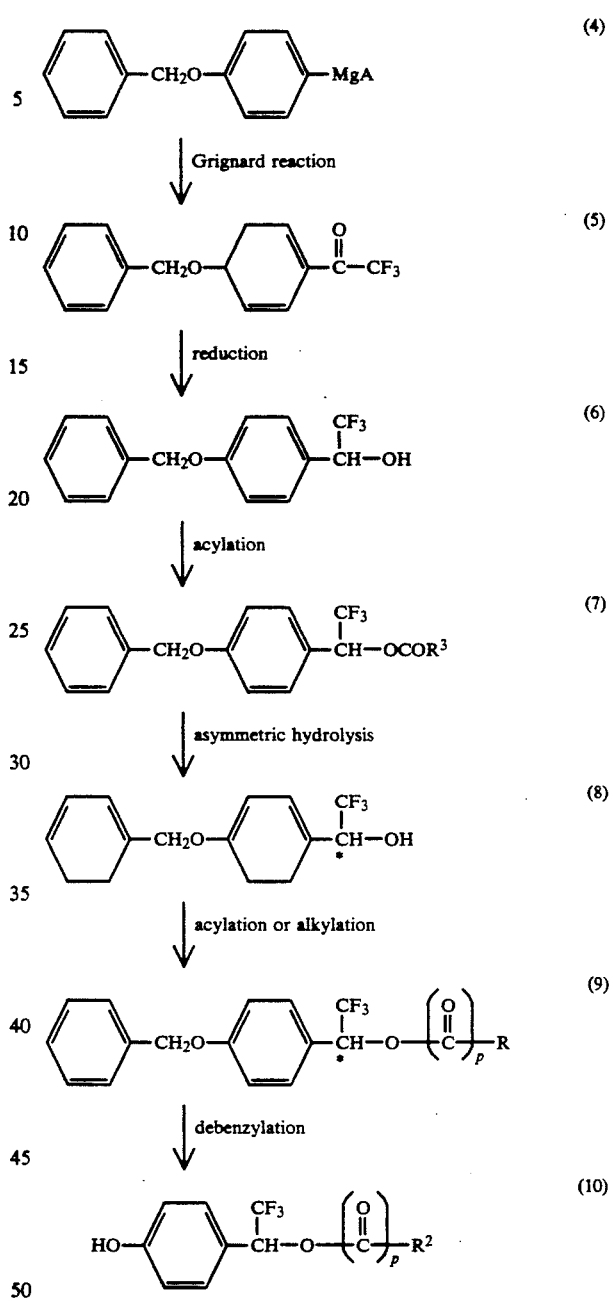

(In the above formulae, $R^2$, p and * mark denote the same as defined above, A is chlorine, bromide or iodine atom, and $R^3$ is lower alkyl group).

The process will be described in detail stepwise below.

The first step of the process comprises a Grignard reaction where a Grignard reagent represented by the formula (4) and a trifluoroacetic acid or a derivative thereof are reacted to give a trifluoroacetophenone derivative represented by the formula (5).

The Grignard reagent (4) can be prepared from a corresponding halogenobenzene derivative and magnesium.

As trifluoroacetic acid or a derivative thereof used in the above reaction, there can be employed, beside trifluoroacetic acid, trifluoroacetyl halides such as trifluoroacetyl chloride and trifluoroacetyl bromide, esters such as methyl trifluoroacetate and ethyl trifluoroacetate, acid amides such as N-trifluoroacetylimidazole, trifluoroacetic acid anhydride, or the like. The amount of trifluoroacetic acid or a derivative thereof used in the above reaction needs to be not less than one equivalent, usually 1-3 equivalents to the Grignard reagent (4) excepting the case where trifluoroacetic acid is used. In the latter case, the reaction is carried out by using the Grignard reagent (4) in an amount of 2 or greater equivalents, usually 2-4 equivalents, to one equivalent of trifluoroacetic acid.

As solvent, one can use ethers such as ethyl ether and tetrahydrofuran, aromatic hydrocarbons such as benzene, toluene and xylene, and the like, either singly or in combination. No particular restrictions are imposed on the amount of the solvent used in the reaction.

The reaction temperature is usually in the range from $-120°$ C. to $0°$ C., preferably from $-100°$ C. to $20°$ C. Reaction time is not specifically defined.

Isolation of the trifluoroacetophenone derivative of the formula (5) from the reaction mixture can be effected by subjecting the reaction mixture to the ordinary after-treatment operations such as extraction, liquid separation, concentration and recrystallization or column chromatography.

The second step of the process comprises reducing the trifluoroacetophenone derivative of the formula (5) to obtain a β-phenethyl alcohol derivative represented by the formula (6).

In this reducing reaction, there is used a reducing agent that can reduce ketone into alcohol. Typical examples of such reducing agent are lithium aluminum hydride, sodium borohydride and boron hydride. Such a reducing agent is used in an amount of one or greater equivalents, usually 1-10 equivalents, to the trifluoroacetophenone derivative (5) used as starting material.

This reducing reaction is carried out in a solvent. As such a solvent, there can be used ethers such as tetrahydrofuran, dioxane or ethyl ether, alcohols such as methanol, ethanol, n-propyl alcohol or isopropyl alcohol, aromatic hydrocarbons such as toluene and benzene, or halogenated hydrocarbons such as chloroform and dichloromethane. These solvents may be used either singly or in combination.

The reaction is carried out at a temperature usually in the range from $-30°$ C. to $100°$ C., preferably from $-20°$ C. to $90°$ C.

The end point of the reaction is usually supposed to be the moment when the trifluoroacetophenone derivative (5) has disappeared from the reaction system.

Isolation of the β-phenetyl alcohol derivative of the formula (6) can be achieved by conducting the ordinary after-treatment operations such as extraction, liquid separation, concentration, etc.

The third step comprises acylating the β-phenyl alcohol derivative (6) with a carboxylic acid represented by the formula (10):

$$R^3COOH \quad (10)$$

(wherein $R^3$ is as defined above) or a derivative thereof in a solvent in the presence of a catalyst to form an ester represented by the formula (7).

As said carboxylic acid (10) or a derivative thereof, there can be used, for example, acetic acid, propionic acid, acetic anhydride, propionic anhydride, acetic acid chloride or bromide, propionic acid chloride or bromide, butyryl chloride or bromide, valeroyl chloride or bromide, and the like. The amount of such a carboxylic acid or a derivative thereof used in the acylation should be not less than one equivalent to the β-phenetyl alcohol derivative (6). The upper limit of said amount is not specifically restricted but recommended to be 4 equivalents to the β-phenetyl alcohol derivative (6).

The acylation is conducted in the presence of a catalyst. As catalyst, there can be used, for example, organic or inorganic basic substances such as dimethylaminopyridine, triethylamine, tri-n-butylamine, pyridine, picoline, imidazole, sodium carbonate, sodium methylate and potassium hydrogencarbonate. It is also possible to use acids such as toluenesulfonic acid, methanesulfonic acid and sulfuric acid. The amount of such a catalyst used in the acylation is not specified, but usually it is used in an amount of 1-5 equivalents to the β-phenetyl alcohol derivative (6). The solvent used in said acylation reaction is the one which is inert to the reaction, for example, aliphatic or aromatic hydrocarbons, ethers, halogenated hydrocarbons, aprotic polar solvents and organic amines, more specifically, tetrahydrofuran, ethyl ether, acetone, methyl ethyl ketone, hexane, toluene, benzene, chlorobenzene, dichloromethane, dichloroethane, chloroform, carbon tetrachloride, dimethylformamide, pyridine and the like. These solvents may be used either singly or in combination. No particular limitations are given to the amount of the solvent used in the reaction.

In case of using an organic amine as solvent, it may also act as a catalyst.

Reaction temperature is usually in the range from $-30°$ C. to $100°$ C., preferably from $-20°$ C. to $90°$ C.

Reaction time is not specifically defined. The moment when the starting material β-phenetyl alcohol derivative (6) has disappeared from the reaction system may be regarded as the end point of the reaction.

Isolation of an ester of the formula (7) may be accomplished by subjecting the reaction mixture to the ordinary after-treatment operations such as extraction, liquid separation, concentration, recrystallization, etc.

The fourth step comprises asymmetric hydrolysis of the ester (7) with an esterase having the ability to preferentially hydrolyze one of the optical isomers of said ester to produce an optically active alcohol compound.

The esterase used in the above asymmetric hydrolysis reaction is obtainable from animals, vegetables or microorganisms. It can be used in various forms such as purified enzyme, crude enzyme, enzyme-containing substance, liquid culture of microorganism, culture, cell, culture filtrate and treated substance thereof. A combination of an enzyme and a microorganism is also usable. It is further possible to use the fixed enzyme or fixed cell formed by fixing the enzyme or cell to a resin or other substance.

The term "esterase" used in this specification of the invention means esterase in its broad sense, which includes lipase.

As the microorganism producing an esterase used in the above asymmetric hydrolysis reaction, there can be employed any of those microorganisms which can produce an esterase having the ability to asymmetrically hydrolyze an ester of the formula (7). Examples of these microorganisms are those belonging to the general Enterobacter, Arthrobacter, Previbacterium, Pseudomonas, Alcaligenes, Micrococcus, Chromobacterium, Microbacterium, Corynebacterium, Bacillus, Lactobacillus, Trichoderma, Candida, Saccharomyces, Rhodotorula, Cryptococcus, Torulopsis, Befia, Penicillium, Aspergillus, Phizopus, Mucor, Aureobacidium, Actinomucor, Nocardia, Streptomyces, Hansenula and Achromobacter.

Cultivation of said microorganisms can be usually accomplished according to a conventional method, and a liquid culture can be obtained by performing liquid cultivation.

For instance, a sterilized liquid medium [a malt extract/yeast extract medium (prepared by dissolving 5 g of peptone, 10 g of glucose, 3 g of melt extract and 3 g of yeast extract in 1 liter of water, with pH adjusted to 6.5) for mold and yeast and a sweetened bouillon medium (prepared by dissolving 10 g of glucose, 5 g of peptone, 5 g of meat extract and 3 g of NaCl in 1 liter of water, with pH adjusted to 7.2) for bacterial] is inoculated with a microorganism and the latter is subjected to reciprocal shaking culture usually at 20° to 40° C. for 1 to 3 days. Solid culture may be employed if necessary.

Among the esterases derived from the microorganisms such as mentioned above, there are those which are commercially prepared and easily available. Listed below are the examples of the commercially available esterases: Lipase P (lipase of the genus Pseudomonas, available from Amano Pharmaceutical Co., Ltd.), Lipase AP (lipase of the genus Aspergillus, available from Amano Pharmaceutical Co., Ltd.), Lipase M-AP (lipase of the genus Mucor, available from Amano Pharmaceutical Co., Ltd.), Lipase MY (lipase of Candida available from Meito Sangyo Co., Ltd.), Lipase PL (lipase of the genus Alcaligenes, available from Meito Sangyo Co., Ltd.), Lipase Al (lipase of the genus Acromobacter, available from Meito Sangyo Co., Ltd.), Lipase Godo BSL (lipase of the genus Arthrobacter, available from Godo Shusei Co., Ltd.), lipase of the genus Chromobacterium, available from Toyo Brewage Co., Ltd., Talipase (lipase of Rhizopus.delemer, available from Tanabe Pharmaceutical Co., Ltd.), and Lipase Saiken (liphase of the genus Rhizopus, available from Osaka Bacteria Research Institute.

It is also possible to use esterases of animal or vegetable sources. Examples of such esterases are steapsin, pancreatin, swine liver esterase, and wheat germ esterase.

The asymmetric hydrolysis reaction is carried out by vigorously stirring a mixture of a starting ester of the formula (7) and one of said enzymes or microorganisms usually in a buffer solution.

The buffer solution used in the above reaction can be a commonly employed buffer solution of a salt of an inorganic acid such as sodium phosphate and potassium phosphate or a salt of an organic acid such as sodium acetate and sodium citrate. The pH of such a buffer solution is preferably 8 to 11 in the case of liquid cultures of alkaliphilic bacteria or alkaline esterases and 5 to 8 in the case of liquid cultures of non-alkaliphilic microorganisms or esterases having no alkali resistance.

Concentration of the buffer solution is usually in the range of 0.05 to 2M, preferably 0.05 to 0.5M.

Reaction temperature is usually 10° to 60° C., and reaction time is generally 10 to 70 hours, but both are not always defined within said ranges.

It is to be noted that in case of using lipase belonging to the genus Pseudomonas or genus Arthrobacter in said asymmetric hydrolysis reaction, there can be obtained an optically active alcohol compound (8) with a relatively high optical purity.

In carrying out said asymmetric hydrolysis, it is possible to use an organic solvent inert to the reaction, such as toluene, chloroform, methyl isobutyl ketone, dichloromethane and the like in addition to a buffer solution. Use of such a solvent enables advantageous execution of said asymmetric hydrolysis reaction.

In said asymmetric hydrolysis reaction, only one of the optical isomers of the starting ester (7) is preferentially hydrolyzed to produce an optically active alcohol compound represented by the formula (8). The other optical isomer remains in the form of ester compound as a residue of asymmetric hydrolysis.

Isolation of the optically active alcohol compound (8) from the reaction mixture can be accomplished, for example, in the following way: the reaction mixture, which has undergone the ordinary after-treatments, is extracted with a solvent such as ethyl acetate, then the solvent is evaporated away from the obtained organic layer, and the residue is concentrated and column chromatographed.

In this way, there are obtained an optically active alcohol compound (8) as the asymmetric hydrolysis product and an optically active ester (7) as the residue of the asymmetric hydrolysis. If desired, this residual optically active ester may be further hydrolyzed and made into an optically active alcohol compound (8) which is an enantiomer of the compound obtained from said asymmetric hydrolysis reaction.

The fifth step comprises acylation or alkylation of the optically active alcohol compound (8) to obtain an optically active benzyloxybenzene derivative represented by the formula (9).

The optically active benzyloxybenzene derivative represented by the formula (9) in which p is 1 can be produced by reacting an optically active alcohol compound (8) with a carboxylic acid represented by the formula (11):

$$R^2COOH \qquad (11)$$

(where $R^2$ has the same meaning as defined above) or a derivative thereof in the presence of a catalyst or a condensation agent.

The substituent $R^2$ in the above formula (11) may be the same alkyl or alkoxyl group as the substituent $R^2$ in the optically active phenol derivatives represented by the above-shown formula (3).

In said acylation reaction, there is used a carboxylic acid having said substituent $R^2$, an acid anhydride or an acid halide such as acid chloride or acid bromide.

Said carboxylic acids or derivatives thereof may be either a racemate or an optically active form. In the latter case, some of such carboxylic acids can be obtained through oxidation of corresponding alcohols or reductive deamination of amino-acids. Also, there are those which occur naturally or can be derived from the optically active amino-acids or optically active oxyacids which are obtainable through resolution. Examples of such optically active amino-acids or oxyacids include aniline, valine, leucine, isoleucine, phenylalanine, serine, threonine, allothreonine, homoserine, alloisoleucine, tert-leucine, 2-aminobutyric acid, norvaline, norleucine, ornithine, lysine, hydroxylysine, phenylglycine, trifluoroalanine, aspartic acid, glutamic acid, lactic acid, mandelic acid, tropic acid, 3-hydroxybutyric acid, malic acid, tartaric acid, and isopropylmalic acid.

The reaction of such a carboxylic acid or a derivative thereof with an optically active alcohol compound of the formula (8) is carried out either in the presence of or without a solvent.

As solvent, there can be used, for example, aliphatic or aromatic hydrocarbons such as tetrahydrofuran, ethyl ether, acetone, methyl ethyl ketone, toluene, benzene, chloroform, chlorobenzene, dichloromethane, dichloroethane, carbon tetrachloride, dimethylformamide or hexane, and the solvents which are inert to the reaction, such as ethers, ketones, amides or halogenated hydrocarbons. These solvents may be used either singly or in combination. No particular restrictions are imposed on the amount of such a solvent used in the reaction.

In the case of using an acid anhydride or an acid halide in this reaction, the reaction is conducted by using a catalyst.

An acid anhydride or an acid halide is used in an amount not less than one equivalent to the optically active alcohol compound (8). The upper limit of the amount of such acid anhydride or acid halide usable in the reaction is not specifically defined, but preferably it is not greater than 4 equivalents to said compound (8).

As catalyst, there can be used organic or inorganic basic substances such as dimethylaminopyridine, triethylamine, tri-n-butylamine, pycoline, imidazole, sodium carbonate and potassium hydrogen carbonate. It is also possible to use organic or inorganic acids such as toluenesulfonic acid, methanesulfonic acid and sulfuric acid.

The amount of the catalyst used in the reaction is not specified, but in the case of using, for instance, an acid halide, the catalyst is used in an amount not less than one equivalent to the acid halide.

In case of using a carboxylic acid represented by the formula (11) in the reaction, the reaction is carried out in the presence of a condensation agent. The amount of the carboxylic acid used in the reaction is usually 1 to 2 equivalents to the optically active alcohol compound (8).

As condensation agent, carbodiimides such as N,N'-dicyclohexylcarbodiimide and N-cyclohexyl-N'-(4-diethylamino)cyclohexylcarbodiimide are preferably used. If necessary, an organic base such as 4-pyrrolidinopyridine, pyridine and triethylamine may be used in combination with the condensation agent.

The amount of the condensation agent used in the reaction is 1 to 1.2 equivalents to the carboxylic acid (11), and in case of using an organic base, it is used in an amount of 0.01 to 0.2 equivalent to the condensation agent.

The reaction is carried out at a temperature usually in the range of $-80°$ C. to $120°$ C., preferably $-20°$ C. to $90°$ C.

Reaction time is not specifically defined. The moment when the optically active alcohol compound (8) has disappeared from the reaction system may be considered as the end point of the reaction.

Isolation of the optically active benzyloxybenzene derivative of the formula (9) where p is 1 from the reaction mixture can be accomplished by conducting the ordinary after-treatment operations such as extraction liquid separation, concentration, recrystallization or column chromatography.

The optically active benzoxybenzene derivative of the formula (9) where p is 0 can be obtained by alkylating the optically active alcohol compound (8) with an alkylating agent represented by the formula (12):

$$R^2-Z \quad (12)$$

(wherein $R^2$ designates the same as defined above, and Z represents a halogen atom or $-OSO_2R''$ where $R''$ is a lower alkyl group or a phenyl group which may be substituted) in a solvent in the presence of a basic substance.

As the basic substance, there can be used alkali metal hydrides such as sodium hydride and potassium hydride; alkali metal or alkaline earth metal hydroxides such as sodium hydroxide, potassium hydroxide and calcium hydroxide; alkali metal carbonates such as sodium carbonate and potassium carbonate; butyl lithium; or alkali metals such as lithium, sodium and potassium.

Such a basic substance is used in an amount not less than one equivalent to the optically active alcohol compound (8). The upper limit of the usable amount of this substance is not restricted but preferably not greater than 5 equivalents to said compound (8).

The alkylating agent (12) used in this reaction is selected from the halides such as chlorides, bromides and iodides having an alkyl or alkoxyalkyl group of 1 to 20 carbon atoms which may be substituted with a halogen atom or the sulfonic acid esters (methanesulfonic acid ester, ethanesulfonic acid ester, benzenesulfonic acid ester, toluenesulfonic acid ester, benzenesulfonic acid ester, toluenesulfonic acid ester, etc.)

The substituent $R^2$ in the alkylating agents represented by the formula (12) is identical with the substituent $R^2$ in the optically active phenol derivatives represented by the formula (3). These alkylating agents (12) can be easily prepared from the corresponding alcohols as desired.

The substituent $R^2$ in the alkylating agent (12) may be an optically active group, and the alkylating agents (halides or sulfonic acid esters) having such an optically active group can be synthesized from the corresponding optical active alcohols as desired.

Some of said optically active alcohols can be easily obtained from asymmetric reduction of the corresponding ketones with an asymmetric metallic catalyst, microorganism or enzyme. There are also those of said optically active alcohols which occur naturally or can be derived from the optically active amino acids or optically active oxyacids such as mentioned below which can be obtained by resolution: valine, leucine, isoleucine, phenylalanine, threonine, allothreonine, homoserine, alloisoleucine, tert-leucine, 2-aminobutyric acid, norvaline, norleucine, ornithine, lysine, hydroxylysine, phenylglycine, aspartic acid, glutamic acid, mandelic acid, tropic acid, 3-hydroxybutyric acid, malic acid, tartaric acid, isopropylmalic acid or the like.

The amount of the alkylating agent (12) used in the reaction can be optionally selected provided that it is not less than one equivalent to the optically active alcohol compound (8), but usually said alkylating agent is used in an amount of 1 to 5 equivalents to said compound (8).

As the reaction solvent, there can be used ethers such as tetrahydrofuran and ethyl ether, ketones such a acetone and methyl ethyl ketone, aromatic hydrocarbons such as toluene and benzene, halogenated hydrocarbons such as chloroform, dichloromethane, dichloroethane and chlorobenzene, aliphatic hydrocarbons such as pentane and hexane, and polar solvents such as dimethylformamide, dimethyl sulfoxide, hexamethylphosphoramide or N-methylpyrrolidone.

The reaction is usually carried out at a temperature of usually −50° C. to 120° C., preferably −80° C. to 100° C.

Reaction time is not specifically defined, but usually the moment when the optically active alcohol compound of the formula (8) has disappeared from the reaction system may be supposed to be the end point of the reaction.

Isolation of the optically active benzyloxybenzene derivative of the formula (9) wherein p is 0 from the reaction mixture can be effectuated by performing the ordinary after-treatments such as extraction, liquid separation, concentration, recrystallization or column chromatography.

The sixth step comprises debenzylation of the optically active benzyloxybenzene derivative (9) in the presence of a hydrogenerated catalyst and hydrogen to obtain the objective optically active phenol derivative of the formula (3) wherein n is 0.

The hydrogenated catalysts usable in the above debenzylation reaction include platinum catalysts such as $PtO_2$ and Pt-C, palladium catalysts such as Pd-C, Pd-BaSO$_4$ and palladium black, rhodium catalysts such as Rh-C and Rh-Al$_2$O$_3$, ruthenium catalysts such as $RuO_2$ and Ru-C, and nickel catalysts such as Raney nickel. Among them, palladium catalysts are the most preferred.

The hydrogenated catalyst is used in an amount of usually 0.01 to 100% by weight, preferably 0.1 to 50% by weight, based on the optically active benzyloxybenzene derivative of the formula (9).

As solvent, there can be used alcohols such as methanol and ethanol, ethers such as dioxane and tetrahydrofuran, aromatic hydrocarbons such as benzene and toluene, aliphatic hydrocarbons such as n-hexane and cyclohexane, esters such as ethyl acetate, amides such as dimethylformamide, fatty acids such as acetic acid, and water. These solvents can be used either singly or in combination.

Hydrogen pressure in the reaction is usually 1 to 200 atm.

Reaction temperature is usually 0° to 200° C., preferably 20° to 180° C.

Reaction time is variable depending on he kind of the hydrogenated catalyst used, reaction temperature and hydrogen pressure, but the end point of the reaction is usually decided by the moment of disappearance of the optically active benzyloxybenzene derivative of the formula (9) or cessation of hydrogen absorption.

Isolation of the optically active phenol derivative of the formula (3) where n is 0 from the reaction mixture can be accomplished by subjecting the reaction mixture to the ordinary after-treatments such as filtration, concentration, recrystallization, distillation or column chromatography.

(2) In case n in the formula (3) is an integer of 1 to 5:

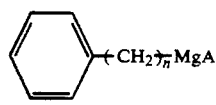

[13]

↓ Grignard reaction

-continued

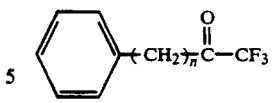

[14]

↓ reduction

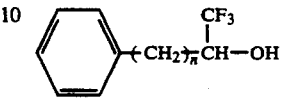

[15]

↓ acylation

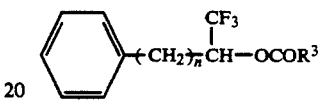

(16)

↓ Friedel-Crafts reaction

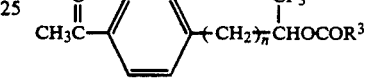

(17)

↓ asymmetric hydrolysis

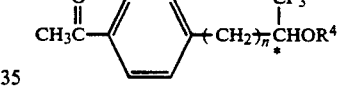

(18)

↓ Baeyer-Villiger oxidation

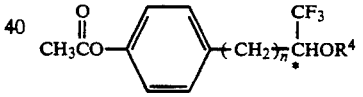

(19)

↓ hydrolysis

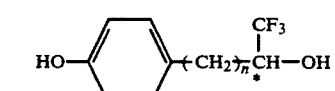

(20)

↓ benzylation

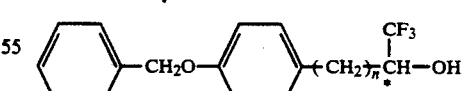

(21)

↓ acylation or alkylation

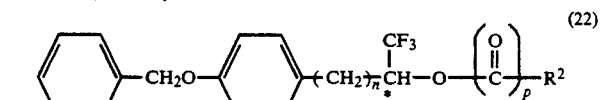

(22)

↓ debenzylation

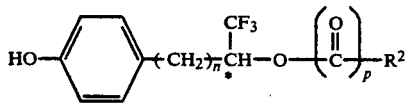

(3)

(In the above formulae, $R^2$, $R^3$, A, p and * mark denote the same as defined above, and $R^4$ represents hydrogen atom or —$COR^3$.)

The process will be described stepwise below.

The first step comprises a Grignard reaction in which a Grignard reagent represented by the formula (13) is reacted with trifluoroacetic acid or a derivative thereof to obtain a ketone compound represented by the formula (14).

The Grignard reagent (13) can be prepared from the corresponding ω-halogenoalkylbenzene and magnesium.

This reaction is identical with the reaction in the first step in the above-described process (1) for the preparation of optically active phenol derivative (13). Thus, by conducting the reaction and after-treatment after the manner of the first step in the process (1), it is possible to obtain a ketone compound of the formula (14).

The second step comprises reduction of said ketone compound (14) to form an alcohol compound represented by the formula (15). The reduction reaction is similar to the reaction in the second step of the above-described process (1), and by performing the reaction and after-treatment in accordance with the second step of said process (1), it is possible to obtain the alcohol compound of the formula (15).

The third step comprises acylating the alcohol compound (15) with a carboxylic acid of the formula (10) or a derivative thereof to produce an ester compound represented by the formula (16).

This acylating reaction is the same as the reaction conducted in the third step of the process (1) described above, so that by carrying out the reaction and after-treatment according to this step, it is possible to obtain an ester compound of the formula (16).

The fourth step comprises acylation of said ester compound (16) by a Friedel-Crafts reaction to obtain an acetophenone derivative represented by the formula (17).

Acetic acid and its derivatives such as acetyl chloride and acetyl bromide can be used as the acylating agent in said Friedel-Crafts reaction. The amount of the acylating agent used in said reaction should be not less than one equivalent to the ester compound (16). The upper limit of the amount of said acylating agent usable in said reaction is not specifically defined but usually it is 3 equivalents to the ester compound (16).

A catalyst is used in this reaction. Examples of such catalyst are aluminum chloride, aluminum bromide, zinc chloride, zinc bromide, titanium tetrachloride, polyphosphoric acid, boron trifluoride or the like. The amount of the catalyst used in the reaction is usually in the range of 0.3 to 3 equivalents to the ester compound (16).

Reaction temperature is between −30° C. and 150° C., preferably between −10° C. and 100° C.

Reaction time is not regulated. The moment at which the starting ester compound (16) has disappeared from the reaction system can be deemed as the end point of the reaction.

Isolation of an acetophenone derivative of the formula (17) from the reaction mixture can be achieved by conducting the ordinary operations of after-treatment such as extraction, liquid separation and concentration. If necessary, the obtained product may be subjected to an additional treatment(s) such as column chromatography for further purification.

The fifth step comprises asymmetric hydrolysis of the acetophenone derivative (17) by using an esterase having the ability to preferentially hydrolyze only one of the optical isomers of said acetophenone derivative (17) to give an optically active acetophenone derivative represented by the formula (18).

In this reaction, said acetophenone derivative (17) is subjected to asymmetric hydrolysis under the same conditions of reaction and after-treatment as used in the fourth step of the process (1) described before, whereby there can be obtained, as the hydrolyzate, an optically active acetophenone derivative represented by the formula (18) where $R^4$ is hydrogen atom and, as the residue of the asymmetric hydrolysis, an optically active acetophenone derivative of the formula (18) where $R^4$ is —$COR^3$.

The sixth step comprises Baeyer-Villiger oxidation of the optically active acetophenone derivative (18) to obtain an optically active acetoxybenzene derivative represented by the formula (19).

Peracids such as peracetic acid, performic acid, m-chloroperbenzoic acid, perbenzoic acid, etc., can be used as oxidizing agent for said Baeyer-Villiger oxidation. Such peracids can be produced, for instance, from the corresponding acids and hydrogen peroxide.

The amount of the peracid used in said oxidation reaction is not less than one equivalent to the optically active acetophenone derivative (18). Its upper limit is not specifically defined but usually 2 equivalents to said acetophenone derivative (18).

In this reaction, usually a solvent inert to the reaction is used. As such a solvent, there can be used halogenated hydrocarbons and aromatic or aliphatic hydrocarbons such as dichloromethane, dichloroethane, chloroform, chlorobenzene, benzene, toluene, xylene, hexane or cyclohexane, either singly or in combination. The amount of the solvent used in the reaction is not specified.

Reaction temperature is usually in the range of −20° C. to 130° C., preferably −10° C. to 100° C.

Reaction time is not restricted. The moment of disappearance of the starting optically active acetophenone derivative (18) from the reaction system may be regarded as the end point of the reaction.

Isolation of the optically active acetoxybenzene derivative (19) from the reaction mixture can be attained by performing the ordinary after-treatment operations such as removal of excess peracid, extraction, liquid separation, concentration, etc. If necessary, the resulting product may be column-chromatographed or otherwise treated for further purification.

The seventh step comprises hydrolysis of the optically active acetoxybenzene derivative (19) to obtain an optically active diol represented by the formula (20).

This reaction is carried out by using an acid or an alkali in the presence of water.

The acid used in this reaction can be selected from such inorganic acids as sulfuric acid, phosphoric acid, hydrochloric acid and the like or such organic acids as toluenesulfonic acid, methanesulfonic acid or the like.

As the alkali, there can be used organic or inorganic bases such as sodium hydroxide, potassium hydroxide, barium hydroxide, potassium carbonate, sodium carbonate and 1,8-diazabicyclo[5,4,0]-7-undecene.

The amount of the acid or alkali used in the reaction is as described below.

In the case of acid, it is used in an amount of usually 0.02 to 10 equivalents to the optically active acetoxybenzene derivative (19), and in the case of alkali, it is used in an amount not less than one equivalent to said acetoxybenzene derivative (19) when $R^4$ in the formula (19) is hydrogen atom and not less than 2 equivalents to said derivative (19) when $R^4$ is —$COR^3$. No particular restrictions are placed on the upper limit of the amount of the acid or alkali used in the reaction, but usually it is appropriate to set said upper limit at 10 equivalents to said acetoxybenzene derivative (19).

The above reaction is usually carried out in the presence of an organic solvent.

The solvent used in this reaction is selected from those which are inert to the reaction, for example, aliphatic or aromatic hydrocarbons, ethers, alcohols, ketones, amides and halogenated hydrocarbons, more specifically, methanol, ethanol, propanol, acetone, methyl ethyl ketone, chloroform, dichloromethane, toluene, xylene, hexane, heptane, ethyl ether, tetrahydrofuran, dioxane, dimethylformamide, N-methylpyrrolidone or the like. These solvents may be used either singly or in combination.

No particular limitations are imposed on the amount of the solvent usable in the reaction.

Reaction temperature is usually in the range of −30° C. to 150° C., preferably −20° C. to 100° C.

Reaction time is not specifically defined. The end of the reaction can be determined by disappearance of the starting optically active acetoxybenzene derivative (19) from the reaction system.

Isolation of an optically active diol of the formula (20) from the reaction mixture can be accomplished by conducting the ordinary after-treatments such as acid precipitation, extraction, liquid separation, concentration, etc.

The eighth step comprises benzylating the optically active diol (20) with benzyl halide represented by the formula (23):

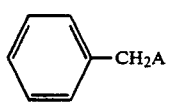

(23)

(wherein A is as defined above) to give an optically active alcohol represented by the formula (21).

This reaction is usually conducted in the presence of a basic substance. As such a basic substance, there can be used alkali metal carbonates such as sodium carbonate and potassium carbonate, alkali metal hydroxides such as sodium hydroxide and potassium hydroxide, or alkali metal alcoholates such as sodium methylate and sodium ethylate.

The amount of the basic substance used in the reaction should be not less than one equivalent, usually 1 to 5 equivalents, to the optically active diol (20).

The solvent used in the reaction is selected from those inert to the reaction such as tetrahydrofuran, dioxane, ethyl ether, acetone, methyl ethyl ketone, dimethylformamide, dimethyl sulfoxide, N-methylpyrrolidone or the like, which may be used either singly or in combination.

The amount of benzyl halide (23) used in this reaction is not less than one equivalent to the optically active diol (20). Its upper limit is not specifically defined but usually 5 equivalents to said diol (20).

Reaction temperature is usually from −20° C. to 150° C., preferably from 0° to 130° C.

Reaction time is not restricted. Disappearance of the starting optically active diol (20) from the reaction system signifies the end of the reaction.

The reaction product is subjected to ordinary separating treatments such as extraction, liquid separation, concentration, etc. to produce an optically active alcohol of the formula (21). This product may be subjected where necessary to an additional treatment such as column chromatography and recrystallization for further purification.

The ninth step comprises acylation or alkylation of the optically active alcohol (21) to obtain an optically active benzyloxybenzene derivative represented by the formula (22).

This reaction is identical with the reaction in the fifth step of the previously described process (1), and by performing the same reaction and after-treatment as in the fifth step of said process (1), it is possible to obtain an optically active benzyloxybenzene derivative of the formula (22).

Thus, in this step, by acylating the optically active alcohol (21) with a carboxylic acid represented by the formula (11) or a derivative thereof, there can be obtained an optically active benzyloxybenzene derivative of the formula (22) where p is 1, and by alkylating said optically active alcohol (21) with an alkylating agent represented by the formula (12), there can be obtained an optically active benzyloxybenzene derivative of the formula (22) where p is 0.

The tenth step comprises debenzylation of the optically active benzyloxybenzene derivative (22) in the presence of a hydrogenated catalyst and hydrogen to obtain an optically active phenol derivative of the formula (3) where n is an integer of 1 to 5.

This reaction is similar to that in the sixth step of the previously described process (1), and thus, by performing the same reaction and after-treatment as in the sixth step of said process (1) on the optically active benzyloxybenzene derivative (22), it is possible to produce the objective optically active phenol derivative of the formula (3) wherein n is an integer of 1 to 5.

(3) In case in the formula (3) n is an integer of 1 to 5 and p is 0:

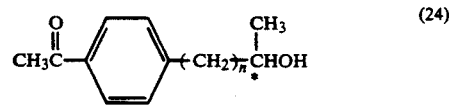

(24)

↓ alkylation

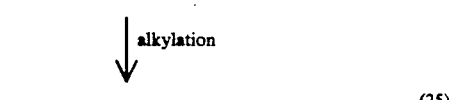

(25)

↓ Baeyer-Villiger oxidation

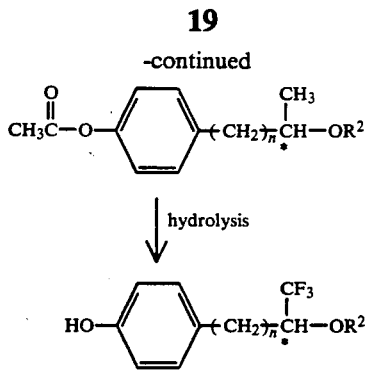

(In the above formulae, R² and * mark denote the same as defined above).

The process for preparing the optically active phenol derivatives of the formula (3) wherein n is an integer of 1 to 5 has been described in (2) above. Preparation of said optically active phenol derivatives (3) is also possible through the above-shown process as far as p in the formula (3) is 0.

This process will be described in detail stepwise below.

The first step comprises alkylation of an optically active alcohol compound of the formula (24) with an alkylating agent represented by the formula (12) to prepare an optically active acetophenone derivative represented by the formula (25).

The optically active alcohol compound of the formula (24) used as starting material in this reaction is the same as the compound of the formula (18) obtained as the hydrolyzate in the asymmetric hydrolysis reaction in the fifth step in the above-described process (2), with $R^4$ in said formula (18) being hydrogen atom.

It is to be also noted that when the compound of the formula (18) where $R^4$ is —COR³ which has been obtained as the residue of the hydrolysis in said asymmetric hydrolysis reaction is further hydrolyzed, there can be obtained a compound of the formula (18) which is an enatiomer of the compound obtained as the hydrolyzate in said hydrolysis reaction, with $R^4$ in said formula (18) being hydrogen atom. This compound can be used as the starting optically active alcohol compound in the present reaction.

This alkylating reaction is the same as the alkylation reaction performed in the fifth step of the previously described process (1), so that by conducting the same reaction and after-treatment as in the fifth step of said process (1) on the optically active alcohol compound (24), it is possible to obtain an optically active acetophenone derivative of the formula (25).

Said alkylating reaction is carried out in the presence of a basic substance. When the substituent Z in the alkylating agent of the formula (12) is an iodine atom, it is possible to use silver oxide in place of the basic substance. In view of reaction yield, it is preferred to carry out the reaction in the presence of silver oxide instead of a basic substance. In this case, the amount of silver oxide used should be not less than one equivalent to the optically active alcohol compound (24) but preferably does not exceed 5 equivalents to said alcohol compound (24) although the upper limit is not defined.

The amount of the alkylating agent of the formula (12) (wherein Z is iodine atom) used in the reaction is optional provided that it is not less than one equivalent to the optically active alcohol compound (24), but usually it is in the range of 2 to 10 equivalents to said alcohol compound (24).

As reaction solvent, said alkylating agent (12) may be used in an excess amount. It is also possible to use other solvents which are inert to the reaction, such as ethers, ketones, hydrocarbons and aprotic polar solvents, more specifically, tetrahydrofuran, ethyl ether, dioxane, acetone, methyl ethyl ketone, benzene, toluene, hexane, dimethylformamide, dimethyl sulfoxide, N-methylpyrrolidone or the like.

Reaction temperature is usually in the range of 0° to 150° C., preferably 20° to 100° C.

Reaction time is usually one hour to 20 days.

After the reaction, the silver salt is filtered out and the residue is subjected to the ordinary after-treatments such as extraction, liquid separation, concentration, etc., to give an optically active acetophenone derivative of the formula (25). The resulting product may be further purified by subjecting it to column chromatography or other treatments.

The second step comprises Baeyer-Villiger oxidation of the optically active acetophenone derivative (25) to obtain an optically active acetoxybenzene derivative represented by the formula (26).

This reaction is identical with the Baeyer-Villiger oxidation reaction in the sixth step of the above-described process (2), and by conducting the reaction and after-treatment in the same way as the sixth step of said process (2), it is possible to obtain the optically active acetophenone derivative (26).

The third step comprises hydrolysis of the optically active acetoxybenzene derivative (26) to produce an objective optically active phenol derivative of the formula (3) wherein n is an integer of 1 to 5 and p is 0.

This reaction is carried out by using an acid or an alkali in the presence of water.

The acid used here can be an inorganic acid such as sulfuric acid, phosphoric acid, hydrochloric acid and the like or an organic acid such as toluenesulfonic acid, methanesulfonic acid or the like.

As alkali, there can be used organic or inorganic bases such as sodium hydroxide, potassium hydroxide, barium hydroxide, potassium carbonate, sodium carbonate or 1,8-diazabicyclo[5,4,0]-7-undecene.

The amount of the acid or alkali used in the reaction is described below.

In the case of acid, it is used in an amount usually in the range of 0.02 to 10 equivalents to the acetoxybenzene derivative (26), and in the case of alkali, it is used in an amount not less than one equivalent to the optically active acetoxybenzene derivative (26). The upper limit of the amount usable is not specifically defined but usually 10 equivalents to said acetoxybenzene derivative (26).

This reaction is usually carried out in the presence of an organic solvent. Such a solvent is selected from those inert to the reaction such as aliphatic or aromatic hydrocarbons, ethers, alcohols, ketones, amides and halogenated hydrocarbons, more specifically, methanol, ethanol, propanol, acetone, methyl ethyl ketone, chloroform, dichloromethane, toluene, xylene, hexane, heptane, ethyl ether, tetrahydrofuran, dioxane, dimethylformamide, N-methylpyrrolidone or the like. These solvents may be used either singly or in combination.

No specific restrictions are imposed on the amount of the solvent used in the reaction.

Reaction temperature is usually in the range from −30° C. to 150° C., preferably from −20° C. to 100° C.

Reaction time is not specifically defined. The reaction may be declared as finished with disappearance of the starting acetoxybenzene derivative (26) from the reaction system.

The reaction product is subjected to the ordinary after-treatments such as acid-precipitation, extraction, liquid separation, concentration, etc., to obtain an objective optically active phenol derivative represented by the formula (3) wherein n is an integer of 1 to 5 and p is 0. If necessary, this product may be further subjected to column chromatography, recrystallization or other treatments for purification.

Now, a process for preparing the aromatic compounds having a trifluoromethyl group represented by the formula (3) wherein X is —OCO— will be described.

Among the aromatic compounds (3) having a trifluoromethyl group, those of the formula (3) wherein X is —OCO— can be produced by reacting the phenol compounds represented by the formula (27):

(wherein R$^1$, Y, Ar and k represent the same as defined before) with the optically active benzoic acid derivatives represented by the formula (28):

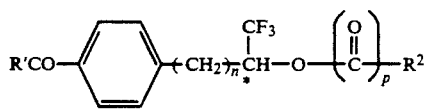

(wherein R', R$^2$, p and * mark denote the same as defined before, and n is an integer of 1 to 5) in the presence of a catalyst or a condensation agent.

Examples of the phenol compounds (27) usable in the above reaction are: 4-alkoxyphenol, 4-alkylphenol, 4-alkoxycarbonylphenol, 4-alkylcarbonyloxyphenol, 4'-alkoxy-4-hydroxybiphenyl, 4'-alkyl-4-hydroxybiphenyl, 4'-alkoxycarbonyl-4-hydroxybiphenyl, 4'-alkylcarbonyloxy-4-hydroxybiphenyl, 2-(4-hydroxyphenyl)-5-alkoxypyrimidine, 2-(4-hydroxyphenyl)-5-alkylpyrimidine, 2-(4-hydroxyphenyl)-5-alkoxycarbonylpyrimidine, and 2-(4-hydroxyphenyl)-5-alkylcarbonyloxypyrimidine.

The "alkyl" or "alkoxy" in the above-shown phenol compound signifies the presence of an alkyl group R$^1$ having 3 to 20 carbon atoms. Examples of such alkyl group are those mentioned before.

As examples of the optically active benzoic acid derivatives represented by the formula (28) and usable in the above reaction, there can be cited 4-(2-alkoxy-3,3,3-trifluoropropyl)benzoic acid, 4-(3-alkoxy-4,4,4-trifluorobutyl)benzoic acid, 4-(4-alkoxy-5,5,5-trifluoropentyl)benzoic acid, 4-(5-alkoxy-6,6,6-trifluorohexyl)benzoic acid, and 4-(6-alkoxy-7,7,7-trifluoroheptyl)benzoic acid.

It is also possible to use the compounds in which "alkoxyalkoxy", "alkylcarbonyloxy" or "alkoxyalkylcarbonyloxy" has been introduced in place of "alkoxy" in the above-mentioned compounds.

These carboxylic acids can be also used as an acid halide such as acid chloride or acid bromide in execution of the reaction.

The "alkoxy", "alkoxyalkoxy", "alkylcarbonyloxy" and "alkoxyalkylcarbonyloxy" in the above-mentioned compounds correspond to

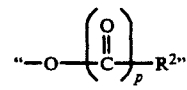

in the formula (28) where R$^2$ is an alkyl or alkoxyalkyl group having 1 to 20 carbon atoms. Such an alkyl or alkoxyalkyl group may be of either straight-chain or branched chain structure. In the latter case, it may be an optical active group.

Examples of said alkyl or alkoxyalkyl group are such as mentioned before.

The reaction between a phenol compound (27) and an optically active benzoic acid derivative (28) can be performed in the same way as in the above-described preparation process of the optically active aromatic compounds of the formula (3) (wherein X is —COO—) having a trifluoromethyl group.

For effective use of an optically active benzoic acid derivative which is relatively costly, it is advisable to use the other starting material phenol compound (27) in an excess amount, usually in an amount of 1 to 4 equivalents, preferably 1 to 2 equivalents to said benzoic acid derivative.

In case the optically active benzoic acid derivative represented by the formula (28) is a carboxylic acid, a carbodiimide is preferably used as in the case of the optically active aromatic compounds of the formula (3) (where X is —COO—), and the similar reaction conditions can be applied.

An optically active benzoic acid derivative (28) used as a starting material can be prepared according to either of the following two methods.

(1) When p in the formula (28) is 0:

An optically active benzoic acid derivative of the formula (28) wherein p is 0 can be prepared by oxydizing, in the presence of water, an optically active acetophenon derivative of the formula (25) obtained in the above-described process (3) for the preparation of optically active phenol derivatives (3). In this reaction, there is used an oxidizing agent capable of oxidizing an acetyl group to form a carboxylic acid. As such an oxidizing agent, there can be used potassium bichromate, sodium bichromate, potassium permanganese, sodium permanganese, potassium hypochlorite, sodium hydrochlorite, potassium hypobromide, sodium hypobromide and the like. Said oxidizing agent is used in an amount not less than one equivalent to the optically active acetophenone derivative (25). The upper limit of the usable amount of said oxidizing agent is not specifically restricted but preferably not greater than 10 equivalents to said acetophenone derivative (25).

In this reaction, an organic solvent may be used in addition to water. The solvent used here is the one which is inert to the oxidation reaction, such as dioxane, tetrahydrofuran, N-methylpyrrolidone and the like.

Reaction temperature is usually in the range from −20° C. to 130° C., preferably from −10° C. to 100° C.

Reaction time is not specifically defined. Usually, disappearance of the optically active acetophenone derivative (25) from the reaction system signals the end of the reaction.

After the reaction, the reaction product is subjected to the ordinary after-treatments such as acid-precipitation, extraction, liquid separation, etc., to obtain a desired optically active benzoic acid derivative of the formula (28) wherein p is 0.

The optically active benzoic acid derivative of the formula (28) (p=0) obtained here is a compound of the formula (28) wherein R' is a hydroxyl group. If desired, this compound can be turned into a compound of the formula (28) wherein R' is a halogen atom by introducing an acid halide in a known way.

(2) When p is 1:

An optically active benzoic acid derivative of the formula (28) wherein p is 1 can be prepared according to the following process by using as starting material an optically active alcohol compound (24) which is the same as used in the above-described preparation process (3) for the optically active phenol derivatives (3).

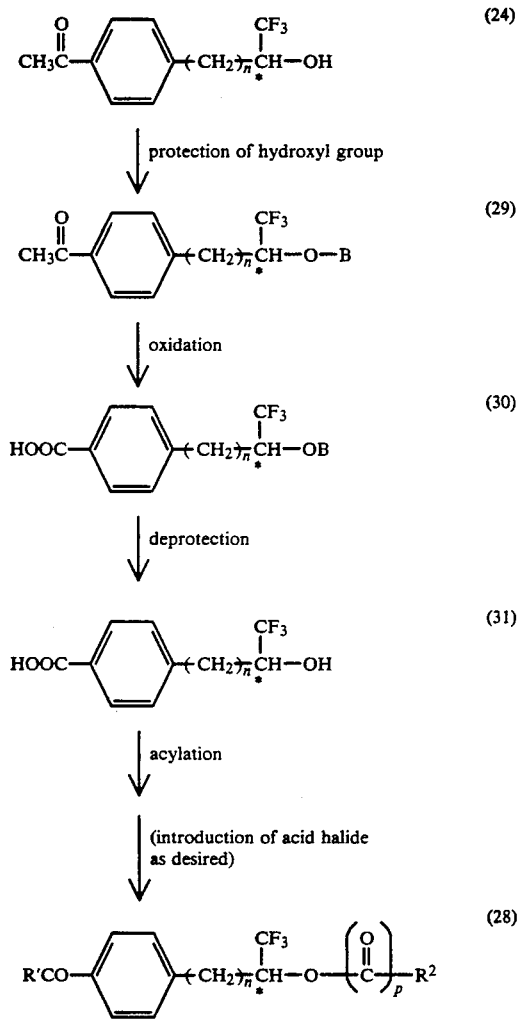

(In the above reaction formulae, R', R², n and * mark denote the same as defined above, and B is a protective group for hydroxyl group.)

The above process will be described in detail stepwise below.

The optically active acetophenone derivatives of the formula (29) can be prepared by protecting the hydroxyl group of formula (29) can be prepared by protecting the hydroxyl group of the optically active alcohol compounds (24). The protective group introducing reaction is executed by reacting an optically active alcohol compound (24) with a protectant of the hydroxyl group in the presence of a catalyst.

As examples of the protective group for the hydroxyl group, there can be cited alkyl or aralkyl groups such as methyl group, benzyl group and trityl group, alkoxyalkyl groups such as methoxymethyl group, methoxyethoxymethyl group, ethoxyethyl group, tetrahydrofuryl group and tetrahydropyranyl group, and silyl groups such as trimethylsilyl group and t-butyldimethylsilyl group.

As for the catalyst used in the reaction, although it depends on the kind of the protectant used, a basic substance is preferably used when the protective group for the hydroxyl group is alkyl, aralkyl or certain of alkoxyalkyl groups. As such a basic substance, there can be used organic or inorganic basic substances such as sodium hydroxide, potassium hydroxide, sodium carbonate, potassium carbonate, sodium hydrogencarbonate, potassium hydrogencarbonate, sodium methylate, sodium ethylate, sodium hydride, potassium hydride, n-butyl lithium and sec-butyl lithium.

Examples of the protectant usable here are methyl iodide, methyl bromide, benzyl chloride, benzyl bromide, triethyl chloride, chloromethyl methyl ether, chloromethyl methoxyethoxy ether and the like.

The amounts of said protectant and catalyst used in the reaction are variable depending on the type of the protectant used, but usually the protectant is used in an amount of 1 to 5 equivalents and the catalyst in an amount of 1 to 4 equivalents to the optically active alcohol compound (24) used as starting material.

This reaction is usually carried out in the presence of a catalyst. The catalyst is selected from those which are inert to the reaction, for example, ethers, halogenated hydrocarbons, esters and aprotic polar solvents, such as ethyl ether, tetrahydrofuran, dioxane, acetone, methyl ethyl ketone, toluene, benzene, chlorobenzene, dichloromethane, 1,2-dichloroethane, chloroform, carbon tetrachloride, ethyl acetate, dimetylformamide, dimethyl sulfoxide, hexamethylphosphoric triamide, acetonitrile, hexane and heptane. These solvents may be used either singly or in combination. No particular restrictions are imposed on the amount of the solvent used.

Reaction temperature is variable depending on the type of the protectant used, but usually it is in the range from −20° C. to 150° C.

Reaction time is not specifically defined. Disappearance of the starting optically active alcohol compound (24) from the reaction system can be taken as signaling the end of the reaction.

In case the protective group for the hydroxyl group is an alkoxyalkyl group, an acidic substance is preferably used as catalyst. As such an acidic substance, there can be used organic and inorganic acidic substances such as benzenesulfonic acid, p-toluenesulfonic acid, methanesulfonic acid, sulfuric acid, potassium hydrogen-sulfate, hydrochloric acid, phosphoric acid, acetic acid and ammonium chloride.

Examples of the protectant usable here are dimethoxymethane, ethylvinyl ether, dihydrofuran, dihydropyran and the like.

The amounts of said protectant and catalyst used here are not always specified as they are variable depending on the type of the protectant used, but usually the protectant is used in an amount of 1 to 5 equivalents and the catalyst in an amount of 0.005 to 1 equivalent to the optically active alcohol compound (24) used as starting material.

The reaction solvent, reaction temperature and reaction time correspond with those in the above-described protective group introducing reaction using a basic substance as catalyst.

When the protective group for the hydroxyl group is a silyl group, a basic substance is preferably used as catalyst. As such a basic substance, there can be used organic and inorganic basic substances such as sodium hydroxide, potassium hydroxide, sodium carbonate, potassium carbonate, sodium hydrogencarbonate, potassium hydrogencarbonate, sodium methylate, sodium ethylate, sodium hydride, potassium hydride, n-butyl lithium, sec-butyl lithium, imidazole, pyridine, and 4-dimethylaminopyridine.

Examples of the protectant used here are trimethylsilyl chloride, trimethylsilyl bromide, and t-butyldimethylsilyl chloride.

The amounts of said protectant and catalyst are variable depending on the type of the protectant used, but usually the protectant is used in an amount of 1 to 5 equivalents and the catalyst in an amount of 1 to 4 equivalents to the starting optical active alcohol compound (24).

The reaction solvent, reaction temperature and reaction time may be equal to those used in the protective group introducing reaction using a basic substance as catalyst.

Isolation of the thus prepared optically active acetophenone (29) from the reaction mixture can be accomplished by subjecting the reaction mixture to the ordinary after-treatments such as extraction, liquid separation, concentration, etc.

The optically active benzoic acids represented by the formula (30) can be produced by oxidizing said optically active acetophenone derivatives (29) in the presence of water. This oxidation reaction is identical with that performed in the previously described process (1) for the preparation of optically active benzoic acid derivatives (28). That is, an optically active acetophenone (29) is oxidized with an oxidizing agent having the ability to turn the acetyl group into a carboxylic acid in the presence of water to thereby form an optically active benzoic acid (30).

Isolation of said optically active benzoic acid (30) from the reaction mixture can be attained by conducting the ordinary after-treatments such as filtration, acid-precipitation, extraction, liquid separation, concentration, etc.

The optically active hydroxybenzoic acids of the formula (31) can be obtained by neutralizing the protective group of the hydroxyl group of the optically active benzoic acids (30) by using a deprotecting agent.

The deprotecting reaction varies in its scheme depending on the kind of the protective group B of the hydroxyl group in the compound of the formula (30). The reaction schemes are described below.

In case the protective group B of the hydroxyl group is an alkyl or aralkyl group, a Lewis acid is preferably used as deprotecting agent. As such a Lewis acid, there can be used phosphorus tribromide, boron trifluoride, aluminum chloride and the like. The amount of the Lewis acid used for said purpose is usually 1 to 5 equivalents to the optically active benzoic acid (30) used as starting material.

This reaction is usually carried out in a solvent. The solvent is selected from those which are inert to the reaction, for example, hydrocarbons or halogenated hydrocarbons such as benzene, toluene, hexane, heptane, dichloromethane, 1,2-dichloroethane and chloroform. These solvents may be used either singly or in combination. The amount of the solvent used for the reaction is not specifically defined.

Reaction temperature is usually in the range from −20° C. to 150° C.

Reaction time is not particularly restricted. Disappearance of the starting optically active benzoic acid (30) from the reaction system may be regarded as indicating the end of the reaction.

In case the protective group B of the hydroxyl group is an aralkyl group, especially a benzyl or trityl group, deprotection can be accomplished by performing catalytic hydrogenation in the presence of a hydrogenation catalyst.

A transition-metal catalyst is preferably used as hydrogenation catalyst in said catalytic hydrogenation reaction. As such a transition-metal catalyst, there can be used, for example, platinum type catalysts such as platinum oxide and Pt-C, palladium type catalysts such as Pd-C, Pd-BaSO$_4$ and palladium black, rhodium type catalysts such as Rh-C and Rh-Al$_2$O$_3$, ruthenium type catalysts such as ruthenium oxide and Ru-C, and nickel type catalysts such as Raney nickel. Among them, palladium type catalysts are especially preferred.

The amount of the hydrogenation catalyst used in the reaction is in the range of usually 0.01 to 100% by weight, preferably 0.1 to 50% by weight, based on the starting optically active benzoic acid (30).

The reaction solvent is selected from those inert to the reaction, which include alcohols such as methanol and ethanol, ethers such as dioxane and tetrahydrofuran, aromatic hydrocarbons such as benzene and toluene, aliphatic hydrocarbons such as hexane and cyclohexane, aprotic polar solvents such as dimethylformamide, fatty acids such as acetic acid, and water. These solvents may be used either singly or in combination. No specific restrictions are placed on the amount of the solvent used in the reaction.

Hydrogen pressure applied in the reaction is usually in the range of 1 to 200 atm.

Reaction temperature is in the range of usually 0° to 200° C., preferably 20° to 180° C.

Reaction time is not specifically defined. Disappearance of the starting optically active benzoic acid (30) from the reaction system or cessation of hydrogen absorption may be taken as signalying the end of the reaction.

Described in the following is the deprotection method in case the protective group B of the hydroxyl group is an alkoxyalkyl or silyl group.

In this case, an acid catalyst is preferably used as deprotecting agent. As such an acid catalyst, there can be used organic and inorganic acidic substances such as benzenesulfonic acid, p-toluenesulfonic acid, methanesulfonic acid, sulfuric acid, potassium hydrogensulfate, hydrochloric acid, phosphoric acid, acetic acid, trifluoroacetic acid and the like.

The amount of the acid catalyst used for said purpose in the reaction is usually in the range of 0.001 to 1 equivalent to the reactant optically active benzoic acid (30).

For the practice of this invention, presence of a protonic solvent such as water, methanol or ethanol in the reaction system is necessary.

As the reaction solvent, beside said protonic solvents which can be used singly or in admixture, it is also possible to use the following solvents singly or in admixture jointly with said protonic solvents: dioxane, tetrahydrofuran, acetone, acetonitrile, dimethylformamide, ethyl acetate, benzene, toluene, hexane, heptane, dichloromethane, 1,2-dichloroethane, chloroform and the like.

Reaction temperature is usually in the range from −20° C. to 150° C.

Reaction time is not specifically defined. The moment of disappearance of the starting optically active benzoic acid (30) may be regarded as the end point of the reaction.

Especially when the protective group B of the hydroxyl group is a silyl group, the deprotection reaction can be performed in the presence of fluoride ions.

Tetrabutylammonium fluoride, hydrogen fluoride, lithium tetrafluoroborate and the like can be cited as the sources of generation of fluorine ions used in the above reaction. The amount of such fluorine ions used in the reaction is usually in the range of 1 to 5 equivalents to the starting optically active benzoic acid (30).

As reaction solvent, there are used those which are inert to the reaction, for examples, ethers, ketones, esters, aprotic polar solvents, hydrocarbons and halogenated hydrocarbons, such as dioxane, tetrahydrofuran, acetone, acetonitrile, dimethylformamide, ethyl acetate, benzene, toluene, hexane, heptane, dichloromethane, 1,2-dichloroethane, and chloroform. These solvents may be used either singly or in combination. The amount of the solvent used in the reaction is not specifically restricted.

Reaction temperature is usually in the range of −20° C. to 150° C.

Reaction time is not specifically defined. Disappearance of the starting optically active benzoic acid (30) from the reaction system may be taken as the sign of the end of the reaction.

Isolation of the thus obtained optically active hydroxybenzoic acid (31) from the reaction mixture can be attained by conducting the ordinary after-treatments such as extraction, liquid separation, concentration, etc., on the reaction mixture.

An optically active benzoic acid derivative of the formula (28) (wherein p = 1), which is the objective compound, can be produced by reacting said optically active hydroxybenzoic acid (31) with an acid halide or acid anhydride represented by the formula (32):

$$R^2COR^5 \qquad (32)$$

(wherein $R^2$ is as defined above, and $R^5$ represents a halogen atom or $R^2COO$).

The substituent $R^2$ in said acid halide or acid anhydride of the formula (32) may be such as those referred to previously.

It is possible to apply an ordinary esterification method in this reaction, and the reaction can be performed by using a catalyst in the presence or absence of a solvent.

Organic or inorganic basic substances such as dimethylaminopyridine, tri-n-butylamine, pyridine, lysine, imidazole, sodium carbonate, sodium methylate, potassium hydrogencarbonate and the like can be used as catalyst in this reaction.

It is also possible to use an organic or inorganic acid such as toluenesulfonic acid, methanesulfonic acid, sulfuric acid, etc., as catalyst in the above reaction.

The amount of the catalyst used in the reaction is not specified as it may vary depending on the kind of the starting materials used, their combination with the catalyst used and other factors, but in case of using, for instance, a basic substance as catalyst, it is used in an amount usually not less than one equivalent to the acid halide or acid anhydride (32).

The amount of the acid halide or acid anhydride (32) used in the reaction is in the range of usually 1 to 4 equivalents, preferably 1 to 2 equivalents to the optically active hydroxybenzoic acid (31) used as starting compound.

In the case of using a solvent in this reaction, such a solvent is selected from those which are inert to the reaction, for example, aliphatic or aromatic hydrocarbons, ethers, halogenated hydrocarbons and organic amines, more specifically, tetrahydrofuran, ethyl ether, acetone, methyl ethyl ketone, toluene, benzene, chlorobenzene, dichloromethane, dichloroethane, chloroform, carbon tetrachloride, dimethylformamide, hexane, pyridine and the like. The amount of the solvent used in the reaction is not fixed definitely.

Reaction temperature is usually in the range from −30° C. to 100° C., preferably from −25° C. to 80° C. Reaction time is not specifically defined. The end of the reaction can be judged by disappearance of the starting optically active hydroxybenzoic acid (31) from the reaction system.

The reaction product is subjected to the ordinary after-treatments such as acidification, extraction, liquid separation, etc., to obtain an objective optically active benzoic acid derivative of the formula (28) wherein p is 1.

The thus obtained optically active benzoic acid derivative of the formula (28) (p = 1) is a compound of the formula (28) wherein R' is a hydroxyl group. If desired, this compound can be turned into a compound of the formula (28) wherein R' is a halogen atom by introducing an acid halide in a known way.

Listed below are the examples of the optically active aromatic compounds (3) having a trifluoromethyl group obtained according to the above-described process of this invention.

(a) Compounds wherein X is —COO—.

4-[1-alkyl($C_{1-20}$)oxy-2,2,2-trifluoroethyl]phenyl 4-alkyl($C_{3-20}$)oxybenzoate,
4-[2-alkyl($C_{1-20}$)oxy-3,3,3-trifluoropropyl]phenyl 4-alkyl($C_{3-20}$))oxybenzoate,
4-[3-alkyl($C_{1-20}$)oxy-4,4,4-trifluorobutyl]phenyl 4-alkyl($C_{3-20}$)oxybenzoate,
4-[4-alkyl($C_{1-20}$)oxy-5,5,5-trifluoropentyl]phenyl 4-alkyl($C_{3-20}$)oxybenzoate,
4-[5-alkyl($C_{1-20}$)oxy-6,6,6-trifluorohexyl]phenyl 4-alkyl($C_{3-20}$)oxybenzoate,
4-[6-alkyl($C_{1-20}$)oxy-7,7,7-trifluoroheptyl]phenyl 4-alkyl($C_{3-20}$)oxybenzoate,
4-[1-alkyl($C_{1-20}$)oxy-2,2,2-trifluoroethyl]phenyl 4-alkyl($C_{3-20}$)benzoate,
4-[2-alkyl($C_{1-20}$)oxy-3,3,3-trifluoropropyl]phenyl 4-alkyl($C_{3-20}$)benzoate,
4-[3-alkyl($C_{1-20}$)oxy-4,4,4-trifluorobutyl]phenyl 4-alkyl($C_{3-20}$)benzoate,
4-[4-alkyl($C_{1-20}$)oxy-5,5,5-trifluoropentyl]phenyl 4-alkyl($C_{3-20}$)benzoate,
4-[5-alkyl($C_{1-20}$)oxy-6,6,6-trifluorohexyl]phenyl 4-alkyl($C_{3-20}$)benzoate,
4-[6-alkyl($C_{1-20}$)oxy-7,7,7-trifluoroheptyl]phenyl 4-alkyl($C_{3-20}$)benzoate, 4-[1-alkyl($C_{1-20}$)oxy-2,2,2-trifluoroethyl]phenyl alkyl($C_{3-20}$)oxycarbonylbenzoate,
4-[2-alkyl($C_{1-20}$)oxy-3,3,3-trifluoropropyl]phenyl alkyl($C_{3-20}$)oxycarbonylbenzoate,
4-[3-alkyl($C_{1-20}$)oxy-4,4,4-trifluorobutyl]phenyl alkyl($C_{3-20}$)oxycarbonylbenzoate,
4-[4-alkyl($C_{1-20}$)-5,5,5-trifluoropentyl]phenyl alkyl($C_{3-20}$)oxycarbonylbenzoate,
4-[5-alkyl($C_{1-20}$)-6,6,6-trifluorohexyl]phenyl 4-alkyl($C_{3-20}$)oxycarbonylbenzoate,
4-[6-alkyl($C_{1-20}$)-7,7,7-trifluoroheptyl]phenyl 4-alkyl($C_{3-20}$)oxycarbonylbenzoate,
4-[1-alkyl($C_{1-20}$)oxy-2,2,2-trifluoroethyl]phenyl 4-alkyl($C_{3-20}$)carbonyloxybenzoate,
4-[2-alkyl($C_{1-20}$)oxy-3,3,3-trifluoropropyl]phenyl 4-alkyl($C_{3-20}$)carbonyloxybenzoate,
4-[3-alkyl($C_{1-20}$)oxy-4,4,4-trifluorobutyl]phenyl 4-alkyl($C_{3-20}$)carbonyloxybenzoate,
4-[4-alkyl($C_{1-20}$)oxy-5,5,5-trifluoropentyl]phenyl 4-alkyl($C_{3-20}$)carbonyloxybenzoate,
4-[5-alkyl($C_{1-20}$)oxy-6,6,6-trifluorohexyl]phenyl 4-alkyl($C_{3-20}$)carbonyloxybenzoate,
4-[6-alkyl($C_{1-20}$)oxy-7,7,7-trifluoroheptyl]phenyl 4-alkyl($C_{3-20}$)carbonyloxybenzoate,
4-[1-alkyl($C_{1-20}$)oxy-2,2,2-trifluoroethyl]phenyl 4'-alkyl($C_{3-20}$)oxy-4-biphenylcarboxylate,
4-[2-alkyl($C_{1-20}$)oxy-3,3,3-trifluoropropyl]phenyl 4'-alkyl($C_{3-20}$)oxy-4-biphenylcarboxylate,
4-[3-alkyl($C_{1-20}$)oxy-4,4,4-trifluorobutyl]phenyl 4'-alkyl($C_{3-20}$)oxy-4-biphenylcarboxylate,
4-[4-alkyl($C_{1-20}$)oxy-5,5,5-trifluoropentyl]phenyl 4'-alkyl($C_{3-20}$)oxy-4-biphenylcarboxylate,
4-[5-alkyl($C_{1-20}$)oxy-6,6,6-trifluorohexyl]phenyl 4'-alkyl($C_{3-20}$)oxy-4-biphenylcarboxylate,
4-(6-alkyl($C_{1-20}$)oxy-7,7,7-trifluoroheptyl]phenyl 4'-alkyl($C_{3-20}$)oxy-4-biphenylcarboxylate,
4-[1-alkyl($C_{1-20}$)oxy-2,2,2-trifluoroethyl]phenyl 4'-alkyl($C_{3-20}$)-4-biphenylcarboxylate,
4-[2-alkyl($C_{1-20}$)oxy-3,3,3-trifluoropropyl]phenyl 4'-alkyl($C_{3-20}$)-4-biphenylcarboxylate,
4-[3-alkyl($C_{1-20}$)oxy-4,4,4-trifluorobutyl]phenyl 4'-alkyl($C_{3-20}$)-4-biphenylcarboxylate,
4-[4-alkyl($C_{1-20}$)oxy-5,5,5-trifluoropentyl]phenyl 4'-alkyl($C_{3-20}$)-4-biphenylcarboxylate,
4-[5-alkyl($C_{1-20}$)oxy-6,6,6-trifluorohexyl]phenyl 4'-alkyl($C_{3-20}$)-4-biphenylcarboxylate,
4-[6-alkyl($C_{1-20}$)oxy-7,7,7-trifluoroheptyl]phenyl 4'-alkyl($C_{3-20}$)-4-biphenylcarboxylate,
4-[1-alkyl($C_{1-20}$)oxy-2,2,2-trifluoroethyl]phenyl 4'-alkyl($C_{3-20}$)oxycarbonyl-4-biphenylcarboxylate,
4-[2-alkyl($C_{1-20}$)oxy-3,3,3-trifluoropropyl]phenyl 4'-alkyl($C_{3-20}$)oxycarbonyl-4-biphenylcarboxylate,
4-[3-alkyl($C_{1-20}$)oxy-4,4,4-trifluorobutyl]phenyl 4'-alkyl($C_{3-20}$)oxycarbonyl-4-biphenylcarboxylate,
4-[4-alkyl($C_{1-20}$)oxy-5,5,5-trifluoropentyl]phenyl 4'-alkyl($C_{3-20}$)oxycarbonyl-4-biphenylcarboxylate,
4-[5-alkyl($C_{1-20}$)oxy-6,6,6-trifluorohexyl]phenyl 4'-alkyl($C_{3-20}$)oxycarbonyl-4-biphenylcarboxylate,
4-[6-alkyl($C_{1-20}$)oxy-7,7,7-trifluoroheptyl]phenyl 4'-alkyl($C_{3-20}$)oxycarbonyl-4-biphenylcarboxylate,
4-[1-alkyl($C_{1-20}$)oxy-2,2,2-trifluoroethyl]phenyl 4'-alkyl($C_{3-20}$)carbonyloxy-4-biphenylcarboxylate,
4-[2-alkyl($C_{1-20}$)oxy-3,3,3-trifluoropropyl]phenyl 4'-alkyl($C_{3-20}$)carbonyloxy-4-biphenylcarboxylate,
4-[3-alkyl($C_{1-20}$)oxy-4,4,4-trifluorobutyl]phenyl 4'-alkyl($C_{3-20}$)carbonyloxy-4-biphenylcarboxylate,
4-[4-alkyl($C_{1-20}$)oxy-5,5,5-trifluoropentyl]phenyl 4'-alkyl($C_{3-20}$)carbonyloxy-4-biphenylcarboxylate,
4-[5-alkyl($C_{1-20}$)oxy-6,6,6-trifluorohexyl]phenyl 4'-alkyl($C_{3-20}$)carbonyloxy-4-biphenylcarboxylate,
4-[6-alkyl($C_{1-20}$)oxy-7,7,7-trifluoroheptyl]phenyl 4'-alkyl($C_{3-20}$)carbonyloxy-4-biphenylcarboxylate,
2-[4-[4-[1-alkyl($C_{1-20}$)oxy-2,2,2-trifluoroethylcarbonyl]phenyl]-5-alkyl($C_{3-20}$)oxypyrimidine,
2-[4-[4-[2-alkyl($C_{1-20}$)oxy-3,3,3-trifluoropropyl]phenoxycarbonyl]phenyl]-5-alkyl($C_{3-20}$)oxypyrimidine,
2-[4-[4-[3-alkyl($C_{1-20}$)oxy-4,4,4-trifluorobutyl]phenoxycarbonyl]phenyl]-5-alkyl($C_{3-20}$)oxypyrimidine,
2-[4-[4-[4-alkyl($C_{1-20}$)oxy-5,5,5-trifluoropentyl]phenoxycarbonyl]phenyl]-5-alkyl($C_{3-20}$)oxypyridimine,
2-[4-[4-[5-alkyl($C_{1-20}$)oxy-6,6,6-trifluorohexyl]phenoxycarbonyl]phenyl]-5-alkyl($C_{3-20}$)oxypyrimidine,
2-[4-[4-[6-alkyl($C_{1-20}$)oxy-7,7,7-trifluoroheptyl]phenoxycarbonyl]phenyl]-5-alkyl($C_{3-20}$)oxypyrimidine,
2-[4-[4-[1-alkyl($C_{1-20}$)oxy-2,2,2-trifluoroethyl]phenoxycarbonyl]phenyl]-5-alkyl($C_{3-20}$)pyrimidine,
2-[4-[4-[2-alkyl($C_{1-20}$)oxy-3,3,3-trifluoropropyl]phenoxycarbonyl]phenyl]-5-alkyl($C_{3-20}$)pyrimidine,
2-[4-[4-[3-alkyl($C_{1-20}$)oxy-4,4,4-trifluorobutyl]phenoxycarbonyl]phenyl]-5-alkyl($C_{3-20}$)pyrimidine,
2-[4-[4-[4-alkyl($C_{1-20}$)oxy-5,5,5-trifluoropentyl]phenoxycarbonyl]phenyl]-5-alkyl($C_{3-20}$)pyrimidine,
2-[4-[4-[5-alkyl($C_{1-20}$)oxy-6,6,6-trifluorohexyl]phenoxycarbonyl]phenyl]-5-alkyl($C_{3-20}$)pyrimidine,
2-[4-[4-[6-alkyl($C_{1-20}$)oxy-7,7,7-trifluoroheptyl]phenoxycarbonyl]phenyl]-5-alkyl($C_{3-20}$)pyrimidine,
2-[4-[4-[1-alkyl($C_{1-20}$)oxy-2,2,2-trifluoroethyl]phenoxycarbonyl]phenyl]-5-alkyl($C_{3-20}$)oxycarbonylpyrimidine,
2-[4-[4-[2-alkyl($C_{1-20}$)oxy-3,3,3-trifluoropropyl]phenoxycarbonyl]phenyl]-5-alkyl($C_{3-20}$)oxycarbonylpyrimide,
2-[4-[4-[3-alkyl($C_{1-20}$)oxy-4,4,4-trifluorobutyl]phenoxycarbonyl]phenyl-5-alkyl($C_{3-20}$)oxycarbonylpyrimidine,
2-[4-[4-[4-alkyl($C_{1-20}$)oxy-5,5,5-trifluoropenyl]phenoxycarbonyl]phenyl]-5-alkyl($C_{3-20}$)oxycarbonylpyrimidine,
2-[4-[4-[5-alkyl($C_{1-20}$)oxy-6,6,6-trifluorohexyl]phenoxycarbonyl]phenyl]-5-alkyl($C_{3-20}$)oxycarbonylpyridimine,
2-[4-[4-[6-alkyl($C_{1-20}$)oxy-7,7,7-trifluoroheptyl]phenoxycarbonyl]phenyl]-5-alkyl($C_{3-20}$)oxycarbonylpyrimidine,
2-[4-[4-[1-alkyl($C_{1-20}$)oxy-2,2,2-trifluoroethyl]phenoxycarbonyl]phenyl]-5-alkyl($C_{3-20}$)carbonyloxypyrimidine,
2-[4-[4-[2-alkyl($C_{1-20}$)oxy-3,3,3-trifluoropropyl]phenoxycarbonyl]phenyl]-5-alkyl($C_{3-20}$)carbonyloxypyrimidine,
2-[4-[4-[3-alkyl($C_{1-20}$)oxy-4,4,4-trifluorobutyl]phenoxycarbonyl]phenyl]-5-alkyl($C_{3-20}$)carbonyloxypyridimine,
2-[4-[4-[4-alkyl($C_{1-20}$)oxy-5,5,5-trifluoropentyl]phenoxycarbonyl]phenyl]-5-alkyl($C_{3-20}$)carbonyloxypyrimidine,
2-[4-[4-[5-alkyl($C_{1-20}$)oxy-6,6,6-trifluorohexyl]phenoxycarbonyl]phenyl]-5-alkyl($C_{3-20}$)carbonyloxypyrimidine,
2-[4-[4-[6-alkyl($C_{1-20}$)oxy-7,7,7-trifluoroheptyl]phenoxycarbonyl]phenyl]-5-alkyl($C_{3-20}$)carbonyloxypyrimidine,
4-[1-alkoxyalkyl($C_{2-20}$)oxy-2,2,2-trifluoroethyl]phenyl 4-alkyl($C_{3-20}$)oxybenzoate,
4-[2-alkoxyalkyl($C_{2-20}$)oxy-3,3,3-trifluoropropyl]phenyl 4-alkyl($C_{3-20}$)oxybenzoate, 4-[3-alkoxyalkyl($C_{2-20}$)oxy-4,4,4-trifluorobutyl]phenyl 4-alkyl($C_{3-20}$)oxybenzoate,
4-[4-alkoxyalkyl($C_{2-20}$)oxy-5,5,5-trifluoropentyl]phenyl 4-alkyl($C_{3-20}$)oxybenzoate,
4-[5-alkoxyalkyl($C_{2-20}$)oxy-6,6,6-trifluorohexyl]phenyl 4-alkyl($C_{3-20}$)oxybenzoate,
4-[6-alkoxyalkyl($C_{2-20}$)oxy-7,7,7-trifluoroheptyl]phenyl]4-alkyl($C_{3-20}$)oxybenzoate,
4-[1-alkoxyalkyl($C_{2-20}$)oxy-2,2,2-trifluoroethyl]phenyl 4-alkyl($C_{3-20}$)benzoate,
4-[2-alkoxyalkyl($C_{2-20}$)oxy-3,3,3-trifluoropropyl]phenyl 4-alkyl($C_{3-20}$)benzoate,
4-[3-alkoxyalkyl($C_{2-20}$)oxy-4,4,4-trifluorobutyl]phenyl 4-alkyl($C_{3-20}$)benzoate,
4-[4-alkoxyalkyl($C_{2-20}$)oxy-5,5-trifluoropentyl]phenyl 4-alkyl($C_{3-20}$)benzoate,
4-[5-alkoxyalkyl($C_{2-20}$)oxy-6,6,6-trifluorohexyl]phenyl 4-alkyl($C_{3-20}$)benzoate,
4-[6-alkoxyalkyl($C_{2-20}$)oxy-7,7,7-trifluoroheptyl]phenyl 4-alkyl($C_{3-20}$)benzoate,
4-[1-alkoxyalkyl($C_{2-20}$)oxy-2,2,2-trifluoroethyl]phenyl 4-alkyl($C_{3-20}$)oxycarbonylbenzoate,
4-[2-alkoxyalkyl($C_{2-20}$)oxy-3,3,3-trifluoropropyl]phenyl 4-alkyl($C_{3-20}$)oxycarbonylbenzoate,
4-[3-alkoxyalkyl($C_{2-20}$)oxy-4,4,4-trifluorobutyl]phenyl 4-alkyl($C_{3-20}$)oxycarbonylbenzoate,
4-[4-alkoxyalkyl($C_{2-20}$)oxy-5,5,5-trifluoropentyl]phenyl 4-alkyl($C_{3-20}$)oxycarbonylbenzoate,
4-[5-alkoxyalkyl($C_{2-20}$)oxy-6,6,6-trifluorohexyl]phenyl 4-alkyl($C_{3-20}$)oxycarbonylbenzoate,
4-[6-alkoxyalkyl($C_{2-20}$)oxy-7,7,7-trifluoroheptylphenyl 4-alkyl($C_{3-20}$)oxycarbonylbenzoate,
4-[1-alkoxyalkyl($C_{2-20}$)oxy-2,2,2-trifluoroethyl]phenyl 4-alkyl($C_{3-20}$)carbonyloxybenzoate,
4-[2-alkoxyalkyl($C_{2-20}$)oxy-3,3,3-trifluoropropyl]phenyl 4-alkyl($C_{3-20}$)carbonyloxybenzoate,
4-[3-alkoxyalkyl($C_{2-20}$)oxy-4,4,4-trifluorobutyl]phenyl 4-alkyl($C_{3-20}$)carbonyloxybenzoate,
4-[4-alkoxyalkyl($C_{2-20}$)oxy-5,5,5-trifluoropentyl]phenyl 4-alkyl($C_{3-20}$)carbonyloxybenzoate,
4-[5-alkoxyalkyl($C_{2-20}$)oxy-6,6,6-trifluorohexyl]phenyl 4-alkyl($C_{3-20}$)carbonyloxybenzoate,
4-[6-alkoxyalkyl($C_{2-20}$)oxy-7,7,7-trifluoroheptyl]phenyl 4-alkyl($C_{3-20}$)carbonyloxybenzoate,
4-[1-alkoxyalkyl($C_{2-20}$)oxy-2,2,2-trifluoroethyl]phenyl 4'-alkyl($C_{3-20}$)oxy-4-biphenylcarboxylate,
4-[2-alkoxyalkyl($C_{2-20}$)oxy-3,3,3-trifluoropropyl]phenyl 4'-alkyl($C_{3-20}$)oxy-4-biphenylcarboxylate,
4-[3-alkoxyalkyl($C_{2-20}$)oxy-4,4,4-trifluorobutyl]phenyl 4'-alkyl($C_{3-20}$)oxy-4-biphenylcarboxylate,
4-[4-alkoxyalkyl($C_{2-20}$)oxy-5,5,5-trifluoropentyl]phenyl 4'-alkyl($C_{3-20}$)oxy-4-biphenylcarboxylate,
4-[5-alkoxyalkyl($C_{2-20}$)oxy-6,6,6-trifluorohexyl]phenyl 4'-alkyl($C_{3-20}$)oxy-4-biphenylcarboxylate,
4-[6-alkoxyalkyl($C_{2-20}$)oxy-7,7,7-trifluoroheptyl]phenyl 4'-alkyl($C_{3-20}$)oxy-4-biphenylcarboxylate,
4-[1-alkoxyalkyl($C_{2-20}$)oxy-2,2,2-trifluoroethyl]phenyl 4'-alkyl($C_{3-20}$)-4-biphenylcarboxylate,
4-[2-alkoxyalkyl($C_{2-20}$)oxy-3,3,3-trifluoropropyl]phenyl 4'-alkyl($C_{3-20}$)-4-biphenylcarboxylate,
4-[3-alkoxyalkyl($C_{2-20}$)oxy-4,4,4-trifluorobutyl]phenyl 4'-alkyl($C_{3-20}$)-4-biphenylcarboxylate,
4-[4-alkoxyalkyl($C_{2-20}$)oxy-5,5,5-trifluoropentyl]phenyl 4'-alkyl($C_{3-20}$)-4-biphenylcarboxylate,
4-[5-alkoxyalkyl($C_{2-20}$)oxy-6,6,6-trifluorohexyl]phenyl 4'-alkyl($C_{3-20}$)-4-biphenylcarboxylate,
4-[6-alkoxyalkyl($C_{2-20}$)oxy-7,7,7-trifluoroheptyl]phenyl 4'-alkyl $C_{3-20}$)-4-biphenylcarboxylate,
4-[1-alkoxyalkyl($C_{2-20}$)oxy-2,2,2-trifluoroethyl]phenyl 4'-alkyl($C_{3-20}$)oxycarbonyl-4-biphenylcarboxylate,
4-[2-alkoxyalkyl($C_{2-20}$)oxy-3,3,3-trifluoropropyl]phenyl 4'-alkyl($C_{3-20}$)oxycarbonyl-4-biphenylcarboxylate,
4-[3-alkoxyalkyl($C_{2-20}$)oxy-4,4,4-trifluorobutyl]phenyl 4'-alkyl($C_{3-20}$)oxycarbonyl-4-biphenylcarboxylate,
4-[4-alkoxyalkyl($C_{2-20}$)oxy-5,5,5-trifluoropentyl]phenyl 4'-alkyl($C_{3-20}$)oxycarbonyl-4-biphenylcarboxylate,
4-[5-alkoxyalkyl($C_{2-20}$)oxy-6,6,6-trifluorohexyl]phenyl 4'-alkyl($C_{3-20}$)oxycarbonyl-4-biphenylcarboxylate,
4-[6-alkoxyalkyl($C_{2-20}$)oxy-7,7,7-trifluoroheptyl]phenyl 4'-alkyl($C_{3-20}$)oxycarbonyl-4-biphenylcarboxylate,
4-[1-alkoxyalkyl($C_{2-20}$)oxy-2,2,2-trifluoroethyl]phenyl 4'-alkyl($C_{3-20}$)carbonyloxy-4-biphenylcarboxylate,
4-[2-alkoxyalkyl($C_{2-20}$)oxy-3,3,3-trifluoropropyl]phenyl 4'-alkyl($C_{3-20}$)carbonyloxy-4-biphenylcarboxylate,
4-[3-alkoxyalkyl($C_{2-20}$)oxy-4,4,4-trifluorobutyl]phenyl 4'-alkyl($C_{3-20}$)carbonyloxy-4-biphenylcarboxylate,
4-[4-alkoxyalkyl($C_{2-20}$)oxy-5,5,5-trifluoropentyl]phenyl 4'-alkyl($C_{3-20}$)carbonyloxy-4-biphenylcarboxylate,
4-[5-alkoxyalkyl($C_{2-20}$)oxy-6,6,6-trifluorohexyl]phenyl 4'-alkyl($C_{3-20}$)carbonyloxy-4-biphenylcarboxylate,
4-[6-alkoxyalkyl($C_{2-20}$)oxy-7,7,7-trifluoroheptyl]phenyl 4'-alkyl($C_{3-20}$)carbonyloxy-4-biphenylcarboxylate,
2-[4-[4-[1-alkoxyalkyl($C_{2-20}$)oxy-2,2,2-trifluoroethyl]-phenoxycarbonyl]phenyl]-5-alkyl($C_{3-20}$)oxypyrimidine,
2-[4-[4-[2-alkoxyalkyl($C_{2-20}$)oxy-3,3,3-trifluoropropyl]-phenoxycarbonyl]phenyl]-5-alkyl($C_{3-20}$)oxypyrimidine,
2-[4-[4-[3-alkoxyalkyl($C_{2-20}$)oxy-4,4,4-trifluorobutyl]-phenoxycarbonyl]phenyl]-5-alkyl($C_{3-20}$)oxypyrimidine,
2-[4-[4-[4-alkoxyalkyl($C_{2-20}$)oxy-5,5,5-trifluoropentyl]-phenoxycarbonyl]phenyl]-5-alkyl($C_{3-20}$)oxypyrimidine,
2-[4-[4-[5-alkoxyalkyl($C_{2-20}$)oxy-6,6,6-trifluorohexyl]-phenoxycarbonyl]phenyl]-5-alkyl($C_{3-20}$)oxypyrimidine,
2-[4-[4-[6-alkoxyalkyl($C_{2-20}$)oxy-7,7,7-trifluoroheptyl]-phenoxycarbonyl]phenyl-5-alkyl($C_{3-20}$)oxypyrimidine,
2-[4-[4-[1-alkoxyalkyl($C_{2-20}$)oxy-2,2,2-trifluoroethyl]-phenoxycarbonyl]phenyl]-5-alkyl($C_{3-20}$)pyrimidine,
2-[4-[4-[2-alkoxyalkyl($C_{2-20}$)oxy-3,3,3-trifluoropropyl]-phenoxycarbonyl]phenyl]-5-alkyl($C_{3-20}$)pyrimidine,
2-[4-[4-[3-alkoxyalkyl($C_{2-20}$)oxy-4,4,4-trifluorobutyl]-phenoxycarbonyl]phenyl-5-alkyl($C_{3-20}$)pyrimidine,
2-[4-[4-[4-alkoxyalkyl($C_{2-20}$)oxy-5,5,5-trifluoropentyl]-phenoxycarbonyl]phenyl]-5-alkyl($C_{3-20}$)pyrimidine,
2-[4-[4-[5-alkoxyalkyl($C_{2-20}$)oxy-6,6,6-trifluorohexyl]-phenoxycarbonyl]phenyl]-5-alkyl($C_{3-20}$)pyrimidine,
2-[4-[4-[6-alkoxyalkyl($C_{2-20}$)oxy-7,7,7-trifluoroheptyl]-phenoxycarbonyl]phenyl]-5-alkyl($C_{3-20}$)pyrimidine,
2-[4-[4-[1-alkoxyalkyl($C_{2-20}$)oxy-2,2,2-trifluoroethyl]-phenoxycarbonyl]phenyl]-5-alkyl($C_{3-20}$)oxycarbonylpyrimidine,
2-[4-[4-[2-alkoxyalkyl($C_{2-20}$)oxy-3,3,3-trifluoropropyl]-phenoxycarbonyl]phenyl]-5-alkyl($C_{3-20}$)oxycarbonylpyrimidine,
2-[4-[4-[3-alkoxyalkyl($C_{2-20}$)oxy-4,4,4-trifluorobutyl]-phenoxycarbonyl]phenyl]-5-alkyl($C_{3-20}$)oxycarbonylpyrimidine,
2-[4-[4-[4-alkoxyalkyl($C_{2-20}$)oxy-5,5,5-trifluoropentyl]-phenoxycarbonyl]phenyl]-5-alkyl($C_{3-20}$)oxycarbonylpyrimidine, 2-[4-[4-[5-alkoxyalkyl($C_{2-20}$)oxy-6,6,6-trifluorohexyl]]-phenoxycarbonyl]phenyl]-5-alkyl($C_{3-20}$)oxycarbonylpyrimidine, 2-[4-[4-[6-alkoxyalkyl($C_{2-20}$)oxy-7,7,7-trifluoroheptyl]-phenoxycarbonyl]phenyl]-5-alkyl($C_{3-20}$)oxycarbonylpyridimine, 2-[4-[4-[1-alkoxyalkyl($C_{2-20}$)oxy-2,2,2-trifluoroethyl]-phenoxycarbonyl]phenyl]-5-alkyl($C_{3-20}$)carbonyloxypyrimidine, 2-[4-[4-[2-alkoxyalkyl($C_{2-20}$)oxy-3,3,3-trifluoropropyl]-phenoxycarbonyl]phenyl]-5-alkyl($C_{3-20}$)carbonyloxypyrimidine, 2-[4-[4-[3-alkoxyalkyl($C_{2-20}$)oxy-4,4,4-trifluorobutyl]-phenoxycarbonyl]phenyl]-5-alkyl($C_{3-20}$)carbonyloxypyrimidine, 2-[4-[4-[4-alkoxyalkyl($C_{2-20}$)oxy-5,5,5-trifluoropentyl]-phenoxycarbonyl]phenyl]-5-alkyl($C_{3-20}$)carbonyloxypyrimidine, 2-[4-[4-[5-alkoxyalkyl($C_{2-20}$)oxy-6,6,6-trifluorohexyl]-phenoxycarbonyl]phenyl]-5-alkyl($C_{3-20}$)carbonyloxypyrimidine, 2-[4-[4-[6-alkoxyalkyl($C_{2-20}$)oxy-7,7,7-trifluoroheptyl]-phenoxycarbonyl]phenyl-5-alkyl($C_{3-20}$)carbonyloxypyrimidine, 4-[1-alkyl($C_{1-20}$)carbonyloxy-2,2,2-trifluoroethyl]phenyl 4-alkyl($C_{3-20}$)oxybenzoate, 4-[2-alkyl($C_{1-20}$)carbonyloxy-3,3,3-trifluoropropyl]phenyl 4-alkyl($C_{3-20}$)oxybenzoate, 4-[3-alkyl($C_{1-20}$)carbonyloxy-4,4,4-trifluorobutyl]phenyl 4-alkyl($C_{3-20}$)oxybenzoate, 4-[4-alkyl($C_{1-20}$))carbonyloxy-5,5,5-trifluoropentyl]phenyl 4-alkyl($C_{3-20}$)oxybenzoate, 4-[5-alkyl($C_{1-20}$)carbonyloxy-6,6,6-trifluorohexyl]phenyl 4-alkyl($C_{3-20}$)oxybenzoate, 4-[6-alkyl($C_{1-20}$)carbonyloxy-7,7,7-trifluoroheptyl]phenyl 4-alkyl($C_{3-20}$)oxybenzoate, 4-[1-alkyl($C_{1-20}$)carbonyloxy-2,2,2-trifluoroethyl]phenyl 4-alkyl($C_{3-20}$)benzoate, 4-[2-alkyl($C_{1-20}$)carbonyloxy-3,3,3-trifluoropropyl]phenyl 4-alkyl($C_{3-20}$)benzoate, 4-[3-alkyl($C_{1-20}$)carbonyloxy-4,4,4-trifluorobutyl]phenyl 4-alkyl($C_{3-20}$)benzoate, 4-[4-alkyl($C_{1-20}$)carbonyloxy-5,5,5-trifluoropentyl]phenyl 4-alkyl($C_{3-20}$)benzoate, 4-[5-alkyl($C_{1-20}$)carbonyloxy-6,6,6-trifluorohexyl]phenyl 4-alkyl($C_{3-20}$)benzoate, 4-[6-alkyl($C_{1-20}$)carbonyloxy-7,7,7-trifluoroheptyl]phenyl 4-alkyl($C_{3-20}$)benzoate, 4-[1-alkyl($C_{1-20}$)carbonyloxy-2,2,2-trifluoroethyl]phenyl 4-alkyl($C_{3-20}$)oxycarbonylbenzoate, 4-[2-alkyl($C_{1-20}$)carbonyloxy-3,3,3-trifluoropropyl]phenyl 4-alkyl($C_{3-20}$)oxycarbonylbenzoate, 4-[3-alkyl($C_{1-20}$)carbonyloxy-4,4,4-trifluorobutyl]phenyl 4-alkyl($C_{3-20}$)oxycarbonylbenzoate, 4-[4-alkyl($C_{1-20}$)carbonyloxy-5,5,5-trifluoropentyl]phenyl 4-alkyl($C_{3-20}$)oxycarbonylbenzoate, 4-[5-alkyl($C_{1-20}$)carbonyloxy-6,6,6-trifluorohexyl]phenyl 4-alkyl($C_{3-20}$)oxycarbonylbenzoate, 4-[6-alkyl($C_{1-20}$)carbonyloxy-7,7,7-trifluoroheptyl]phenyl 4-alkyl($C_{3-20}$)oxycarbonylbenzoate, 4-[1-alkyl($C_{1-20}$)carbonyloxy-2,2,2-trifluoroethyl]phenyl 4-alkyl($C_{3-20}$)carbonyloxybenzoate, 4-[2-alkyl($C_{1-20}$)carbonyloxy-3,3,3-trifluoropropyl]phenyl 4-alkyl($C_{3-20}$)carbonyloxybenzoate, 4-[3-alkyl($C_{1-20}$)carbonyloxy-4,4,4-trifluorobutyl]phenyl 4-alkyl($C_{3-20}$)carbonyloxybenzoate, 4-[4-alkyl($C_{1-20}$)carbonyloxy-5,5,5-trifluoropentyl]phenyl 4-alkyl($C_{3-20}$)carbonyloxybenzoate, 4-[5-alkyl($C_{1-20}$)carbonyloxy-6,6,6-trifluorohexyl]phenyl 4-alkyl($C_{3-20}$)carbonyloxybenzoate, 4-[6-alkyl($C_{1-20}$)carbonyloxy-7,7,7-trifluoroheptyl]phenyl 4-alkyl($C_{3-20}$)carbonyloxybenzoate, 4-[1-alkyl($C_{1-20}$)carbonyloxy-2,2,2-trifluoroethyl]phenyl 4'-alkyl($C_{3-20}$)oxy-4-biphenylcarboxylate, 4-[2-alkyl($C_{1-20}$)carbonyloxy-3,3,3-trifluoropropyl]phenyl 4'-alkyl($C_{3-20}$)oxy-4-biphenylcarboxylate, 4-[3-alkyl($C_{1-20}$)carbonyloxy-4,4,4-trifluorobutyl]phenyl 4'-alkyl($C_{3-20}$)oxy-4-biphenylcarboxylate, 4-[4-alkyl($C_{1-20}$)carbonyloxy-5,5,5-trifluoropentyl]phenyl 4'-alkyl($C_{3-20}$)oxy-4-biphenylcarboxylate, 4-[5-alkyl($C_{1-20}$)carbonyloxy-6,6,6-trifluorohexyl]phenyl 4'-alkyl($C_{3-20}$)oxy-4-biphenylcarboxylate, 4-[6-alkyl($C_{1-20}$)carbonyloxy-7,7,7-trifluoroheptyl]phenyl 4'-alkyl($C_{3-20}$)oxy-4-biphenylcarboxylate, 4-[1-alkyl($C_{1-20}$)carbonyloxy-2,2,2-trifluoroethyl]phenyl 4'-alkyl($C_{3-20}$)-4-biphenylcarboxylate, 4-[2-alkyl($C_{1-20}$)carbonyloxy-3,3,3-trifluoropropyl]phenyl 4'-alkyl($C_{3-20}$)-4-biphenylcarboxylate, 4-[3-alkyl($C_{1-20}$)carbonyloxy-4,4,4-trifluorobutyl]phenyl 4'-alkyl($C_{3-20}$)-4-biphenylcarboxylate, 4-[4-alkyl($C_{1-20}$)carbonyloxy-5,5,5-trifluoropentyl]phenyl 4'-alkyl($C_{3-20}$)-4-biphenylcarboxylate, 4-[5-alkyl($C_{1-20}$)carbonyloxy-6,6,6-trifluorohexyl]phenyl 4'-alkyl($C_{3-20}$)-4-biphenylcarboxylate, 4-[6-alkyl($C_{1-20}$)carbonyloxy-7,7,7-trifluoroheptyl]phenyl 4'-alkyl($C_{3-20}$)-4-biphenylcarboxylate, 4-[1-alkyl($C_{1-20}$)carbonyloxy-2,2,2-trifluoroethyl]phenyl 4'-alkyl($C_{3-20}$)oxycarbonyl-4-biphenylcarboxylate, 4-[2-alkyl($C_{1-20}$)carbonyloxy-3,3,3-trifluoropropyl]phenyl 4'-alkyl($C_{3-20}$)oxycarbonyl-4-biphenylcarboxylate, 4-[3-alkyl($C_{1-20}$)carbonyloxy-4,4,4-trifluorobutyl]phenyl 4'-alkyl($C_{3-20}$)oxycarbonyl-4-biphenylcarboxylate, 4-[4-alkyl($C_{1-20}$)carbonyloxy-5,5,5-trifluoropentyl]phenyl 4'-alkyl($C_{3-20}$)oxycarbonyl-4-biphenylcarboxylate, 4-[5-alkyl($C_{1-20}$)carbonyloxy-6,6,6-trifluorohexyl]phenyl 4'-alkyl($C_{3-20}$)oxycarbonyl-4-biphenylcarboxylate, 4-[6-alkyl($C_{1-20}$)carbonyloxy-7,7,7-trifluoroheptyl]phenyl 4'-alkyl($C_{3-20}$)oxycarbonyl-4-biphenylcarboxylate, 4-[1-alkyl($C_{1-20}$)carbonyloxy-2,2,2-trifluoroethyl]phenyl 4'-alkyl($C_{3-20}$)carbonyloxy-4-biphenylcarboxylate, 4-[2-alkyl($C_{1-20}$)carbonyloxy-3,3,3-trifluoropropyl]phenyl 4'-alkyl($C_{3-20}$)carbonyloxy-4-biphenylcarboxylate, 4-[3-alkyl($C_{1-20}$)carbonyloxy-4,4,4-trifluorobutyl]phenyl 4'-alkyl($C_{3-20}$)carbonyloxy-4-biphenylcarboxylate, 4-[4-alkyl($C_{1-20}$)carbonyloxy-5,5,5-trifluoropentyl]phenyl 4'-alkyl($C_{3-20}$)carbonyloxy-4-biphenylcarboxylate, 4-[5-alkyl($C_{1-20}$)carbonyloxy-6,6,6-trifluorohexyl]phenyl 4'-alkyl($C_{3-20}$)carbonyloxy-4-biphenylcarboxylate, 4-[6-alkyl($C_{1-20}$)carbonyloxy-7,7,7-trifluoroheptyl]phenyl 4'-alkyl($C_{3-20}$)carbonyloxy-4-biphenylcarboxylate, 2-[4-[4-[1-alkyl($C_{1-20}$)carbonyloxy-2,2,2-trifluoroethyl]-phenoxycarbonyl]phenyl]-5-alkyl($C_{3-20}$)oxypyrimidine, 2-[4-[2-alkyl($C_{1-20}$)carbonyloxy-3,3,3-trifluoropropyl]phenoxycarbonyl]phenyl]-5-alkyl($C_{3-20}$)oxypyrimidine, 2-[4-[3-alkyl($C_{1-20}$)carbonyloxy-4,4,4-trifluorobutyl]phenoxycarbonyl]phenyl]-5-alkyl($C_{3-20}$)oxypyrimidine, 2-[4-[4-alkyl($C_{1-20}$)carbonyloxy-5,5,5-trifluoropentyl]phenoxycarbonyl]phenyl]-5-alkyl($C_{3-20}$)oxypyrimidine, 2-[4-[5-alkyl($C_{1-20}$)carbonyloxy-6,6,6-trifluorohexyl]phenoxycarbonyl]phenyl]-5-alkyl($C_{3-20}$)oxypyrimidine, 2-[4-[6-alkyl($C_{1-20}$)carbonyloxy-7,7,7-trifluoroheptyl]phenoxycarbonyl]phenyl]-5-alkyl($C_{3-20}$)oxypyrimidine, 2-[4-[1-alkyl($C_{1-20}$)carbonyloxy-2,2,2-trifluoroethyl]phenoxycarbonyl]phenyl]-5-alkyl($C_{3-20}$)pyrimidine, 2-[4-[2-alkyl($C_{1-20}$)carbonyloxy-3,3,3-trifluoropropyl]phenoxycarbonyl]phenyl]-5-alkyl($C_{3-20}$)pyrimidine, 2-[4-[3-alkyl($C_{1-20}$)carbonyloxy-4,4,4-trifluorobutyl]phenoxycarbonyl]phenyl]-5-alkyl($C_{3-20}$)pyrimidine, 2-[4-[4-alkyl($C_{1-20}$)carbonyloxy-5,5,5-trifluoropentyl]phenoxycarbonyl]phenyl]-5-alkyl($C_{3-20}$)pyrimidine, 2-[4-[5-alkyl($C_{1-20}$)carbonyloxy-6,6,6-trifluorohexyl]phenoxycarbonyl]phenyl]-5-alkyl($C_{3-20}$)pyrimidine, 2-[4-[6-alkyl($C_{1-20}$)carbonyloxy-7,7,7-trifluoroheptyl]phenoxycarbonyl]phenyl]-5-alkyl($C_{3-20}$)pyrimidine, 2-[4-[1-alkyl($C_{1-20}$)carbonyloxy-2,2,2-trifluoroethyl]phenoxycarbonyl]phenyl]-5-alkyl($C_{3-20}$)oxycarbonylpyrimidine, 2-[4-[2-alkyl($C_{1-20}$)carbonyloxy-3,3,3-trifluoropropyl]phenoxycarbonyl]phenyl]-5-alkyl($C_{3-20}$)oxycarbonylpyrimidine, 2-[4-[3-alkyl($C_{1-20}$)carbonyloxy-4,4,4-trifluorobutyl]phenoxycarbonyl]phenyl]-5-alkyl($C_{3-20}$)oxycarbonylpyrimidine, 2-[4-[4-alkyl($C_{1-20}$)carbonyloxy-5,5,5-trifluoropentyl]phenoxycarbonyl]phenyl]-5-alkyl($C_{3-20}$)oxycarbonylpyrimidine, 2-[4-[5-alkyl($C_{1-20}$)carbonyloxy-6,6,6-trifluorohexyl]phenoxycarbonyl]phenyl]-5-alkyl($C_{3-20}$)oxycarbonylpyrimidine, 2-[4-[6-alkyl($C_{1-20}$)carbonyloxy-7,7,7-trifluoroheptyl]phenoxycarbonyl]phenyl]-5-alkyl($C_{3-20}$)oxycarbonylpyrimidine, 2-[4-[1-alkyl($C_{1-20}$)carbonyloxy-2,2,2-trifluoroethyl]phenoxycarbonyl]phenyl]-5-alkyl($C_{3-20}$)carbonyloxypyrimidine, 2-[4-[2-alkyl($C_{1-20}$)carbonyloxy-3,3,3-trifluoropropyl]phenoxycarbonyl]phenyl]-5-alkyl($C_{3-20}$)carbonyloxypyrimidine, 2-[4-[3-alkyl($C_{1-20}$)carbonyloxy-4,4,4-trifluorobutyl]phenoxycarbonyl]phenyl]-5-alkyl($C_{3-20}$)carbonyloxypyrimidine, 2-[4-[4-alkyl($C_{1-20}$)carbonyloxy-5,5,5-trifluoropentyl]phenoxycarbonyl]phenyl]-5-alkyl($C_{3-20}$)carbonyloxypyrimidine, 2-[4-[5-alkyl($C_{1-20}$)carbonyloxy-6,6,6-trifluorohexyl]phenoxycarbonyl]phenyl]-5-alkyl($C_{3-20}$)carbonyloxypyrimidine, 2-[4-[6-alkyl($C_{1-20}$)carbonyloxy-7,7,7-trifluoroheptyl]phenoxycarbonyl]phenyl]-5-alkyl($C_{3-20}$)carbonyloxypyrimidine, 4-[1-alkoxyalkyl($C_{2-20}$)carbonyloxy-2,2,2-trifluoroethyl]phenyl 4-alkyl($C_{3-20}$)oxybenzoate, 4-[2-alkoxyalkyl($C_{2-20}$)carbonyloxy-3,3,3-trifluoropropyl]phenyl 4-alkyl($C_{3-20}$)oxybenzoate, 4-[3-alkoxyalkyl($C_{2-20}$)carbonyloxy-4,4,4-trifluorobutyl]phenyl 4-alkyl($C_{3-20}$)oxybenzoate, 4-[4-alkoxyalkyl($C_{2-20}$)carbonyloxy-5,5,5-trifluoropentyl]phenyl 4-alkyl($C_{3-20}$)oxybenzoate, 4-[5-alkoxyalkyl($C_{2-20}$)carbonyloxy-6,6,6-trifluorohexyl]phenyl 4-alkyl($C_{3-20}$)oxybenzoate, 4-[6-alkoxyalkyl($C_{2-20}$)carbonyloxy-7,7,7-trifluoroheptyl]phenyl 4-alkyl($C_{3-20}$)oxybenzoate, 4-[1-alkoxyalkyl($C_{2-20}$)carbonyloxy-2,2,2-trifluoroethyl]phenyl 4-alkyl($C_{3-20}$)benzoate, 4-[2-alkoxyalkyl($C_{2-20}$)carbonyloxy-3,3,3-trifluoropropyl]phenyl 4-alkyl($C_{3-20}$)benzoate, 4-[3-alkoxyalkyl($C_{2-20}$)carbonyloxy-4,4,4-trifluorobutyl]phenyl 4-alkyl($C_{3-20}$)benzoate, 4-[4-alkoxyalkyl($C_{2-20}$)carbonyloxy-5,5,5-trifluoropentyl]phenyl 4-alkyl($C_{3-20}$)benzoate, 4-[5-alkoxyalkyl($C_{2-20}$)carbonyloxy-6,6,6-trifluorohexyl]phenyl 4-alkyl($C_{3-20}$)benzoate, 4-[6-alkoxyalkyl($C_{2-20}$)carbonyloxy-7,7,7-trifluoroheptyl]phenyl 4-alkyl($C_{3-20}$)benzoate, 4-[1-alkoxyalkyl($C_{2-20}$)carbonyloxy-2,2,2-trifluoroethyl]phenyl 4-alkyl($C_{3-20}$)oxycarbonylbenzoate, 4-[2-alkoxyalkyl($C_{2-20}$)carbonyloxy-3,3,3-trifluoropropyl]phenyl 4-alkyl($C_{3-20}$)oxycarbonylbenzoate, 4-[3-alkoxyalkyl($C_{2-20}$)carbonyloxy-4,4,4-trifluorobutyl]phenyl 4-alkyl($C_{3-20}$)oxycarbonylbenzoate, 4-[4-alkoxyalkyl($C_{2-20}$)carbonyloxy-5,5,5-trifluoropentyl]phenyl 4-alkyl($C_{3-20}$)oxycarbonylbenzoate, 4-[5-alkoxyalkyl($C_{2-20}$)carbonyloxy-6,6,6-trifluorohexyl]phenyl 4-alkyl($C_{3-20}$)oxycarbonylbenzoate, 4-[6-alkoxyalkyl($C_{2-20}$)carbonyloxy-7,7,7-trifluoroheptyl]phenyl 4-alkyl($C_{3-20}$)oxycarbonylbenzoate, 4-[1-alkoxyalkyl($C_{2-20}$)carbonyloxy-2,2,2-trifluoroethyl]phenyl 4-alkyl($C_{3-20}$)carbonyloxybenzoate, 4-[2-alkoxyalkyl($C_{2-20}$)carbonyloxy-3,3,3-trifluoropropyl]phenyl 4-alkyl($C_{3-20}$)carbonyloxybenzoate, 4-[3-alkoxyalkyl($C_{2-20}$)carbonyloxy-4,4,4-trifluorobutyl]phenyl 4-alkyl($C_{3-20}$)carbonyloxybenzoate, 4-[4-alkoxyalkyl($C_{2-20}$)carbonyloxy-5,5,5-trifluoropentyl]phenyl 4-alkyl($C_{3-20}$)carbonyloxybenzoate, 4-[5-alkoxyalkyl($C_{2-20}$)carbonyloxy-6,6,6-trifluorohexyl]phenyl 4-alkyl($C_{3-20}$)carbonyloxybenzoate, 4-[6-alkoxyalkyl($C_{2-20}$)carbonyloxy-7,7,7-trifluoroheptyl]phenyl 4-alkyl($C_{3-20}$)carbonyloxybenzoate, 4-[1-alkoxyalkyl($C_{2-20}$)carbonyloxy-2,2,2-trifluoroethyl]phenyl 4'-alkyl($C_{3-20}$)oxy-4-biphenylcarboxylate, 4-[2-alkoxyalkyl($C_{2-20}$)carbonyloxy-3,3,3-trifluoropropyl]phenyl 4'-alkyl($C_{3-20}$)oxy-4-biphenylcarboxylate, 4-[3-alkoxyalkyl($C_{2-20}$)carbonyloxy-4,4,4-trifluorobutyl]phenyl 4'-alkyl($C_{3-20}$)oxy-4-biphenylcarboxylate, 4-[4-alkoxyalkyl($C_{2-20}$)carbonyloxy-5,5,5-trifluoropentyl]phenyl 4'-alkyl($C_{3-20}$)oxy-4-biphenylcarboxylate, 4-[5-alkoxyalkyl($C_{2-20}$)carbonyloxy-6,6,6-trifluorohexyl]phenyl 4'-alkyl($C_{3-20}$)oxy-4-biphenylcarboxylate, 4-[6-alkoxyalkyl($C_{2-20}$)carbonyloxy-7,7,7-trifluoroheptyl]phenyl 4'-alkyl($C_{3-20}$)oxy-4-biphenylcarboxylate, 4-[1-alkoxyalkyl($C_{2-20}$)carbonyloxy-2,2,2-trifluoroethyl]phenyl 4'-alkyl($C_{3-20}$)-4-biphenylcarboxylate, 4-[2-alkoxyalkyl($C_{2-20}$)carbonyloxy-3,3,3-trifluoropropyl]phenyl 4'-alkyl($C_{3-20}$)-4-biphenylcarboxylate, 4-[3-alkoxyalkyl($C_{2-20}$)carbonyloxy-4,4,4-trifluorobutyl]phenyl 4'-alkyl($C_{3-20}$)-4-biphenylcarboxylate,
4-[4-alkoxyalkyl($C_{2-20}$)carbonyloxy-5,5,5-trifluoropentyl]phenyl 4'-alkyl($C_{3-20}$)-4-biphenylcarboxylate,
4-[5-alkoxyalkyl($C_{2-20}$)carbonyloxy-6,6,6-trifluorohexyl]phenyl 4'-alkyl($C_{3-20}$)-4-biphenylcarboxylate,
4-[6-alkoxyalkyl($C_{2-20}$)carbonyloxy-7,7,7-trifluoroheptyl]phenyl 4'-alkyl($C_{3-20}$)-4-biphenylcarboxylate,
4-[1-alkoxyalkyl($C_{2-20}$)carbonyloxy-2,2,2-trifluoroethyl]phenyl 4'-alkyl($C_{3-20}$)oxycarbonyl-4-biphenylcarboxylate,
4-[2-alkoxyalkyl($C_{2-20}$)carbonyloxy-3,3,3-trifluoropropyl]phenyl 4'-alkyl($C_{3-20}$)oxycarbonyl-4-biphenylcarboxylate,
4-[3-alkoxyalkyl($C_{2-20}$)carbonyloxy-4,4,4-trifluorobutyl]phenyl 4'-alkyl($C_{3-20}$)oxycarbonyl-4-biphenylcarboxylate,
4-[4-alkoxyalkyl($C_{2-20}$)carbonyloxy-5,5,5-trifluoropentyl]phenyl 4'-alkyl($C_{3-20}$)oxycarbonyl-4-biphenylcarboxylate,
4-[5-alkoxyalkyl($C_{2-20}$)carbonyloxy-6,6,6-trifluorohexyl]phenyl 4'-alkyl($C_{3-20}$)oxycarbonyl-4-biphenylcarboxylate,
4-[6-alkoxyalkyl($C_{2-20}$)carbonyloxy-7,7,7-trifluoroheptyl]phenyl 4'-alkyl($C_{3-20}$)oxycarbonyl-4-biphenylcarboxylate,
4-[1-alkoxyalkyl($C_{2-20}$)carbonyloxy-2,2,2-trifluoroethyl]phenyl 4'-alkyl($C_{3-20}$)carbonyloxy-4-biphenylcarboxylate,
4-[2-alkoxyalkyl($C_{2-20}$)carbonyloxy-3,3,3-trifluoropropyl]phenyl 4'-alkyl($C_{3-20}$)carbonyloxy-4-biphenylcarboxylate,
4-[3-alkoxyalkyl($C_{2-20}$)carbonyloxy-4,4,4-trifluorobutyl]phenyl 4'-alkyl($C_{3-20}$)carbonyloxy-4-biphenylcarboxylate,
4-[4-alkoxyalkyl($C_{2-20}$)carbonyloxy-5,5,5-trifluoropentyl]phenyl 4'-alkyl($C_{3-20}$)carbonyloxy-4-biphenylcarboxylate,
4-[5-alkoxyalkyl($C_{2-20}$)carbonyloxy-6,6,6-trifluorohexyl]phenyl 4'-alkyl($C_{3-20}$)carbonyloxy-4-biphenylcarboxylate,
4-[6-alkoxyalkyl($C_{2-20}$)carbonyloxy-7,7,7-trifluoroheptyl]phenyl 4'-alkyl($C_{3-20}$)carbonyloxy-4-biphenylcarboxylate,
2-[4-[4-[1-alkoxyalkyl($C_{2-20}$)carbonyloxy-2,2,2-trifluoroethyl]phenoxycarbonyl]phenyl]-5-alkyl($C_{3-20}$)oxypyrimidine,
2-[4-[4-[2-alkoxyalkyl($C_{2-20}$)carbonyloxy-3,3,3-trifluoroethyl]phenoxycarbonyl]phenyl]-5-alkyl($C_{3-20}$)oxypyrimidine,
2-[4-[4-[3-alkoxyalkyl($C_{2-20}$)carbonyloxy-4,4,4-trifluorobutyl]phenoxycarbonyl]phenyl]-5-alkyl($C_{3-20}$)oxypyrimidine,
2-[4-[4-[4-alkoxyalkyl($C_{2-20}$)carbonyloxy-5,5,5-trifluoropentyl]phenoxycarbonyl]phenyl]-5-alkyl($C_{3-20}$)oxypyrimidine,
2-[4-[4-[5-alkoxyalkyl($C_{2-20}$)carbonyloxy-6,6,6-trifluorohexyl]phenoxycarbonyl]phenyl]-5-alkyl($C_{3-20}$)oxypyrimidine,
2-[4-[4-[6-alkoxyalkyl($C_{2-20}$)carbonyloxy-7,7,7-trifluoroheptyl]phenoxycarbonyl]phenyl]-5-alkyl($C_{3-20}$)oxypyrimidine,
2-[4-[4-[1-alkoxyalkyl($C_{2-20}$)carbonyloxy-2,2,2-trifluoroethyl]phenoxycarbonyl]phenyl]-5-alkyl($C_{3-20}$)pyrimidine,
2-[4-[4-[2-alkoxyalkyl($C_{2-20}$)carbonyloxy-3,3,3-trifluoropropyl]phenoxycarbonyl]phenyl]-5-alkyl($C_{3-20}$)pyrimidine,
2-[4-[4-[3-alkoxyalkyl($C_{2-20}$)carbonyloxy-4,4,4-trifluorobutyl]phenoxycarbonyl]phenyl]-5-alkyl($C_{3-20}$)pyrimidine,
2-[4-[4-[4-alkoxyalkyl($C_{2-20}$)carbonyloxy-5,5,5-trifluoropentyl]phenoxycarbonyl]phenyl]-5-alkyl($C_{3-20}$)pyrimidine,
2-[4-[4-[5-alkoxyalkyl($C_{2-20}$)carbonyloxy-6,6,6-trifluorohexyl]phenoxycarbonyl]phenyl]-5-alkyl($C_{3-20}$)pyrimidine,
2-[4-[4-[6-alkoxyalkyl($C_{2-20}$)carbonyloxy-7,7,7-trifluoroheptyl]phenoxycarbonyl]phenyl]-5-alkyl($C_{3-20}$)pyrimidine,
2-[4-[4-[1-alkoxyalkyl($C_{2-20}$)carbonyloxy-2,2,2-trifluoroethyl]phenoxycarbonyl]phenyl]-5-alkyl($C_{3-20}$)oxycarbonylpyrimidine,
2-[4-[4-[2-alkoxyalkyl($C_{2-20}$)carbonyloxy-3,3,3-trifluoropropyl]phenoxycarbonyl]phenyl]-5-alkyl($C_{3-20}$)oxycarbonylpyrimidine,
2-[4-[4-[3-alkoxyalkyl($C_{2-20}$)carbonyloxy-4,4,4-trifluorobutyl]phenoxycarbonyl]phenyl]-5-alkyl($C_{3-20}$)oxycarbonylpyrimidine,
2-[4-[4-[4-alkoxyalkyl($C_{2-20}$)carbonyloxy-5,5,5-trifluoropentyl]phenoxycarbonyl]phenyl]-5-alkyl($C_{3-20}$)oxycarbonylpyrimidine,
2-[4-[4-[5-alkoxyalkyl($C_{2-20}$)carbonyloxy-6,6,6-trifluorohexyl]phenoxycarbonyl]phenyl]-5-alkyl($C_{3-20}$)oxycarbonylpyrimidine,
2-[4-[4-[6-alkoxyalkyl($C_{2-20}$)carbonyloxy-7,7,7-trifluoroheptyl]phenoxycarbonyl]phenyl]-5-alkyl($C_{3-20}$)oxycarbonylpyrimidine,
2-[4-[4-[1-alkoxyalkyl($C_{2-20}$)carbonyloxy-2,2,2-trifluoroethyl]phenoxycarbonyl]phenyl]-5-alkyl($C_{3-20}$)carbonyloxypyrimidine,
2-[4-[4-[2-alkoxyalkyl($C_{2-20}$)carbonyloxy-3,3,3-trifluoropropyl]phenoxycarbonyl]phenyl]-5-alkyl($C_{3-20}$)carbonyloxypyrimidine,
2-[4-[4-[3-alkoxyalkyl($C_{2-20}$)carbonyloxy-4,4,4-trifluorobutyl]phenoxycarbonyl]phenyl]-5-alkyl($C_{3-20}$)carbonyloxypyrimidine,
2-[4-[4-[4-alkoxyalkyl($C_{2-20}$)carbonyloxy-5,5,5-trifluoropentyl]phenoxycarbonyl]phenyl]-5-alkyl($C_{3-20}$)oxypyrimidine,
2-[4-[4-[5-alkoxyalkyl($C_{2-20}$)carbonyloxy-6,6,6-trifluorohexyl]phenoxycarbonyl]phenyl]-5-alkyl($C_{3-20}$)carbonyloxypyrimidine,
2-[4-[4-[6-alkoxyalkyl($C_{2-20}$)carbonyloxy-7,7,7-trifluoroheptyl]phenoxycarbonyl]phenyl]-5-alkyl($C_{3-20}$)carbonyloxypyrimidine, etc.

(b) Compounds wherein X is —OCO—.
4-alkyl($C_{3-20}$)oxyphenyl 4-[2-alkyl($C_{1-20}$)oxy-3,3,3-trifluoropropyl]benzoate,
4-alkyl($C_{3-20}$)oxyphenyl 4-[3-alkyl($C_{1-20}$)oxy-4,4,4-trifluorobutyl]benzoate,
4-alkyl($C_{3-20}$)oxyphenyl 4-[4-alkyl($C_{1-20}$)oxy-5,5,5-trifluoropentyl]benzoate,
4-alkyl($C_{3-20}$)oxyphenyl 4-[5-alkyl($C_{1-20}$)oxy-6,6,6-trifluoropentyl]benzoate,
4-alkyl($C_{3-20}$)oxyphenyl 4-[6-alkyl($C_{1-20}$)oxy-7,7,7-trifluoroheptyl]benzoate,
4-alkyl($C_{3-20}$)phenyl 4-[2-alkyl($C_{1-20}$)oxy-3,3,3-trifluoropropyl]benzoate,
4-alkyl($C_{3-20}$)phenyl 4-[3-alkyl($C_{1-20}$)oxy-4,4,4-trifluorobutyl]benzoate, 4-alkyl($C_{3-20}$)phenyl 4-[4-alkyl($C_{1-20}$)oxy-5,5,5-trifluoropentyl]benzoate,
4-alkyl($C_{3-20}$)phenyl 4-[5-alkyl($C_{1-20}$)oxy-6,6,6-trifluorohexyl]benzoate,
4-alkyl($C_{3-20}$)phenyl 4-[6-alkyl($C_{1-20}$)oxy-7,7,7-trifluoroheptyl]benzoate,
4-alkyl($C_{3-20}$)oxycarbonylphenyl 4-[2-alkyl($C_{1-20}$)oxy-3,3,3-trifluoropropyl]benzoate,
4-alkyl($C_{3-20}$)oxycarbonylphenyl 4-[3-alkyl($C_{1-20}$)oxy-4,4,4-trifluorobutyl]benzoate,
4-alkyl($C_{3-20}$)oxycarbonylphenyl 4-[5-alkyl($C_{1-20}$)oxy-5,5,5-trifluoropentyl]benzoate,
4-alkyl($C_{3-20}$)oxycarbonylphenyl 4-[6-alkyl($C_{1-20}$)oxy-6,6,6-trifluorohexyl]benzoate,
4-alkyl($C_{3-20}$)oxycarbonylphenyl 4-[7-alkyl($C_{1-20}$)oxy-7,7,7-trifluoroheptyl]benzoate,
4-alkyl($C_{3-20}$)carbonyloxyphenyl 4-[2-alkyl($C_{1-20}$)oxy-3,3,3-trifluoropropyl]benzoate,
4-alkyl($C_{3-20}$)carbonyloxyphenyl 4-[3-alkyl($C_{1-20}$)oxy-4,4,4-trifluorobutyl]benzoate,
4-alkyl($C_{3-20}$)carbonyloxyphenyl 4-[4-alkyl($C_{1-20}$)oxy-5,5,5-trifluoropentyl]benzoate,
4-alkyl($C_{3-20}$)carbonyloxyphenyl 4-[5-alkyl($C_{1-20}$)oxy-6,6,6-trifluorohexyl]benzoate,
4-alkyl($C_{3-20}$)carbonyloxyphenyl 4-[6-alkyl($C_{1-20}$)oxy-7,7,7-trifluoroheptyl]benzoate,
4'-alkyl($C_{3-20}$)oxy-4-biphenylyl 4-[2-alkyl($C_{1-20}$)oxy-3,3,3-trifluoropropyl]benzoate,
4'-alkyl($C_{3-20}$)oxy-4-biphenylyl 4-[3-alkyl($C_{1-20}$)oxy-4,4,4-trifluorobutyl]benzoate,
4'-alkyl($C_{3-20}$))oxy-4-biphenylyl 4-[4-alkyl($C_{1-20}$)oxy-5,5,5-trifluoropentyl]benzoate,
4'-alkyl($C_{3-20}$)oxy-4-biphenylyl 4-[5-alkyl($C_{1-20}$)oxy-6,6,6-trifluorohexyl]benzoate,
4'-alkyl($C_{3-20}$)oxy-4-biphenylyl 4-[6-alkyl($C_{1-20}$)oxy-7,7,7-trifluoroheptyl]benzoate,
4'-alkyl($C_{3-20}$)-4-biphenylyl 4-[2-alkyl($C_{1-20}$)oxy-3,3,3-trifluoropropyl]benzoate,
4'-alkyl($C_{3-20}$)-4-biphenylyl 4-[3-alkyl($C_{1-20}$)oxy-4,4,4-trifluorobutyl]benzoate,
4'-alkyl($C_{3-20}$)-4-biphenylyl 4-[4-alkyl($C_{1-20}$)oxy-5,5,5-trifluoropentyl]benzoate,
4'-alkyl($C_{3-20}$)-4-biphenylyl 4-[5-alkyl($C_{1-20}$)oxy-6,6,6-trifluorohexyl]benzoate,
4'-alkyl($C_{3-20}$)-4-biphenylyl 4-[6-alkyl($C_{1-20}$)oxy-7,7,7-trifluoroheptyl]benzoate,
4'-alkyl($C_{3-20}$)oxycarbonyl-4-biphenylyl 4-[2-alkyl($C_{1-20}$)oxy-3,3,3-trifluoropropyl]benzoate,
4'-alkyl($C_{3-20}$)oxycarbonyl-4-biphenylyl 4-[3-alkyl($C_{1-20}$)oxy-4,4,4-trifluorobutyl]benzoate,
4'-alkyl($C_{3-20}$)oxycarbonyl-4-biphenylyl 4-[4-alkyl($C_{1-20}$)oxy-5,5,5-trifluoropentyl]benzoate,
4'-alkyl($C_{3-20}$)oxycarbonyl-4-biphenylyl 4-[5-alkyl($C_{1-20}$)oxy-6,6,6-trifluorohexyl]benzoate,
4'-alkyl($C_{3-20}$)oxycarbonyl-4-biphenylyl 4-[6-alkyl($C_{1-20}$)oxy-7,7,7-trifluoroheptyl]benzoate,
4'-alkyl($C_{3-20}$))carbonyloxy-4-biphenylyl 4-[2-alkyl($C_{1-20}$)oxy-3,3,3-trifluoropropyl]benzoate,
4'-alkyl($C_{3-20}$)carbonyloxy-4-biphenylyl 4-[3-alkyl($C_{1-20}$)oxy-4,4,4-trifluorobutyl]benzoate,
4'-alkyl($C_{3-20}$)carbonyloxy-4-biphenylyl 4-[4-alkyl($C_{1-20}$)oxy-5,5,5-trifluoropentyl]benzoate,
4'-alkyl($C_{3-20}$)carbonyloxy-4-biphenylyl 4-[5-alkyl($C_{1-20}$)oxy-6,6,6-trifluorohexyl]benzoate,
4'-alkyl($C_{3-20}$)carbonyloxy-4-biphenylyl 4-[6-alkyl($C_{1-20}$)oxy-7,7,7-trifluoroheptyl benzoate,
2-[4-[4-[2-alkyl($C_{1-20}$)oxy-3,3,3-trifluoropropyl]phenylcarbonyloxy]phenyl]-5-alkyl($C_{3-20}$)oxypyrimidine,
2-[4-[4-[3-alkyl($C_{1-20}$)oxy-4,4,4-trifluorobutyl]phenylcarbonyloxy]phenyl]-5-alkyl($C_{3-20}$)oxypyrimidine,
2-[4-[4-[4-alkyl($C_{1-20}$)oxy-5,5,5-trifluoropentyl]phenylcarbonyloxy]phenyl]-5-alkyl($C_{3-20}$)oxypyrimidine,
2-[4-[4-[5-alkyl($C_{1-20}$)oxy-6,6,6-trifluorohexyl]phenylcarbonyloxy]phenyl]-5-alkyl($C_{3-20}$)oxypyrimidine,
2-[4-[4-[6-alkyl($C_{1-20}$)oxy-7,7,7-trifluoroheptyl]phenylcarbonyloxy]phenyl]-5-alkyl($C_{3-20}$)oxypyrimidine,
2-[4-[4-[2-alkyl($C_{1-20}$)oxy-3,3,3-trifluoropropyl]phenylcarbonyloxy]phenyl]-5-alkyl($C_{3-20}$)pyrimidine,
2-[4-[4-[3-alkyl($C_{1-20}$)oxy-4,4,4-trifluorobutyl]phenylcarbonyloxy]phenyl]-5-alkyl($C_{3-20}$)pyrimidine,
2-[4-[4-[4-alkyl($C_{1-20}$)oxy-5,5,5-trifluoropentyl]phenylcarbonyloxy]phenyl]-5-alkyl($C_{3-20}$)pyrimidine,
2-[4-[4-[5-alkyl($C_{1-20}$)oxy-6,6,6-trifluorohexyl]phenylcarbonyloxy]phenyl]-5-alkyl($C_{3-20}$)pyrimidine,
2-[4-[4-[6-alkyl($C_{1-20}$)oxy-7,7,7-trifluoroheptyl]phenylcarbonyloxy]phenyl]-5-alkyl($C_{3-20}$)pyrimidine,
2-[4-[4-[2-alkyl($C_{1-20}$)oxy-3,3,3-trifluoropropyl]phenylcarbonyloxy]phenyl]-5-alkyl($C_{3-20}$)oxycarbonylpyrimidine,
2-[4-[4-[3-alkyl($C_{1-20}$)oxy-4,4,4-trifluorobutyl]phenylcarbonyloxy]phenyl]-5-alkyl($C_{3-20}$)oxycarbonylpyrimidine,
2-[4-[4-[4-alkyl($C_{1-20}$)oxy-5,5,5-trifluoropentyl]phenylcarbonyloxy]phenyl]-5-alkyl($C_{3-20}$)oxycarbonylpyrimidine,
2-[4-[4-[5-alkyl($C_{1-20}$)oxy-6,6,6-trifluorohexyl]phenylcarbonyloxy]phenyl]-5-alkyl($C_{3-20}$)oxycarbonylpyrimidine,
2-[4-[4-[6-alkyl($C_{1-20}$)oxy-7,7,7-trifluoroheptyl]phenylcarbonyloxy]phenyl]-5-alkyl($C_{3-20}$)oxycarbonylpyrimidine,
2-[4-[4-[2-alkyl($C_{1-20}$)oxy-3,3,3-trifluoropropyl]phenylcarbonyloxy]phenyl-5-alkyl($C_{3-20}$)carbonyloxypyrimidine,
2-[4-[4-[3-alkyl($C_{1-20}$)oxy-4,4,4-trifluorobutyl]phenylcarbonyloxy]phenyl-5-alkyl($C_{3-20}$)carbonyloxypyrimidine,
2-[4-[4-[4-alkyl($C_{1-20}$)oxy-5,5,5-trifluoropentyl]phenylcarbonyloxy]phenyl-5-alkyl($C_{3-20}$)carbonyloxypyrimidine,
2-[4-[4-[5-alkyl($C_{1-20}$)oxy-6,6,6-trifluorohexyl]phenylcarbonyloxy]phenyl-5-alkyl($C_{3-20}$)carbonyloxypyrimidine,
2-[4-[4-[6-alkyl($C_{1-20}$)oxy-7,7,7-trifluoroheptyl]phenylcarbonyloxy]phenyl-5-alkyl($C_{3-20}$)carbonyloxypyrimidine,
4-alkyl($C_{3-20}$)oxyphenyl 4-[2-alkoxyalkyl($C_{2-20}$)oxy-3,3,3-trifluoropropyl]benzoate,
4-alkyl($C_{3-20}$)oxyphenyl 4-[3-alkoxyalkyl($C_{2-20}$)oxy-4,4,4-trifluorobutyl]benzoate,
4-alkyl($C_{3-20}$)oxyphenyl 4-[4-alkoxyalkyl($C_{2-20}$)oxy-5,5,5-trifluoropentyl]benzoate,
4-alkyl($C_{3-20}$)oxyphenyl 4-[5-alkoxyalkyl($C_{2-20}$)oxy-6,6,6-trifluorohexyl]benzoate,
4-alkyl($C_{3-20}$)oxyphenyl 4-[6-alkoxyalkyl($C_{2-20}$)oxy-7,7,7-trifluoroheptyl]benzoate,
4-alkyl($C_{3-20}$)phenyl 4-[2-alkoxyalkyl($C_{2-20}$)oxy-3,3,3-trifluoropropyl]benzoate,
4-alkyl($C_{3-20}$))phenyl 4-[3-alkoxyalkyl($C_{2-20}$)oxy-4,4,4-trifluorobutyl]benzoate,
4-alkyl($C_{3-20}$)phenyl 4-[4-alkoxyalkyl($C_{2-20}$)oxy-5,5,5-trifluoropentyl]benzoate,
4-alkyl($C_{3-20}$)phenyl 4-[5-alkoxyalkyl($C_{2-20}$)oxy-6,6,6-trifluorohexyl]benzoate,
4-alkyl($C_{3-20}$)phenyl 4-[6-alkoxyalkyl($C_{2-20}$)oxy-7,7,7-trifluoroheptyl]benzoate, 4-alkyl($C_{3-20}$)oxycarbonylphenyl 4-[2-alkoxyalkyl($C_{2-20}$)oxy-3,3,3-trifluoropropyl]benzoate,
4-alkyl($C_{3-20}$)oxycarbonylphenyl 4-[3-alkoxyalkyl($C_{2-20}$)oxy-4,4,4-trifluorobutyl]benzoate,
4-alkyl($C_{3-20}$)oxycarbonylphenyl 4-[4-alkoxyalkyl($C_{2-20}$)oxy-5,5,5-trifluoropentyl]benzoate,
4-alkyl($C_{3-20}$)oxycarbonylphenyl 4-[5-alkoxyalkyl($C_{2-20}$)oxy-6,6,6-trifluorohexyl]benzoate,
4-alkyl($C_{3-20}$)oxycarbonylphenyl 4-[6-alkoxyalkyl($C_{2-20}$)oxy-7,7,7-trifluoroheptyl]benzoate,
4-alkyl($C_{3-20}$)carbonyloxyphenyl 4-[2-alkoxyalkyl($C_{2-20}$)oxy-3,3,3-trifluoropropyl]benzoate,
4-alkyl($C_{3-20}$)carbonyloxyphenyl 4-[3-alkoxyalkyl($C_{2-20}$)oxy-4,4,4-trifluorobutyl]benzoate,
4-alkyl($C_{3-20}$)carbonyloxyphenyl 4-[4-alkoxyalkyl($C_{2-20}$)oxy-5,5,5-trifluoropentyl]benzoate,
4-alkyl($C_{3-20}$)carbonyloxyphenyl 4-[5-alkoxyalkyl($C_{2-20}$)oxy-6,6,6-trifluorohexyl]benzoate,
4-alkyl($C_{3-20}$)carbonyloxyphenyl 4-[6-alkoxyalkyl($C_{2-20}$)oxy-7,7,7-trifluoroheptyl]benzoate,
4'-alkyl($C_{3-20}$)oxy-4-biphenylyl 4-[2-alkoxyalkyl($C_{2-20}$)oxy-3,3,3-trifluoropropyl]benzoate,
4'-alkyl($C_{3-20}$)oxy-4-biphenylyl 4-[3-alkoxyalkyl($C_{2-20}$)oxy-4,4,4-trifluorobutyl]benzoate,
4'-alkyl($C_{3-20}$)oxy-4-biphenylyl 4-[4-alkoxyalkyl($C_{2-20}$)oxy-5,5,5-trifluoropentyl]benzoate,
4'-alkyl($C_{3-20}$)oxy-4-biphenylyl 4-[5-alkoxyalkyl($C_{2-20}$)oxy-6,6,6-trifluorohexyl]benzoate,
4'-alkyl($C_{3-20}$)oxy-4-biphenylyl 4-[6-alkoxyalkyl($C_{2-20}$)oxy-7,7,7-trifluoroheptyl]benzoate,
4'-alkyl($C_{3-20}$)-4-biphenylyl 4-[2-alkoxyalkyl($C_{2-20}$)oxy-3,3,3-trifluoropropyl]benzoate,
4'-alkyl($C_{3-20}$)-4-biphenylyl 4-[3-alkoxyalkyl($C_{2-20}$)oxy-4,4,4-trifluorobutyl]benzoate,
4'-alkyl($C_{3-20}$)-4-biphenylyl 4-[4-alkoxyalkyl($C_{2-20}$)oxy-5,5,5-trifluoropentyl]benzoate,
4'-alkyl($C_{3-20}$)-4-biphenylyl 4-[5-alkoxyalkyl($C_{2-20}$)oxy-6,6,6-trifluorohexyl]benzoate,
4'-alkyl($C_{3-20}$)-4-biphenylyl 4-[6-alkoxyalkyl($C_{2-20}$)oxy-7,7,7-trifluoroheptyl]benzoate,
4'-alkyl($C_{3-20}$)oxycarbonyl-4-biphenylyl 4-[2-alkoxyalkyl($C_{2-20}$)oxy-3,3,3-trifluoropropyl]benzoate,
4'-alkyl($C_{3-20}$)oxycarbonyl-4-biphenyl 4-[3-alkoxyalkyl($C_{2-20}$)oxy-4,4,4-trifluorobutyl]benzoate,
4'-alkyl($C_{3-20}$)oxycarbonyl-4-biphenylyl 4-[4-alkoxyalkyl($C_{2-20}$)oxy-5,5,5-trifluoropentyl]benzoate,
4'-alkyl($C_{3-20}$)oxycarbonyl-4-biphenylyl 4-[5-alkoxyalkyl($C_{2-20}$)oxy-6,6,6-trifluorohexyl]benzoate,
4'-alkyl($C_{3-20}$)oxycarbonyl-4-biphenylyl 4-[6-alkoxyalkyl($C_{2-20}$)oxy-7,7,7-trifluoroheptyl]benzoate,
4'-alkyl($C_{3-20}$)carbonyloxy-4-biphenylyl 4-[2-alkoxyalkyl($C_{3-20}$)oxy-3,3,3-trifluoropropyl]benzoate,
4'-alkyl($C_{3-20}$)carbonyloxy-4-biphenylyl 4-[3-alkoxyalkyl($C_{3-20}$)oxy-4,4,4-trifluorobutyl]benzoate,
4'-alkyl($C_{3-20}$)carbonyloxy-4-biphenylyl 4-[4-alkoxyalkyl($C_{3-20}$)oxy-5,5,5-trifluoropentyl]benzoate,
4'-alkyl($C_{3-20}$)carbonyloxy-4-biphenylyl 4-[5-alkoxyalkyl($C_{3-20}$)oxy-6,6,6-trifluorohexyl]benzoate,
4'-alkyl($C_{3-20}$)carbonyloxy-4-biphenylyl 4-[6-alkoxyalkyl($C_{3-20}$)oxy-7,7,7-trifluoroheptyl]benzoate,
2-[4-[4-[2-alkoxyalkyl($C_{2-20}$)oxy-3,3,3-trifluoropropyl]phenylcarbonyloxy]phenyl]-5-alkyl($C_{3-20}$)oxypyrimidine,
2-[4-[4-[3-alkoxyalkyl($C_{2-20}$)oxy-4,4,4-trifluorobutyl]phenylcarbonyloxy]phenyl]-5-alkyl($C_{3-20}$)oxypyrimidine,
2-[4-[4-[4-alkoxyalkyl($C_{2-20}$)oxy-5,5,5-trifluoropentyl]phenylcarbonyloxy]phenyl]-5-alkyl($C_{3-20}$)oxypyrimidine,
2-[4-[4-[5-alkoxyalkyl($C_{2-20}$)oxy-6,6,6-trifluorohexyl]phenylcarbonyloxy]phenyl]-5-alkyl($C_{3-20}$)oxypyrimidine,
2-[4-[4-[6-alkoxyalkyl($C_{2-20}$)oxy-7,7,7-trifluoroheptyl]phenylcarbonyloxy]phenyl]-5-alkyl($C_{3-20}$)oxypyrimidine,
2-[4-[4-[2-alkoxyalkyl($C_{2-20}$)oxy-3,3,3-trifluoropropyl]phenyl]carbonyloxy]phenyl]-5-alkyl($C_{3-20}$)pyrimidine,
2-[4-[4-[3-alkoxyalkyl($C_{2-20}$)oxy-4,4,4-trifluorobutyl]phenyl]carbonyloxy]phenyl]-5-alkyl($C_{3-20}$)pyrimidine,
2-[4-[4-[4-alkoxyalkyl($C_{2-20}$)oxy-5,5,5-trifluoropentyl]phenyl]carbonyloxy]phenyl]-5-alkyl($C_{3-20}$)pyrimidine,
2-[4-[4-[5-alkoxyalkyl($C_{2-20}$)oxy-6,6,6-trifluorohexyl]phenyl]carbonyloxy]phenyl]-5-alkyl($C_{3-20}$)pyrimidine,
2-[4-[4-[6-alkoxyalkyl($C_{2-20}$)oxy-7,7,7-trifluoroheptyl]phenyl]carbonyloxy]phenyl]-5-alkyl($C_{3-20}$)pyrimidine,
2-[4-[4-[2-alkoxyalkyl($C_{2-20}$)oxy-3,3,3-trifluoropropyl]phenyl]carbonyloxy]phenyl]-5-alkyl($C_{3-20}$)oxycarbonylpyrimidine,
2-[4-[4-[3-alkoxyalkyl($C_{2-20}$)oxy-4,4,4-trifluoropropyl]phenyl]carbonyloxy]phenyl]-5-alkyl($C_{3-20}$)oxycarbonylpyrimidine,
2-[4-[4-[4-alkoxyalkyl($C_{2-20}$)oxy-5,5,5-trifluorobutyl]phenyl]carbonyloxy]phenyl]-5-alkyl($C_{3-20}$)oxycarbonylpyrimidine,
2-[4-[4-[5-alkoxyalkyl($C_{2-20}$)oxy-6,6,6-trifluorohexyl]phenyl]carbonyloxy]phenyl]-5-alkyl($C_{3-20}$)oxycarbonylpyrimidine,
2-[4-[4-[6-alkoxyalkyl($C_{2-20}$)oxy-7,7,7-trifluoroheptyl]phenyl]carbonyloxy]phenyl]-5-alkyl($C_{3-20}$)oxycarbonylpyrimidine,
2-[4-[4-[2-alkoxyalkyl($C_{2-20}$)oxy-3,3,3-trifluoropropyl]phenylcarbonyloxy]phenyl]-5-alkyl($C_{3-20}$)oxycarbonyloxypyrimidine,
2-[4-[4-[3-alkoxyalkyl($C_{2-20}$)oxy-4,4,4-trifluorobutyl]phenylcarbonyloxy]phenyl]-5-alkyl($C_{3-20}$)oxycarbonyloxypyrimidine,
2-[4-[4-[4-alkoxyalkyl($C_{2-20}$)oxy-5,5,5-trifluoropentyl]phenylcarbonyloxy]phenyl]-5-alkyl($C_{3-20}$)oxycarbonyloxypyrimidine,
2-[4-[4-[5-alkoxyalkyl($C_{2-20}$)oxy-6,6,6-trifluorohexyl]phenylcarbonyloxy]phenyl]-5-alkyl($C_{3-20}$)oxycarbonyloxypyrimidine,
2-[4-[4-[6-alkoxyalkyl($C_{2-20}$)oxy-7,7,7-trifluoroheptyl]phenylcarbonyloxy]phenyl]-5-alkyl($C_{3-20}$)oxycarbonyloxypyrimidine,
4-alkyl($C_{3-20}$)oxyphenyl 4-[2-alkyl($C_{1-20}$)carbonyloxy-3,3,3-trifluoropropyl]benzoate,
4-alkyl($C_{3-20}$)oxyphenyl 4-[3-alkyl($C_{1-20}$)carbonyloxy-4,4,4-trifluorobutyl]benzoate,
4-alkyl($C_{3-20}$)oxyphenyl 4-[4-alkyl($C_{1-20}$)carbonyloxy-5,5,5-trifluoropentyl]benzoate,
4-alkyl($C_{3-20}$)oxyphenyl 4-[5-alkyl($C_{1-20}$)carbonyloxy-6,6,6-trifluorohexyl]benzoate,
4-alkyl($C_{3-20}$)oxyphenyl 4-[6-alkyl($C_{1-20}$)carbonyloxy-7,7,7-trifluoroheptyl]benzoate,
4-alkyl($C_{3-20}$)phenyl 4-[2-alkyl($C_{1-20}$)carbonyloxy-3,3,3-trifluoropropyl]benzoate,
4-alkyl($C_{3-20}$)phenyl 4-[3-alkyl($C_{1-20}$)carbonyloxy-4,4,4-trifluorobutyl]benzoate, 4-alkyl($C_{3-20}$)phenyl 4-[4-alkyl($C_{1-20}$)carbonyloxy-5,5,5-trifluoropentyl]benzoate,
4-alkyl($C_{3-20}$)phenyl 4-[5-alkyl($C_{1-20}$)carbonyloxy-6,6,6-trifluorohexyl]benzoate,
4-alkyl($C_{3-20}$)phenyl 4-[6-alkyl($C_{1-20}$)carbonyloxy-7,7,7-trifluoroheptyl]benzoate,
4-alkyl($C_{3-20}$)oxycarbonylphenyl 4-[2-alkyl($C_{1-20}$)carbonyloxy-3,3,3-trifluoropropyl]benzoate,
4-alkyl($C_{3-20}$)oxycarbonylphenyl 4-[3-alkyl($C_{1-20}$)carbonyloxy-4,4,4-trifluorobutyl]benzoate,
4-alkyl($C_{3-20}$)oxycarbonylphenyl 4-[4-alkyl($C_{1-20}$)carbonyloxy-5,5,5-trifluoropentyl]benzoate,
4-alkyl($C_{3-20}$)oxycarbonylphenyl 4-[5-alkyl($C_{1-20}$)carbonyloxy-6,6,6-trifluorohexyl]benzoate,
4-alkyl($C_{3-20}$)oxycarbonylphenyl 4-[6-alkyl($C_{1-20}$)carbonyloxy-7,7,7-trifluoroheptyl]benzoate,
4-alkyl($C_{3-20}$)carbonyloxyphenyl 4-[2-alkyl($C_{1-20}$)carbonyloxy-3,3,3-trifluoropropyl]benzoate,
4-alkyl($C_{3-20}$)carbonyloxyphenyl 4-[3-alkyl($C_{1-20}$)carbonyloxy-4,4,4-trifluorobutyl]benzoate,
4-alkyl($C_{3-20}$)carbonyloxyphenyl 4-[4-alkyl($C_{1-20}$)carbonyloxy-5,5,5-trifluoropentyl]benzoate,
4-alkyl($C_{3-20}$)carbonyloxyphenyl 4-[5-alkyl($C_{1-20}$)carbonyloxy-6,6,6-trifluorohexyl]benzoate,
4-alkyl($C_{3-20}$)carbonyloxyphenyl 4-[6-alkyl($C_{1-20}$)carbonyloxy-7,7,7-trifluoroheptyl]benzoate,
4'-alkyl($C_{3-20}$)oxy-4-biphenylyl 4-[2-alkyl($C_{1-20}$)carbonyloxy-3,3,3-trifluoropropyl]benzoate,
4'-alkyl($C_{3-20}$)oxy-4-biphenylyl 4-[3-alkyl($C_{1-20}$)carbonyloxy-4,4,4-trifluorobutyl]benzoate,
4'-alkyl($C_{3-20}$)oxy-4-biphenylyl 4-[4-alkyl($C_{1-20}$)carbonyloxy-5,5,5-trifluoropentyl]benzoate,
4'-alkyl($C_{3-20}$)oxy-4-biphenylyl 4-[5-alkyl($C_{1-20}$)carbonyloxy-6,6,6-trifluorohexyl]benzoate,
4'-alkyl($C_{3-20}$)oxy-4-biphenylyl 4-[6-alkyl($C_{1-20}$)carbonyloxy-7,7,7-trifluoroheptyl]benzoate,
4'-alkyl($C_{3-20}$)-4-biphenylyl 4-[2-alkyl($C_{1-20}$)carbonyloxy-3,3,3-trifluoropropyl]benzoate,
4'-alkyl($C_{3-20}$)-4-biphenylyl 4-[3-alkyl($C_{1-20}$)carbonyloxy-4,4,4-trifluorobutyl]benzoate,
4'-alkyl($C_{3-20}$)-4-biphenylyl 4-[4-alkyl($C_{1-20}$)carbonyloxy-5,5,5-trifluoropentyl]benzoate,
4'-alkyl($C_{3-20}$)-4-biphenylyl 4-[5-alkyl($C_{1-20}$)carbonyloxy-6,6,6-trifluorohexyl]benzoate,
4'-alkyl($C_{3-20}$)-4-biphenylyl 4-[6-alkyl($C_{1-20}$)carbonyloxy-7,7,7-trifluoroheptyl]benzoate,
4'-alkyl($C_{3-20}$)oxycarbonyl-4-biphenylyl 4-[2-alkyl($C_{1-20}$)carbonyloxy-3,3,3-trifluoropropyl]benzoate,
4'-alkyl($C_{3-20}$)oxycarbonyl-4-biphenylyl 4-[3-alkyl($C_{1-20}$)carbonyloxy-4,4,4-trifluorobutyl]benzoate,
4'-alkyl($C_{3-20}$)oxycarbonyl-4-biphenylyl 4-[4-alkyl($C_{1-20}$)carbonyloxy-5,5,5-trifluoropentyl]benzoate,
4'-alkyl($C_{3-20}$)oxycarbonyl-4-biphenylyl 4-[5-alkyl($C_{1-20}$)carbonyloxy-6,6,6-trifluorohexyl]benzoate,
4'-alkyl($C_{3-20}$)oxycarbonyl-4-biphenylyl 4-[6-alkyl($C_{1-20}$)carbonyloxy-7,7,7-trifluoroheptyl]benzoate,
4'-alkyl($C_{3-20}$)carbonyloxy-4-biphenylyl 4-[2-alkyl($C_{1-20}$)carbonyloxy-3,3,3-trifluoropropyl]benzoate,
4'-alkyl($C_{3-20}$)carbonyloxy-4-biphenylyl 4-[3-alkyl($C_{1-20}$)carbonyloxy-4,4,4-trifluorobutyl]benzoate,
4'-alkyl($C_{3-20}$)carbonyloxy-4-biphenylyl 4-[4-alkyl($C_{1-20}$)carbonyloxy-5,5,5-trifluoropentyl]benzoate,
4'-alkyl($C_{3-20}$)carbonyloxy-4-biphenylyl 4-[5-alkyl($C_{1-20}$)carbonyloxy-6,6,6-trifluorohexyl]benzoate,
4'-alkyl($C_{3-20}$)carbonyloxy-4-biphenylyl 4-[6-alkyl($C_{1-20}$)carbonyloxy-7,7,7-trifluoroheptyl]benzoate, 2-[4-[4-[2-alkyl($C_{1-20}$)carbonyloxy-3,3,3-trifluoropropyl]phenylcarbonyloxy]phenyl]-5-alkyl($C_{3-20}$)oxypyrimidine,
2-[4-[4-[3-alkyl($C_{1-20}$))carbonyloxy-4,4,4-trifluorobutyl]phenylcarbonyloxy]phenyl]-5-alkyl($C_{3-20}$)oxypyrimidine,
2-[4-[4-[4-alkyl($C_{1-20}$)carbonyloxy-5,5,5-trifluoropentyl]phenylcarbonyloxy]phenyl]-5-alkyl($C_{3-20}$)oxypyrimidine,
2-[4-[4-[5-alkyl($C_{1-20}$)carbonyloxy-6,6,6-trifluorohexyl]phenylcarbonyloxy]phenyl]-5-alkyl($C_{3-20}$)oxypyrimidine,
2-[4-[4-[6-alkyl($C_{1-20}$)carbonyloxy-7,7,7-trifluoroheptyl]phenylcarbonyloxy]phenyl]-5-alkyl($C_{3-20}$)oxypyrimidine,
2-[4-[4-[2-alkyl($C_{1-20}$)carbonyloxy-3,3,3-trifluoropropyl]phenylcarbonyloxy]phenyl]-5-alkyl($C_{3-20}$)pyrimidine,
2-[4-[4-[3-alkyl($C_{1-20}$)carbonyloxy-4,4,4-trifluorobutyl]phenylcarbonyloxy]phenyl]-5-alkyl($C_{3-20}$)pyrimidine,
2-[4-[4-[4-alkyl($C_{1-20}$)carbonyloxy-5,5,5-trifluoropentyl]phenylcarbonyloxy]phenyl]-5-alkyl($C_{3-20}$)pyrimidine,
2-[4-[4-[5-alkyl($C_{1-20}$)carbonyloxy-6,6,6-trifluorohexyl]phenylcarbonyloxy]phenyl]-5-alkyl($C_{3-20}$)pyrimidine,
2-[4-[4-[6-alkyl($C_{1-20}$)carbonyloxy-7,7,7-trifluoroheptyl]phenylcarbonyloxy]phenyl]-5-alkyl($C_{3-20}$)pyrimidine,
2-[4-[4-[2-alkyl($C_{1-20}$)carbonyloxy-3,3,3-trifluoropropyl]phenylcarbonyloxy]phenyl]-5-alkyl($C_{3-20}$)oxycarbonylpyrimidine,
2-[4-[4-[3-alkyl($C_{1-20}$)carbonyloxy-4,4,4-trifluorobutyl]phenylcarbonyloxy]phenyl]-5-alkyl($C_{3-20}$)oxycarbonylpyrimidine,
2-[4-[4-[4-alkyl($C_{1-20}$)carbonyloxy-5,5,5-trifluoropentyl]phenylcarbonyloxy]phenyl]-5-alkyl($C_{3-20}$)oxycarbonylpyrimidine,
2-[4-[4-[5-alkyl($C_{1-20}$)carbonyloxy-6,6,6-trifluorohexyl]phenylcarbonyloxy]phenyl]-5-alkyl($C_{3-20}$)oxycarbonylpyrimidine,
2-[4-[4-[6-alkyl($C_{1-20}$)carbonyloxy-7,7,7-trifluoroheptyl]phenylcarbonyloxy]phenyl]-5-alkyl($C_{3-20}$)oxycarbonylpyrimidine,
2-[4-[4-[2-alkyl($C_{1-20}$)carbonyloxy-3,3,3-trifluoropropyl]phenylcarbonyloxy]phenyl]-5-alkyl($C_{3-20}$)carbonyloxypyrimidine,
2-[4-[4-[3-alkyl($C_{1-20}$)carbonyloxy-4,4,4-trifluorobutyl]phenylcarbonyloxy]phenyl]-5-alkyl($C_{3-20}$)carbonyloxypyrimidine,
2-[4-[4-[4-alkyl($C_{1-20}$)carbonyloxy-5,5,5-trifluoropentyl]phenyl]-5-alkyl($C_{3-20}$)carbonyloxypyrimidine,
2-[4-[4-[5-alkyl($C_{1-20}$)carbonyloxy-6,6,6-trifluorohexyl]phenylcarbonyloxy]phenyl]-5-alkyl($C_{3-20}$)carbonyloxypyrimidine,
2-[4-[4-[6-alkyl($C_{1-20}$)carbonyloxy-7,7,7-trifluoroheptyl]phenylcarbonyloxy]phenyl]-5-alkyl($C_{3-20}$)carbonyloxypyrimidine,
4-alkyl($C_{3-20}$)oxyphenyl 4-[2-alkoxyalkyl($C_{2-20}$)carbonyloxy-3,3,3-trifluoropropyl]benzoate,
4-alkyl($C_{3-20}$)oxyphenyl 4-[3-alkoxyalkyl($C_{2-20}$)carbonyloxy-4,4,4-trifluorobutyl]benzoate,
4-alkyl($C_{3-20}$)oxyphenyl 4-[4-alkoxyalkyl($C_{2-20}$)carbonyloxy-5,5,5-trifluoropentyl]benzoate,
4-alkyl($C_{3-20}$)oxyphenyl 4-[5-alkoxyalkyl($C_{2-20}$)carbonyloxy-6,6,6-trifluorohexyl]benzoate, 4-alkyl($C_{3-20}$)oxyphenyl 4-[6-alkoxyalkyl($C_{2-20}$)carbonyloxy-7,7,7-trifluoroheptyl]benzoate,
4-alkyl($C_{3-20}$)phenyl 4-[2-alkoxyalkyl($C_{2-20}$)carbonyloxy-3,3,3-trifluoropropyl]benzoate,
4-alkyl($C_{3-20}$)phenyl 4-[3-alkoxyalkyl($C_{2-20}$)carbonyloxy-4,4,4-trifluorobutyl]benzoate,
4-alkyl($C_{3-20}$)phenyl 4-[4-alkoxyalkyl($C_{2-20}$)carbonyloxy-5,5,5-trifluoropentyl]benzoate,
4-alkyl($C_{3-20}$)phenyl 4-[5-alkoxyalkyl($C_{2-20}$)carbonyloxy-6,6,6-trifluorohexyl]benzoate,
4-alkyl($C_{3-20}$)phenyl 4-[6-alkoxyalkyl($C_{2-20}$)carbonyloxy-7,7,7-trifluoroheptyl]benzoate,
4-alkyl($C_{3-20}$)oxycarbonylphenyl 4-[2-alkoxyalkyl($C_{2-20}$)carbonyloxy-3,3,3-trifluoropropyl]benzoate,
4-alkyl($C_{3-20}$)oxycarbonylphenyl 4-[3-alkoxyalkyl($C_{2-20}$)carbonyloxy-4,4,4-trifluorobutyl]benzoate,
4-alkyl($C_{3-20}$)oxycarbonylphenyl 4-[4-alkoxyalkyl($C_{2-20}$)carbonyloxy-5,5,5-trifluoropentyl]benzoate,
4-alkyl($C_{3-20}$)oxycarbonylphenyl 4-[5-alkoxyalkyl($C_{2-20}$)carbonyloxy-6,6,6-trifluorohexyl]benzoate,
4-alkyl($C_{3-20}$)oxycarbonylphenyl 4-[6-alkoxyalkyl($C_{2-20}$)carbonyloxy-7,7,7-trifluoroheptyl]benzoate,
4-alkyl($C_{3-20}$)carbonyloxyphenyl 4-[2-alkoxyalkyl($C_{2-20}$)carbonyloxy-3,3,3-trifluoropropyl]benzoate,
4-alkyl($C_{3-20}$)carbonyloxyphenyl 4-[3-alkoxyalkyl($C_{2-20}$)carbonyloxy-4,4,4-trifluorobutyl]benzoate,
4-alkyl($C_{3-20}$)carbonyloxyphenyl 4-[4-alkoxyalkyl($C_{2-20}$)carbonyloxy-5,5,5-trifluoropentyl]benzoate,
4-alkyl($C_{3-20}$)carbonyloxyphenyl 4-[5-alkoxyalkyl($C_{2-20}$)carbonyloxy-6,6,6-trifluorohexyl]benzoate,
4-alkyl($C_{3-20}$)carbonyloxyphenyl 4-[6-alkoxyalkyl($C_{2-20}$)carbonyloxy-7,7,7-trifluoroheptyl]benzoate,
4'-alkyl($C_{3-20}$)oxy-4-biphenylyl 4-[2-alkoxyalkyl($C_{2-20}$)carbonyloxy-3,3,3-trifluoropropyl]benzoate,
4'-alkyl($C_{3-20}$)oxy-4-biphenylyl 4-[3-alkoxyalkyl($C_{2-20}$)carbonyloxy-4,4,4-trifluorobutyl]benzoate,
4'-alkyl($C_{3-20}$)oxy-4-biphenylyl 4-[4-alkoxyalkyl($C_{2-20}$)carbonyloxy-5,5,5-trifluoropentyl]benzoate,
4'-alkyl($C_{3-20}$)oxy-4-biphenylyl 4-[5-alkoxyalkyl($C_{2-20}$)carbonyloxy-6,6,6-trifluorohexyl]benzoate,
4'-alkyl($C_{3-20}$)oxy-4-biphenylyl 4-[6-alkoxyalkyl($C_{2-20}$)carbonyloxy-7,7,7-trifluoroheptyl]benzoate,
4'-alkyl($C_{3-20}$)-4-biphenylyl 4-[2-alkoxyalkyl($C_{2-20}$)carbonyloxy-3,3,3-trifluoropropyl]benzoate,
4'-alkyl($C_{3-20}$)-4-biphenylyl 4-[3-alkoxyalkyl($C_{2-20}$)carbonyloxy-4,4,4-trifluorobutyl]benzoate,
4'-alkyl($C_{3-20}$)-4-biphenylyl 4-[4-alkoxyalkyl($C_{2-20}$)carbonyloxy-5,5,5-trifluoropentyl]benzoate,
4'-alkyl($C_{3-20}$)-4-biphenylyl 4-[5-alkoxyalkyl($C_{2-20}$)carbonyloxy-6,6,6-trifluorohexyl]benzoate,
4'-alkyl($C_{3-20}$)-4-biphenylyl 4-[6-alkoxyalkyl($C_{2-20}$)carbonyloxy-7,7,7-trifluoroheptyl]benzoate,
4'-alkyl($C_{3-20}$)oxycarbonyl-4-biphenylyl 4-[2-alkoxyalkyl($C_{2-20}$)carbonyloxy-3,3,3-trifluoropropyl]benzoate,
4'-alkyl($C_{3-20}$)oxycarbonyl-4-biphenylyl 4-[3-alkoxyalkyl($C_{2-20}$)carbonyloxy-4,4,4-trifluorobutyl]benzoate
4'-alkyl($C_{3-20}$)oxycarbonyl-4-biphenylyl 4-[4-alkoxyalkyl($C_{2-20}$)carbonyloxy-5,5,5-trifluoropentyl]benzoate,
4'-alkyl($C_{3-20}$)oxycarbonyl-4-biphenylyl 4-[5-alkoxyalkyl($C_{2-20}$)carbonyloxy-6,6,6-trifluorohexyl]benzoate,
4'-alkyl($C_{3-20}$)oxycarbonyl-4-biphenylyl 4-[6-alkoxyalkyl($C_{2-20}$)carbonyloxy-7,7,7-trifluoroheptyl]benzoate,
4'-alkyl($C_{3-20}$)carbonyloxy-4-biphenylyl 4-[2-alkoxyalkyl($C_{2-20}$)carbonyloxy-3,3,3-trifluoropropyl]benzoate,
4'-alkyl($C_{3-20}$)carbonyloxy-4-biphenylyl 4-[3-alkoxyalkyl($C_{2-20}$)carbonyloxy-4,4,4-trifluorobutyl]benzoate,
4'-alkyl($C_{3-20}$)carbonyloxy-4-biphenylyl 4-[4-alkoxyalkyl($C_{2-20}$)carbonyloxy-5,5,5-trifluoropentyl]benzoate,
4'-alkyl($C_{3-20}$)carbonyloxy-4-biphenylyl 4-[5-alkoxyalkyl($C_{2-20}$)carbonyloxy-6,6,6-trifluorohexyl]benzoate,
4'-alkyl($C_{3-20}$)carbonyloxy-4-biphenylyl 4-[6-alkoxyalkyl($C_{2-20}$)carbonyloxy-7,7,7-trifluoroheptyl]benzoate,
2-[4-[4-[2-alkoxyalkyl($C_{2-20}$)carbonyloxy-3,3,3-trifluoropropyl]phenylcarbonyloxyphenyl]-5-alkyl($C_{3-20}$)oxypyrimidine,
2-[4-[4-[3-alkoxyalkyl($C_{2-20}$)carbonyloxy-4,4,4-trifluorobutyl]phenylcarbonyloxyphenyl]-5-alkyl($C_{3-20}$)oxypyrimidine,
2-[4-[4-[4-alkoxyalkyl($C_{2-20}$)carbonyloxy-5,5,5-trifluoropentyl]phenylcarbonyloxyphenyl]-5-alkyl($C_{3-20}$)oxypyrimidine,
2-[4-[4-[5-alkoxyalkyl($C_{2-20}$)carbonyloxy-6,6,6-trifluorohexyl]phenylcarbonyloxyphenyl]-5-alkyl($C_{3-20}$)oxypyrimidine,
2-[4-[4-[6-alkoxyalkyl($C_{2-20}$)carbonyloxy-7,7,7-trifluoroheptyl]phenylcarbonyloxyphenyl]-5-alkyl($C_{3-20}$)oxypyrimidine,
2-[4-[4-[2-alkoxyalkyl($C_{2-20}$)carbonyloxy-3,3,3-trifluoropropyl]phenylcarbonyloxy]phenyl]-5-alkyl($C_{3-20}$)pyrimidine,
2-[4-[4-[3-alkoxyalkyl($C_{2-20}$)carbonyloxy-4,4,4-trifluorobutyl]phenylcarbonyloxy]phenyl]-5-alkyl($C_{3-20}$)pyrimidine,
2-[4-[4-[4-alkoxyalkyl($C_{2-20}$)carbonyloxy-5,5,5-trifluoropentyl]phenylcarbonyloxy]phenyl]-5-alkyl($C_{3-20}$)pyrimidine,
2-[4-[4-[5-alkoxyalkyl($C_{2-20}$)carbonyloxy-6,6,6-trifluorohexyl]phenylcarbonyloxy]phenyl]-5-alkyl($C_{3-20}$)pyrimidine,
2-[4-[4-[6-alkoxyalkyl($C_{2-20}$)carbonyloxy-7,7,7-trifluoroheptyl]phenylcarbonyloxy]phenyl]-5-alkyl($C_{3-20}$)pyrimidine,
2-[4-[4-[2-alkoxyalkyl($C_{2-20}$)carbonyloxy-3,3,3-trifluoropropyl]phenylcarbonyloxy]phenyl]-5-alkyl($C_{3-20}$)oxycarbonylpyrimidine,
2-[4-[4-[3-alkoxyalkyl($C_{2-20}$)carbonyloxy-4,4,4-trifluorobutyl]phenylcarbonyloxy]phenyl]-5-alkyl($C_{3-20}$)oxycarbonylpyrimidine,
2-[4-[4-[4-alkoxyalkyl($C_{2-20}$)carbonyloxy-5,5,5-trifluoropentyl]phenylcarbonyloxy]phenyl]-5-alkyl($C_{3-20}$)oxycarbonylpyrimidine,
2-[4-[4-[5-alkoxyalkyl($C_{2-20}$)carbonyloxy-6,6,6-trifluorohexyl]phenylcarbonyloxy]phenyl]-5-alkyl($C_{3-20}$)oxycarbonylpyrimidine,
2-[4-[4-[6-alkoxyalkyl($C_{2-20}$)carbonyloxy-7,7,7-trifluoroheptyl]phenylcarbonyloxy]phenyl]-5-alkyl($C_{3-20}$)oxycarbonylpyrimidine,
2-[4-[4-[2-alkoxyalkyl($C_{2-20}$)carbonyloxy-3,3,3-trifluoropropyl]phenylcarbonyloxy]phenyl]-5-alkyl($C_{3-20}$)carbonyloxypyrimidine,
2-[4-[4-[3-alkoxyalkyl($C_{2-20}$)carbonyloxy-4,4,4-trifluorobutyl]phenylcarbonyloxy]phenyl]-5-alkyl($C_{3-20}$)carbonyloxypyrimidine,
2-[4-[4-[4-alkoxyalkyl($C_{2-20}$)carbonyloxy-5,5,5-trifluoropentyl]phenylcarbonyloxy]phenyl]-5-alkyl($C_{3-20}$)carbonyloxypyrimidine,
2-[4-[4-[5-alkoxyalkyl($C_{2-20}$)carbonyloxy-6,6,6-trifluorohexyl]phenylcarbonyloxy]phenyl]-5-alkyl($C_{3-20}$)carbonyloxypyrimidine,
2-[4-[4-[6-alkoxyalkyl($C_{2-20}$)carbonyloxy-7,7,7-trifluoroheptyl]phenylcarbonyloxy]phenyl]-5-alkyl($C_{3-20}$)carbonyloxypyrimidine, etc.

The optically active aromatic compound having a trifluoromethyl group represented by the general formula (1) can be obtained by the process described above. In case of utilizing said compounds as a liquid crystal material, especially as a ferroelectric liquid crystal material, it is preferred, in view of practical optical stability, etc., that $R^2$ in the formula (1) is an alkyl or alkoxyalkyl group which is not substituted with a halogen atom.

In practical use of the compounds, it is also desirable that $R^2$ is an alkyl or alkoxyalkyl group having 1 to 10 carbon atoms as these compounds show the more favorable properties.

As for the substituent $R^1$, it is practically preferred that $R^1$ is an alkyl group with a carbon number of 8 to 16, but this does not apply in case of using the compounds as a component of a liquid crystal material.

Also, when X in the formula (1) is —COO—, the compounds exhibit favorable practical properties.

In ferroelectric liquid crystals in general, it is desirable that the liquid crystal compounds have a large value of spontaneous polarization for exhibiting their meritorious characteristic of high-speed responsiveness. In the optically active aromatic compounds having a trifluoromethyl group represented by the formula (1) according to the present invention, a trifluoromethyl group with a large dipole moment is bonded directly to each asymmetric carbon as a structural feature, so that it is possible to develop a large value of spontaneous polarization in said compounds. This characteristic becomes most remarkable when n in the formula (1) is 0.

The optically active aromatic compounds (1) having a trifluoromethyl group according to the present invention can be used effectively as a component of ferroelectric liquid crystal compositions not only when said compounds assume a liquid crystal phase in themselves but also even when no such liquid crystal phase is generated.

The liquid crystal compositions in accordance with the present invention contain as an essential component thereof at least one of said optically active aromatic compounds having a trifluoromethyl group represented by the formula (1). In said liquid crystal compositions, an optically active aromatic compound (1) having a trifluoromethyl group is contained in an amount of 0.1 to 99.9% by weight, preferably 1 to 99% by weight, based on the obtained composition.

The liquid crystal compositions according to this invention find useful application to various types of liquid crystal elements, for example, optical switching elements. In such applications, said liquid crystal compositions can be used in the ways known in the art.

As described above, the optically active aromatic compounds having a trifluoromethyl group represented by the general formula (1) according to the present invention have very excellent properties as a liquid crystal material and can be used advantageously for the liquid crystal compositions and for the liquid crystal elements using such compositions.

Further, the above-said compounds can be obtained easily in a high yield according to the process of this invention.

DESCRIPTION OF THE PREFERRED EMBODIMENTS

The present invention will hereinafter be described more particularly with reference to the preparation examples for the starting materials and the working examples of the invention. It is to be understood, however, that these examples are merely intended to be illustrative and not to be construed as limiting the scope of the invention.

PREPARATION EXAMPLE 1

2.4 g (0.1 mol) of magnesium chips and 50 ml of anhydrous tetrahydrofuran were placed into a four-necked flask equipped with a thermometer, a dropping funnel and a stirrer. Then a mixture of 2.6 g (10 mmol) of 4-benzyloxybromobenzene and 5 ml of anhydrous tetrahydrofuran and a small quality of iodine were further added to the flask, followed by heating of the flask contents to 60° C. and dropwise addition thereto of a mixture of 23.7 g of 4-benzyloxybromobenzene and 45 ml of anhydrous tetrahydrofuran. Thereafter, the flask contents were stirred under reflux for 2 hours and then cooled to room temperature. The resulting mixture was added dropwise to a mixture of 31.5 g (0.15 mol) of trifluoroacetic anhydride and 150 ml of anhydrous tetrahydrofuran at −78° C. The mixture was stirred at −78° C. for one hour and then heated gradually to −50° C. The mixture was then added with 100 ml of a saturated ammonium chloride solution at −50° C. and then heated to room temperature. The resulting mixture was extracted with 300 ml of ether, and the obtained organic layer was washed successively with a 5% sodium bicarbonate solution, water and brine in that order, then dried over anhydrous magnesium sulfate and concentrated under reduced pressure. The residue was subjected to silica gel column chromatography using a ½ mixture of toluene and hexane as eluent to obtain 18.2 g of 4-benzyloxy-α,α,α-trifluoroacetophenone (5) as a pale yellow solid having a melting point of 58°–60° C. in a yield of 65%.

16.8 g (60 mmol) of this product (5) was dissolved in 150 ml of ethanol, and the solution was added with 1.1 g (30 mmol) of sodium borohydride and stirred at room temperature for 4 hours. The reaction mixture was poured into water and extracted with ethyl acetate. The resultantly formed organic layer was washed with water and brine successively in that order, dried over anhydrous magnesium sulfate and concentrated under reduced pressure to give 16.7 g of 4-benzyloxy-α,α,α-trifluoro-β-phenethyl alcohol (6) as a pale yellow solid. Yield: 99%; m.p. 115°–117° C.

15.5 g (55 mmol) of the product (6) was dissolved in 100 ml of pyridine, and the solution was added with 5.2 g (66 mmol) of acetyl chloride at 0°–5° C. and stirred at the same temperature for 2 hours. The reaction mixture was poured into water and extracted with ethyl acetate, and the resultantly formed organic layer was washed with 10% hydrochloric acid, water, a 5% sodium bicarbonate solution and brine successively in that order, then dried over anhydrous magnesium sulfate and concentrated under reduced pressure to obtain 17.8 g of 4-benzyloxy-1-(1-acetoxy-2,2,2-trifluoroethyl)benzene (7-1) as a pale yellow solid. Yield: 100%; m.p. 85°–87° C.

17.8 g (55 mmol) of the product (7-1) was dissolved in 10 ml of chloroform, and the solution was added with 100 ml of 0.3 M phosphate buffer and 1.8 g of lipase (Amano P) and stirred vigorously at 36°–38° C. for 48 hours. The reaction mixture was filtered and the filtrate was extracted with ethyl acetate. The obtained organic layer was washed with brine, then dried over anhydrous magnesium sulfate and concentrated under reduced pressure. The residue was subjected to silica gel column chromatography (eluent: toluene) to give 9.3 g of (−)-4-benzyloxy-1-(1-acetoxy-2,2,2-trifluoroethyl)- benzene (yield: 52%; $[\alpha]_D^{20} = -33.6°$ (c=1, CHCl$_3$)) and 7.3 g of (+)-4-benzyoxy-α,α,α-trifluoro-β-phenethyl alcohol (8-1) (yield: 47%; $[\alpha]_D^{20} = +16.2°$ (c=1, CHCl$_3$). 8.1 g (25 mmol) of thus obtained (−)-4-benzyoxy-1-(1-acetoxy-2,2,2-trifluoroethyl)benzene was dissolved in 50 ml of methanol, and the solution was added with 20 ml of a 20% sodium hydroxide solution and stirred at room temperature for one hour.

The resulting reaction mixture was poured into water and extracted with ethyl acetate, and the formed organic layer was washed with water and a brine dried over anhydrous magnesium sulfate and concentrated under reduced pressure to obtain 6.9 g of (−)-4-benzyloxy-α,α,α-trifluoro-β-phenethyl alcohol (8-2). Yield: 98%; $[\alpha]_D^{20} = -14.1°$ (c=1, CHCl$_3$).

PREPARATION EXAMPLE 2

1.4 g (5 mmol) of the product (8-1) obtained in Preparation Example 1 was dissolved in 20 ml of dimethylformamide, and the solution was added with 0.24 g (6 mmol) of sodium hydride (content: 60%) and stirred at room temperature for one hour. This was followed by addition of 1.5 g (6 mmol) of n-hexyl p-toluenesulfonate and stirring at room temperature for 3 hours. The reaction mixture was poured into water and extracted with ethyl acetate, and the obtained organic layer was washed with water and brine dried over anhydrous magnesium sulfate and concentrated under reduced pressure. The residue was subjected to silica gel column chromatography (eluent: toluene/hexane (1/1)) to obtain 1.6 g of (+)-4-benzyloxy-1-(1-hexyloxy-2,2,2-trifluoroethyl)benzene (9-1). Yield: 88%; $[\alpha]_D^{20} = +36.6°$ (c=1, CHCl$_3$).

PREPARATION EXAMPLES 3-6

The procedure of Preparation Example 2 was followed except that the alkylating agents (12) shown in Table 1 were used in place of n-hexyl p-toluenesulfonate to obtain the optically active benzyloxybenzene derivatives (9) shown in Table 1.

TABLE 1

| Preparation Example No. | Alkylating agent (12) | Optically active benzyloxybenzene derivatives (9) | | | | |
|---|---|---|---|---|---|---|
| | | p | R$^2$ | Yield (%) | $[\alpha]_D^{20}$ (c = 1, CHCl$_3$) | Symbol |
| 3 | Propyl bromide | 0 | C$_3$H$_7$ | 95 | +42.8° | 9-2 |
| 4 | Pentyl bromide | 0 | C$_5$H$_{11}$ | 92 | +40.1° | 9-3 |
| 5 | Octadecyl p-toluenesulfonate | 0 | C$_{18}$H$_{37}$ | 81 | +23.8° | 9-4 |
| 6 | Ethoxypropyl p-toluenesulfonate | 0 | (CH$_2$)$_3$OC$_2$H$_5$ | 82 | +39.1° | 9-5 |

PREPARATION EXAMPLES 7-9

The procedure of Preparation Example 2 was followed except that the product (8-2) obtained in Preparation Example 1 was used in place of the product (8-1) as starting material, and that the alkylating agents shown in Table 2 were used in place of n-hexyl p-toluenesulfonate. The results are shown in Table 2.

TABLE 2

| Preparation Example No. | Alkylating agent (12) | Optically active benzyloxybenzene derivatives (9) | | | | |
|---|---|---|---|---|---|---|
| | | p | R$^2$ | Yield (%) | $[\alpha]_D^{20}$ (c = 1, CHCl$_3$) | Symbol |
| 7 | Methoxymethyl chloride | 0 | CH$_2$OCH$_3$ | 88 | +45.3° | 9-6 |
| 8 | Methoxyethyl p-toluenesulfonate | 0 | C$_2$H$_4$OCH$_3$ | 92 | +39.8° | 9-7 |
| 9 | Decyloxymethyl p-toluenesulfonate | 0 | CH$_2$OC$_{10}$H$_{21}$ | 83 | +24.7° | 9-8 |

PREPARATION EXAMPLE 10

0.85 g (3 mmol) of the product (8-2) obtained in Preparation Example 1 was dissolved in 10 ml of pyridine. The solution was cooled to 0°-5° C., added with 0.48 g (3.6 mmol) of hexanoyl chloride and stirred at the same temperature for 2 hours. The reaction mixture was poured into water and extracted with ethyl acetate. The resultantly formed organic layer was washed with a 10% hydrochloric acid solution, water, a 5% sodium bicarbonate solution and brine successively in that order, then dried over anhydrous magnesium sulfate and concentrated under reduced pressure to yield 1.14 g of (−)-4-benzyloxy-1-(1-hexanoyloxy-2,2,2-trifluoroethyl)benzene (9-9). Yield: 100%; $[\alpha]_D^{20} = -57.0°$ (c=1, CHCl)$_3$

PREPARATION EXAMPLES 11 AND 12

The procedure of Preparation Example 10 was followed except for use of the acylating agents (11) shown in Table 3 in place of hexanoyl chloride used in Preparation Example 1. The results are shown in Table 3.

TABLE 3

| Preparation Example No. | Alkylating agent (12) | Optically active benzyloxybenzene derivatives (9) | | | | |
|---|---|---|---|---|---|---|
| | | p | R$^2$ | Yield (%) | $[\alpha]_D^{20}$ (c = 1, CHCl$_3$) | Symbol |
| 11 | Hexadecanoyl chloride | 1 | C$_{15}$H$_{31}$ | 100 | +38.7° | 9-10 |
| 12 | Methoxybutanoyl chloride | 1 | (CH$_2$)$_3$OCH$_3$ | 100 | +62.3° | 9-11 |

PREPARATION EXAMPLE 13

1.1 g (3 mmol) of the product (9-1) of Preparation Example 2 was dissolved in a mixture of 80 ml of tetrahydrofuran and 20 ml of methanol, and the solution was added with 0.2 g of 10% Pd/C and stirred vigorously under hydrogen pressure of 1-1.2 atm. for 8 hours. After the reaction, Pd/C was filtered out and the filtrate was concentrated to obtain 0.82 g of (+)-4-(1-hexyloxy-2,2,2-trifluoroethyl)phenol (3-1). Yield: 99%; $[\alpha]_D^{20} = +44.0°$ (c=1, CHCl$_3$).

PREPARATION EXAMPLES 4-23

The procedure of Preparation Example 13 was followed except the optically active benzyloxybenzene derivatives (9) obtained in Preparation Examples 3-12 were used in place of the compound (9-1) used as starting material in Preparation Example 13. The results are shown in Table 4.

TABLE 4

| Preparation Example No. | Starting optically active benzyloxybenzene derivative (9) | p | R² | Yield (%) | $[\alpha]_D^{20}$ (c = 1, CHCl$_3$) | Symbol |
|---|---|---|---|---|---|---|
| 14 | 9-2 | 0 | C$_3$H$_7$ | 100 | +53.8° | 3-2 |
| 15 | 9-3 | 0 | C$_5$H$_{11}$ | 100 | +46.0° | 3-3 |
| 16 | 9-4 | 0 | C$_{18}$H$_{37}$ | 98 | +31.2° | 3-4 |
| 17 | 9-5 | 0 | (CH$_2$)$_3$OC$_2$H$_5$ | 98 | +54.6° | 3-5 |
| 18 | 9-6 | 0 | CH$_2$OCH$_3$ | 99 | −78.5° | 3-6 |
| 19 | 9-7 | 0 | C$_2$H$_4$OCH$_3$ | 98 | −72.0° | 3-7 |
| 20 | 9-8 | 0 | CH$_2$OC$_{10}$H$_{21}$ | 100 | −38.9° | 3-8 |
| 21 | 9-9 | 1 | C$_5$H$_{11}$ | 100 | −64.5° | 3-9 |
| 22 | 9-10 | 1 | C$_{15}$H$_{31}$ | 97 | −39.5° | 3-10 |
| 23 | 9-11 | 1 | (CH$_2$)$_3$OCH$_3$ | 100 | −62.8° | 3-11 |

PREPARATION EXAMPLE 24

Into a four-necked flask equipped with a thermometer, a dropping funnel and a stirrer, 4.8 g (0.2 mol) of magnesium flasks and 100 ml of anhydrous tetrahydrofuran were placed, followed by addition of a mixture of 4.0 g (20 mmol) of 1-bromo-3-phenylpropane and 10 ml of anhydrous tetrahydrofuran and a small quantity of iodine, heating of the flask contents to 60° C. and dropwise addition of a mixture of 35.8 g (0.18 mol) of 1-bromo-3-phenylpropane and 90 ml of anhydrous tetrahydrofuran at the same temperature. Thereafter, the mixture was stirred under reflux for 2 hours and then cooled to room temperature. The resulting mixture was added dropwise into a mixture consisting of 31.3 g (0.22 mol) of ethyl trifluoroacetate and 200 ml of anhydrous tetrahydrofuran. Thereafter, the mixture was stirred at −78° C. for 2 hours, then heated gradually to −50° C. and further stirred at the same temperature for 2 hours. Thereafter, 100 ml of 1N hydrochloric acid was added at −50° C., followed by heating to room temperature. The reaction mixture was extracted with 300 ml of ether and the formed organic layer was washed with water, a 5% sodium bicarbonate solution and brine successively in that order, then dried over anhydrous magnesium sulfate and concentrated under reduced pressure. The residue was subjected to silica gel column chromatography (eluent: toluene/hexane (½)) to give 20.3 g of 5-phenyl-1,1,1-trifluoropentane-2-one (14-1) in a yield of 47%.

19.5 g (90 mmol) of said product (14-1) was dissolved in 200 ml of ethanol, and the solution was added with 1.7 g (45 mmol) of sodium borohydride and stirred at room temperature for 2 hours. The reaction mixture was poured into water and extracted with ethyl acetate, and the resultantly formed organic layer was washed with water and brine successively, then dried over anhydrous magnesium sulfate and concentrated under reduced pressure to obtain 19.1 g of 5-phenyl-1,1,1-trifluoro-2-pentanol (15-1) as a colorless liquid. Yield: 97%.

18.5 g (85 mmol) of the above product (15-1) was dissolved in 100 ml of pyridine, then added with 7.1 g (90 mmol) of acetyl chloride at 0°-5° C. and stirred at the same temperature for 2 hours. The reaction mixture was poured into water and extracted with ethyl acetate. The resulting organic layer was washed with 10% hydrochloric acid, water, a 5% sodium bicarbonate solution and brine successively in that order, then dried over anhydrous magnesium sulfate and concentrated under reduced pressure to obtain 21.7 g of 2-acetoxy-5-phenyl-1,1,1-trifluoropentane (16-1) as a pale yellow liquid. Yield: 98%.

In a separate operation, 21.3 g (0.16 mol) of aluminum chloride and 200 ml of anhydrous dichloromethane were placed into a four-necked flask provided with a thermometer, a dropping funnel and a stirrer, followed by addition of 12.6 g (0.16 mol) of acetyl chloride and one-hour stirring at room temperature.

This mixture was cooled to 0°-5° C. and added dropwise with a mixture of 20.8 g (80 mmol) of the above product (16-1) and 100 ml of anhydrous dichloromethane at the same temperature. Thereafter, the whole mixture was stirred at the same temperature for 5 hours. The resulting reaction mixture was poured into water and extracted with ethyl acetate, and the obtained organic layer was washed with 10% hydrochloric acid, water, a 5% sodium bicarbonate solution and brine successively in that order, then dried over anhydrous magnesium sulfate and concentrated under reduced pressure. The residue was subjected to silica gel column chromatography (eluent: toluene/hexane (2/1)) to obtain 20.1 g of 4-(4-acetoxy5,5,5-trifluoropentyl)acetophenone (17-1) in a yield of 83%.

19.6 g (65 mmol) of the product (17-1) was dissolved in 10 ml of chloroform, and the solution was added with 300 ml of a 0.3 M phosphate buffer and 2.0 g of lipase (Amano Lipase P) and stirred vigorously at 36°-38° C. for 36 hours.

The reaction mixture was filtered and the filtrate was extracted with ethyl acetate. The organic layer was washed with brine dried over anhydrous magnesium sulfate and concentrated under reduced pressure. The residue was subjected to silica gel column chromatography using toluene as eluent to obtain 8.1 g of (−)-4-(4-hydroxy-5,5,5-trifluoropentyl)acetophenone (18-1) (yield: 48%; $[\alpha]_D^{20} = -3.6°$ (c=1, CHCl$_3$)) and 9.8 g of (−)-4-(4-acetoxy-5,5,5-trifluoropentyl)acetophenone (18-2) (yield: 50%; $[\alpha]_D^{20} = -4.1°$ (c=1, CHCl$_3$)).

PREPARATION EXAMPLES 25 AND 26

The procedure of Preparation Example 24 was followed except for use of 1-bromo-2-phenylethane or 1-bromo-4-phenylbutane in place of 1-bromo-3-phenylpropane as starting material. The results are shown in Table 5.

propoxy-5,5,5-trifluoropentyl)-1-acetoxybenzene (26-1). Yield: 98%; $[\alpha]_D^{20} = +2.6°$ (c=1, CHCl$_3$).

0.60 g (1.9 mmol) of said product (26-1) was dissolved in 10 ml of methanol, and the solution was added with 1.5 ml of a 10% sodium hydroxide solution and stirred at room temperature for one hour.

To the reaction mixture, 1N hydrochloric acid was added until the pH of the mixture became 1-2, and then it was extracted with ethyl acetate. The resultantly

TABLE 5

| Preparation Example No. | Starting material | Ketone compound (14) | | Alcohol compound (15) | | Ester compound (16) | | | Acetophenone derivative (17) | | | Optically active acetophenone derivative (18) | | | | |
|---|---|---|---|---|---|---|---|---|---|---|---|---|---|---|---|---|
| | | n | Yield (%) | n | Yield (%) | n | R$^3$ | Yield (%) | n | R$^3$ | Yield (%) | n | R$^4$ | Yield (%) | $[\alpha]_D^{20}$ (c = 1, CHCl$_3$) | Symbol |
| 25 | 1-bromo-2-phenylethane | 2 | 62 | 2 | 98 | 2 | CH$_3$ | 98 | 2 | CH$_3$ | 85 | 2 | H | 47 | −12.1° | 18-3 |
| | | | | | | | | | | | | 2 | COCH$_3$ | 50 | −18.3° | 18-4 |
| 26 | 1-bromo-4-phenylbutane | 4 | 53 | 4 | 96 | 4 | CH$_3$ | 99 | 4 | CH$_3$ | 82 | 4 | H | 45 | −3.1° | 18-5 |
| | | | | | | | | | | | | 4 | COCH$_3$ | 52 | −3.8° | 18-6 |

PREPARATION EXAMPLE 27

A mixture consisting of 1.3 g (5 mmol) of the product (18-1) obtained in Preparation Example 24, 8.5 g (50 mmol) of propyl iodide and 3.5 g (15 mmol) of silver oxide was stirred vigorously at room temperature for 48 hours, with the light shielded. The reaction mixture was filtered and the filtered substance was washed with 50 ml of ethyl acetate. The filtrate joined with the washings was concentrated under reduced pressure and the residue was subjected to silica gel column chromatography using toluene as eluent to give 1.3 g of (−)-4-(4-propoxy-5,5,5-trifluoropentyl)acetophenone (25-1). Yield: 86%; $[\alpha]_D^{20} = -2.7°$ (c=1, CHCl$_3$).

formed organic layer was washed with water, a 5% sodium bicarbonate solution and brine in that order, then dried over anhydrous magnesium sulfate and concentrated under reduced pressure to give 0.51 g of (−)-4-(4-propoxy-5,5,5-trifluoropentyl)phenol (3-14). Yield: 100%; $[\alpha]_D^{20} = -3.0°$ (c=1, CHCl$_3$).

PREPARATION EXAMPLES 28-35

The procedure of Preparation Example 27 was followed except that the optically active acetophenone derivatives (18) and alkylating agents (12) shown in Table 6 were used in place of the product (18-1) and alkylating agent used in Preparation Example 27. The results are shown in Table 6.

TABLE 6

| Preparation Example No | Starting optically active acetophenone derivative (18) | Starting alkylating agent (12) | n | R$^2$ | Optically active acetophenone derivative (25) | | | Optically active acetoxybenzene derivative (26) | | | Optically active phenol derivative (3) | | |
|---|---|---|---|---|---|---|---|---|---|---|---|---|---|
| | | | | | Yield (%) | $[\alpha]_D^{20}$ (c = 1, CHCl$_3$) | Symbol | Yield (%) | $[\alpha]_D^{20}$ (c = 1, CHCl$_3$) | Symbol | Yield (%) | $[\alpha]_D^{20}$ (c = 1, CHCl$_3$) | Symbol |
| 28 | 18-1 | Ethyl iodide | 3 | C$_2$H$_5$ | 92 | −3.1° | 25-2 | 98 | +2.9° | 26-2 | 99 | −3.6° | 3-15 |
| 29 | 18-1 | Pentyl iodide | 3 | C$_5$H$_{11}$ | 81 | −2.4° | 25-3 | 98 | +2.2° | 26-3 | 100 | −2.7° | 3-16 |
| 30 | 18-3 | Propyl iodide | 2 | C$_3$H$_7$ | 88 | −7.8° | 25-4 | 97 | +7.0° | 26-4 | 98 | −11.8° | 3-17 |
| 31 | 18-3 | Butyl iodide | 2 | C$_4$H$_9$ | 85 | −7.0° | 25-5 | 96 | +6.3 | 26-5 | 99 | −10.6° | 3-18 |
| 32 | 18-3 | Pentyl iodide | 2 | C$_5$H$_{11}$ | 78 | −6.3° | 25-6 | 98 | +5.8° | 26-6 | 99 | −9.8° | 3-19 |
| 33 | 18-5 | Ethyl iodide | 4 | C$_2$H$_5$ | 91 | −2.7° | 25-7 | 99 | +2.6° | 26-7 | 98 | −3.3° | 3-20 |
| 34 | 18-5 | Propyl iodide | 4 | C$_3$H$_7$ | 85 | −2.5° | 25-8 | 98 | +2.3° | 26-8 | 98 | −2.5° | 3-21 |
| 35 | 18-5 | Pentyl iodide | 4 | C$_5$H$_{11}$ | 79 | −2.0° | 25-9 | 97 | +1.7° | 26-9 | 97 | −2.2° | 3-22 |

0.60 g (2 mmol) of the product (25-1) was dissolved in 10 ml of dichloromethane, and the solution was added with 0.52 g (3 mmol) of m-chloroperbenzoic acid and stirred at room temperature for 24 hours. The reaction mixture was added with 20 ml of a 5% sodium hydrogen sulfite solution, stirred for 30 minutes and then extracted with ethyl acetate. The obtained organic layer was washed with water, a 5% sodium bicarbonate solution and brine successively in that order, then dried over anhydrous magnesium sulfate and concentrated under reduced pressure to obtain 0.61 g of (+)-4-(4-

PREPARATION EXAMPLE 36

9.1 g (30 mmol) of the product (18-2) obtained in Preparation Example 24 was dissolved in 50 ml of dichloromethane, and the solution was added with 7.8 g (45 mmol) of m-chloroperbenzoic acid and stirred at room temperature for 36 hours. The reaction mixture was diluted with 150 ml of ethyl acetate, washed with a 10% sodium hydrogen sulfite solution, water, a 5% sodium bicarbonate solution and brine successively in that order, then dried over anhydrous magnesium sulfate and concentrated under reduced pressure to obtain 9.1 g of (+)-(4-acetoxy-5,5,5-trifluoropentyl)-1-

26 was used in place of the product (18-2) as starting material. The results are shown in Table 7.

TABLE 7

| Preparation Example No | Starting optically active acetophenone derivative (18) | Optically active acetoxybenzene derivative (19) | | | |
|---|---|---|---|---|---|
| | | n | $R^4$ | Yield (%) | $[\alpha]_D^{20}$ (c = 1, CHCl$_3$) |
| 37 | 18-4 | 2 | COCH$_3$ | 97 | +15.2° |
| 38 | 18-6 | 4 | COCH$_3$ | 95 | +3.0° |

| Preparation Example No. | Optically active diol (20) | | | Optically active alcohol (21) | | | |
|---|---|---|---|---|---|---|---|
| | n | Yield (%) | $[\alpha]_D^{20}$ (c = 1, CHCl$_3$) | n | Yield (%) | $[\alpha]_D^{20}$ (c = 1, CHCl$_3$) | Symbol |
| 37 | 2 | 100 | +18.9° | 2 | 95 | +14.4° | 21-2 |
| 38 | 4 | 98 | +4.6° | 4 | 94 | +3.2° | 21-3 | acetoxybenzene (19-1) Yield: 96%; $[\alpha]_D^{20} = +3.1°$ (c=1, CHCl$_3$).

8.9 g (28 mmol) of the above product (19-1) was dissolved in 30 ml of methanol, added with a 10% sodium hydroxide solution and stirred at room temperature for 3 hours.

After completion of the reaction, 1N hydrochloric acid was added to the reaction mixture until its pH became 1-2, and then it was extracted with ethyl acetate. The resultantly formed organic layer was washed with water, a 5% sodium bicarbonate solution and brine successively in that order, then dried over anhydrous magnesium sulfate and concentrated under reduced pressure to obtain 6.4 g of (+)-(4-hydroxy-5,5,5-trifluoropentyl)phenol (20-1). Yield: 98%; $[\alpha]_D^{20} = +4.2°$ (c=1, CHCl$_3$).

6.3 g (27 mmol) of the above product (20-1) was dissolved in 50 ml of dimethylformamide, and the solution was added with 5.1 g (40 mmol) of benzyl chloride and 8.3 g (60 mmol) of potassium carbonate and stirred at 50°-60° C. for 5 hours.

The reaction mixture was poured into water and extracted with ethyl acetate. The consequently formed organic layer was washed with water and brine successively in that order, dried over anhydrous magnesium sulfate and concentrated under reduced pressure, and the residue was subjected to silica gel column chromatography using toluene as eluent to give 8.2 g of (+)-4-(4-hydroxy-5,5,5-trifluoropentyl)-1-benzyloxybenzene (21-1). Yield: 94%; $[\alpha]_D^{20} = +2.9°$ (c=1, CHCl$_3$).

PREPARATION EXAMPLES 37 AND 38

The procedure of Preparation Example 36 was followed except that the optically active acetophenone derivative (18) obtained in Preparation Example 25 or

PREPARATION EXAMPLE 39

0.97 g (3 mmol) of the product (21-1) of preparation Example 36 was dissolved in 10 ml of dimethylformamide, and the solution was added with 0.16 g (4 mmol) of sodium hydride (content: 60%) and stirred at room temperature for one hour, followed by further addition of 0.55 g (4 mmol) of butyl bromide and 3 hour stirring at 40°-50° C.

The reaction mixture was poured into water and extracted with ethyl acetate. The resultantly formed organic layer was washed with water and brine then dried over anhydrous magnesium sulfate and concentrated under reduced pressure. The residue was subjected to silica gel column chromatography using a 1/1 mixture of toluene and hexane as eluent to give 1.1 g of (+)-4-(4-butoxy-5,5,5-trifluoropentyl)-1-benzyloxybenzene (22-1). Yield: 93%; $[\alpha]_D^{20} = +2.6°$ (c=1, CHCl$_3$).

PREPARATION EXAMPLES 40-44

The procedure of Preparation Example 39 was followed except that the optically active alcohols (21) and alkylating agents (12) shown in Table 8 were used in place of the compound (21-1) and alkylating agent used in Preparation Example 39. The results are shown in Table 8.

TABLE 8

| Preparation Example No. | Starting optically active alcohol (21) | Alkylating agent (12) | Optically active benzyloxybenzene derivative (22) | | | | | |
|---|---|---|---|---|---|---|---|---|
| | | | n | p | $R^2$ | Yield (%) | $[\alpha]_D^{20}$ (c = 1, CHCl$_3$) | Symbol |
| 40 | 21-1 | Ethoxypropyl p-toluene-sulfonate | 3 | 0 | (CH$_2$)$_3$OC$_2$H$_5$ | 90 | +2.2° | 22-2 |
| 41 | 21-2 | Ethyl bromide | 2 | 0 | C$_2$H$_5$ | 95 | +5.5° | 22-3 |
| 42 | 21-2 | Ethoxypropyl p-toluene-sulfonate | 2 | 0 | (CH$_2$)$_3$OC$_2$H$_5$ | 91 | +4.7° | 22-4 |
| 43 | 21-3 | Butyl bromide | 4 | 0 | C$_4$H$_9$ | 94 | +1.8° | 22-5 |
| 44 | 21-3 | Ethoxypropyl p-toluene-sulfonate | 4 | 0 | (CH$_2$)$_3$OC$_2$H$_5$ | 90 | +1.6° | 22-6 |

PREPARATION EXAMPLE 45

0.97 g (3 mmol) of the product (21-1) of preparation Example 36 was dissolved in 10 ml of pyridine, and the solution was added with 0.37 g (4 mmol) of propanoyl chloride at 0°-5° C. and stirred at the same temperature for 2 hours.

The reaction mixture was poured into water and extracted with ethyl acetate, and the obtained organic layer was washed with 10% hydrochloric acid, water, a 5% sodium bicarbonate solution and brine successively in that order, then dried over anhydrous magnesium sulfate and concentrated under reduced pressure to obtain 1.1 g of (−)-4-(4-propanoyloxy-5,5,5-trifluoropentyl)-1-benzyloxybenzene (22-17) Yield: 97%; $[\alpha]_D^{20} = -3.3°$ (c=1, CHCl$_3$).

40–50 were used in place of the compound (22-1) as starting material. The results are shown in Table 10.

TABLE 10

| Preparation Example No. | Starting optically active benzyloxybenzene derivative (22) | Optically active phenol derivative (3) | | | | | |
|---|---|---|---|---|---|---|---|
| | | n | p | R$^2$ | Yield (%) | $[\alpha]_D^{20}$ (c = 1, CHCl$_3$) | Symbol |
| 52 | 22-2 | 3 | 0 | (CH$_2$)$_3$OC$_2$H$_5$ | 98 | +2.1° | 3-24 |
| 53 | 22-3 | 2 | 0 | C$_2$H$_5$ | 99 | +6.4° | 3-25 |
| 54 | 22-4 | 2 | 0 | (CH$_2$)$_3$OC$_2$H$_5$ | 98 | +5.2° | 3-26 |
| 55 | 22-5 | 4 | 0 | C$_4$H$_9$ | 99 | +2.0° | 3-27 |
| 56 | 22-6 | 4 | 0 | (CH$_2$)$_3$OC$_2$H$_5$ | 97 | +1.9° | 3-28 |
| 57 | 22-7 | 3 | 1 | C$_2$H$_5$ | 100 | −3.7° | 3-29 |
| 58 | 22-8 | 3 | 1 | C$_5$H$_{11}$ | 98 | −3.3° | 3-30 |
| 59 | 22-9 | 2 | 1 | C$_2$H$_5$ | 99 | −17.3° | 3-31 |
| 60 | 22-10 | 2 | 1 | C$_5$H$_{11}$ | 98 | −14.0° | 3-32 |
| 61 | 22-11 | 4 | 1 | C$_2$H$_5$ | 98 | −3.3° | 3-33 |
| 62 | 22-12 | 4 | 1 | C$_5$H$_{11}$ | 99 | −2.9° | 3-34 |

PREPARATION EXAMPLES 46–50

The procedure of Preparation Example 45 was followed except that the optically active alcohols (21) and acylating agents (11) shown in Table 9 were used in place of the compound (21-1) and acylating agent used in Preparation Example 45. The results are shown in Table 9.

TABLE 9

| Preparation Example No. | Starting optically active alcohol (21) | Acylating agent (11) | Optically active benzyloxybenzene derivative (22) | | | | | |
|---|---|---|---|---|---|---|---|---|
| | | | n | p | R$^2$ | Yield (%) | $[\alpha]_D^{20}$ (c = 1, CHCl$_3$) | Symbol |
| 46 | 21-1 | Hexanoyl chloride | 3 | 1 | C$_5$H$_{11}$ | 96 | −2.9° | 22-8 |
| 47 | 21-2 | Propanoyl chloride | 2 | 1 | C$_2$H$_5$ | 98 | −15.1° | 22-9 |
| 48 | 21-2 | Hexanoyl chloride | 2 | 1 | C$_5$H$_{11}$ | 95 | −12.4° | 22-10 |
| 49 | 21-3 | Propanoyl chloride | 4 | 1 | C$_2$H$_5$ | 97 | −3.3° | 22-11 |
| 50 | 21-3 | Hexanoyl chloride | 4 | 1 | C$_5$H$_{11}$ | 96 | −2.5° | 22-12 |

PREPARATION EXAMPLE 51

0.95 g (2.5 mmol) of the product (22-1) of Preparation Example 39 was dissolved in 50 ml of ethanol, and the solution was added with 0.1 g of 10% Pd/C and stirred vigorously under hydrogen pressure of 1–1.2 atm. for 5 hours. After the reaction, Pd/C was filtered out and the filtrate was concentrated under reduced pressure to give 0.72 g of (+)-4-(4-butoxy-5,5,5-trifluoropentyl)-phenol (3-23). Yield: 99%; $[\alpha]D^{20} = -2.9°$ (c=1, CHCl$_3$).

PREPARATION EXAMPLES 52–62

The procedure of Preparation Example 51 was followed except that various types of benzyloxybenzene derivatives (22) obtained in Preparation Examples 40–50 were used in place of the compound (22-1) as starting material. The results are shown in Table 10.

PREPARATION EXAMPLE 63

20 ml of a 20% sodium hydroxide solution was placed into a four-necked flask furnished with a thermometer, a dropping funnel and a stirrer. The solution was cooled to 0°–5° C., added with 2.6 g (16 mmol) of bromine and stirred for 30 minutes while maintaining the same temperature.

The resulting mixture was added dropwise with a mixture of 60 g (2 mmol) of the compound (25-1) obtained in preparation Example 27 and 20 ml of dioxane at 0°–5° C. and then stirred at the same temperature for 8 hours.

The reaction mixture was added with 2.0 g of sodium hydrogen sulfite, stirred for 30 minutes, further added with 10% hydrochloric acid until the pH of the mixture became 1–2, and then extracted with ether. The resultantly formed organic layer was washed with brine dried over anhydrous magnesium sulfate and concentrated under reduced pressure to obtain 0.59 g of (+)-4-(4-propoxy-5,5,5-trifluoropentyl)benzoic acid (28-1). Yield: 98%; $[\alpha]_D^{20} = +4.3°$ (c=1, CHCl$_3$).

PREPARATION EXAMPLES 64–71

The procedure of Preparation for Example 63 was followed except that the optically active acetophenone derivatives (25) obtained in Preparation Examples 28–35 were used in place of the compound (25-1) as starting material. The results are shown in Table 11.

TABLE 11

| Preparation Example No. | Optically active acetophenone derivative (25) | Optically active benzoic derivative (28) | | | | | | |
|---|---|---|---|---|---|---|---|---|
| | | R' | n | p | R$^2$ | Yield (%) | $[\alpha]_D^{20}$ (c = 1, CHCl$_3$) | Symbol |
| 64 | 25-2 | OH | 3 | 0 | C$_2$H$_5$ | 98 | +4.6° | 28-2 |
| 65 | 25-3 | OH | 3 | 0 | C$_5$H$_{11}$ | 97 | +4.0° | 28-3 |

TABLE 11-continued

| Preparation Example No. | Optically active acetophenone derivative (25) | Optically active benzoic derivative (28) | | | | | | |
|---|---|---|---|---|---|---|---|---|
| | | R' | n | p | $R^2$ | Yield (%) | $[\alpha]_D^{20}$ (c = 1, CHCl$_3$) | Symbol |
| 66 | 25-4 | OH | 2 | 0 | $C_3H_7$ | 96 | +8.1° | 28-4 |
| 67 | 25-5 | OH | 2 | 0 | $C_4H_9$ | 98 | +7.3° | 28-5 |
| 68 | 25-6 | OH | 2 | 0 | $C_5H_{11}$ | 99 | +5.9° | 28-6 |
| 69 | 25-7 | OH | 4 | 0 | $C_2H_5$ | 97 | +3.0° | 28-7 |
| 70 | 25-8 | OH | 4 | 0 | $C_3H_7$ | 99 | +2.8° | 28-8 |
| 71 | 25-9 | OH | 4 | 0 | $C_5H_{11}$ | 98 | +2.0° | 28-9 |

EXAMPLE 1

0.28 g (1 mmol) of the product (3-1) of Preparation Example 13, 0.36 g (1.3 mmol) of 4-decyloxybenzoic acid and 10 ml of anhydrous dichloromethane were placed into a four-necked flask equipped with a thermometer and a stirrer. The mixture was further added with 0.25 g (1.2 mmol) of N,N'-dicyclohexylcarbodiimide and 20 mg of 4-pyrrolidinopyridine and stirred at room temperature for 24 hours.

After the reaction, the produced precipitate was filtered out and the filtrate was diluted with 50 ml of toluene, washed with water, 5% acetic acid, water, a 5% sodium bicarbonate solution and brine successively in that order, then dried over anhydrous magnesium sulfate and concentrated under reduced pressure. The residue was subjected to silica gel column chromatography using a 1/1 mixture of toluene and hexane as eluent to obtain 0.49 g of (+)-4-(1-hexyloxy-2,2,2-trifluoroethyl)phenyl 4-decyloxybenzoate in a yield of 92%.

EXAMPLE 2

0.30 g (1 mmol) of the product (28-1) of Preparation Example 63, 0.33 g (1.3 mmol) of 4-decyloxyphenol and 10 ml of anhydrous dichloromethane were placed into a four-necked flask equipped with a thermometer and a stirrer. The mixture was further added with 0.25 g (1.2 mmol) of N,N'-dicyclohexylcarbodiimide and 20 mg of 4-pyrrolidinopyridine and stirred at room temperature for 24 hours.

The reaction mixture was subjected to the same aftertreatments as conducted in Example 1 to obtain 0.49 g of (+)-4-decyloxyphenyl 4-(4-propoxy-5,5,5-trifluoropentyl)benzoate (yield: 93%).

EXAMPLE 3-57

The procedure of Example 1 or Example 2 was followed except for use of the starting materials shown in Table 12. The results are shown in Table 12.

TABLE 12

| Example | Starting compound (2) or (28) | | | | Starting optically active compound (3) or (27) | | | | Optically active aromatic compound having trifluoromethyl group (1) | | | | |
|---|---|---|---|---|---|---|---|---|---|---|---|---|---|
| | $R^1$ | Y | k | Ar | n | p | $R^2$ | | $R^1$ | Y | k | Ar | |
| 1 | $C_{10}H_{21}$ | O | 1 | 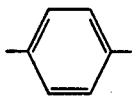 | 0 | 0 | $C_6H_{13}$ | | $C_{10}H_{21}$ | O | 1 |  | |
| 2 | " | " | 1 | " | 3 | 0 | $C_3H_7$ | | " | " | 1 | " | |
| 3 | " | " | 1 | " | 0 | 0 | " | | " | " | 1 | " | |
| 4 | " | " | 1 | " | 0 | 0 | $C_5H_{11}$ | | " | " | 1 | " | |
| 5 | " | " | 1 | " | 0 | 0 | $(CH_2)_3OC_2H_5$ | | " | " | 0 | " | |
| 6 | " | " | 1 | " | 0 | 1 | $C_5H_{11}$ | | " | " | 1 | " | |
| 7 | $C_8H_{17}$ | O | 1 | 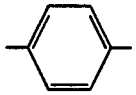 | 0 | 0 | $C_6H_{13}$ | | $C_8H_{17}$ | O | 1 |  | |
| 8 | $C_{10}H_{21}$ | — | 0 | " | 0 | 0 | " | | $C_{10}H_{21}$ | — | 0 | " | |
| 9 | $C_{16}H_{33}$ | O | 1 | " | 0 | 0 | $C_3H_7$ | | $C_{16}H_{33}$ | O | 1 | " | |
| 10 | $C_{10}H_{21}$ | " | 1 | 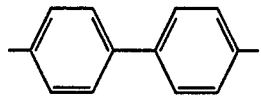 | 0 | 0 | $C_6H_{13}$ | | $C_{10}H_{21}$ | " | 1 | 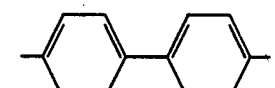 | |
| 11 | $C_9H_{19}$ | — | 0 | " | 0 | 0 | " | | $C_9H_{19}$ | — | 0 | " | |
| 12 | $C_8H_{17}$ | O | 1 | 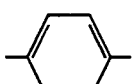 | 0 | 1 | $C_5H_{11}$ | | $C_8H_{17}$ | O | 1 |  | |

TABLE 12-continued

| # | | | | (ring1) | | | | | | (ring2) |
|---|---|---|---|---|---|---|---|---|---|---|
| 13 | C₁₀H₂₁ | O | 1 | 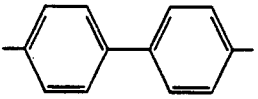 | 0 | 1 | C₅H₁₁ | C₁₀H₂₁ | O | 1 | 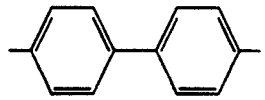 |
| 14 | C₉H₁₉ | — | 0 | " | 0 | 1 | " | C₉H₁₉ | — | 0 | " |
| 15 | C₁₀H₂₁ | O | 1 | " | 0 | 0 | (CH₂)₃OC₂H₅ | C₁₀H₂₁ | O | 1 | " |
| 16 | C₉H₁₉ | — | 0 | " | 0 | 0 | " | C₉H₁₉ | — | 0 | " |
| 17 | C₁₀H₂₁ | O | 1 | 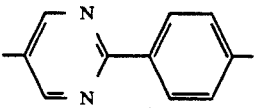 | 0 | 0 | C₆H₁₃ | C₁₀H₂₁ | O | 1 | 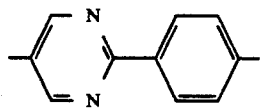 |
| 18 | " | " | 1 | " | 0 | 1 | C₅H₁₁ | " | " | 1 | " |
| 19 | " | " | 1 | " | 0 | 0 | (CH₂)₃OC₂H₅ | " | " | 1 | " |
| 20 | " | " | 1 | 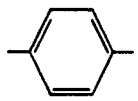 | 3 | 0 | C₃H₇ | " | " | 1 | 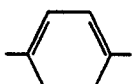 |
| 21 | C₁₂H₂₅ | O | 1 | 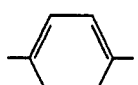 | 3 | 0 | C₃H₇ | C₁₂H₂₅ | O | 1 | |
| 22 | C₁₀H₂₁ | " | 1 | " | 3 | 0 | C₂H₅ | C₁₀H₂₁ | " | 1 | " |
| 23 | C₁₀H₂₁ | — | 0 | 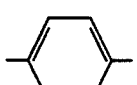 | 3 | 0 | C₂H₅ | C₁₀H₂₁ | — | 0 | 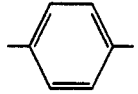 |
| 24 | C₈H₁₇ | O | 1 | " | 3 | 0 | C₅H₁₁ | C₈H₁₇ | O | 1 | " |
| 25 | C₁₀H₂₁ | " | 1 | " | 3 | 0 | C₄H₉ | C₁₀H₂₁ | " | 1 | " |
| 26 | C₁₂H₂₅ | — | 0 | 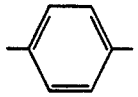 | 3 | 0 | C₄H₉ | C₁₂H₂₅ | — | 0 | 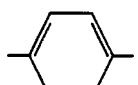 |
| 27 | C₁₀H₂₁ | O | 1 | " | 3 | 0 | (CH₂)₃OC₂H₅ | C₁₀H₂₁ | O | 1 | " |
| 28 | " | " | 1 | " | 3 | 1 | C₂H₅ | " | " | 1 | " |
| 29 | " | " | 1 | 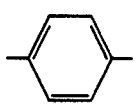 | 3 | 0 | C₃H₇ | " | " | 1 | 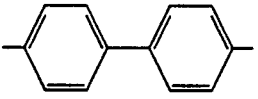 |
| 30 | C₉H₁₉ | — | 0 | " | 3 | 0 | " | C₉H₁₉ | — | 0 | " |
| 31 | C₁₀H₂₁ | O | 1 | " | 3 | 1 | C₂H₅ | C₁₀H₂₁ | O | 1 | " |
| 32 | C₁₂H₂₅ | O | 1 | 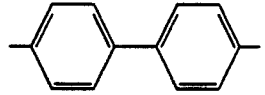 | 3 | 0 | C₃H₇ | C₁₂H₂₅ | O | 1 | 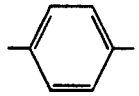 |
| 33 | C₁₀H₂₁ | " | | " | 3 | 0 | C₂H₅ | C₁₀H₂₁ | " | 1 | " |
| 34 | C₁₀H₂₁ | " | 1 | " | 3 | 0 | C₅H₁₁ | C₁₀H₂₁ | " | 1 | " |
| 35 | " | — | 0 | " | 3 | 0 | " | " | — | 0 | " |
| 36 | C₈H₁₇ | O | 1 | 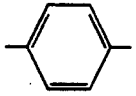 | 3 | 0 | C₃H₇ | C₈H₁₇ | O | 1 | 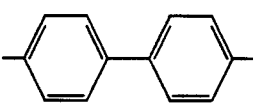 |
| 37 | C₁₂H₂₅ | " | 1 | " | 3 | 0 | " | C₁₂H₂₅ | " | 1 | " |

TABLE 12-continued

| | | | | | | | | | | | |
|---|---|---|---|---|---|---|---|---|---|---|---|
| 38 | C₉H₁₉ | — | 0 | 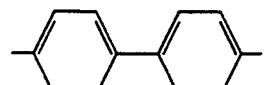 | 3 | 0 | C₅H₁₁ | C₉H₁₉ | — | 0 | 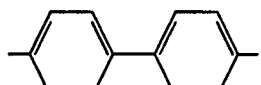 |
| 39 | C₁₀H₂₁ | O | 1 | 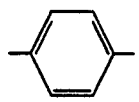 | 2 | 0 | C₂H₅ | C₁₀H₂₁ | O | 1 | 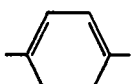 |
| 40 | C₁₂H₂₅ | " | 1 | " | 2 | 0 | " | C₁₂H₂₅ | " | 1 | " |
| 41 | C₁₀H₂₁ | " | 1 | " | 2 | 0 | C₃H₇ | C₁₀H₂₁ | " | 1 | " |
| 42 | C₁₂H₂₅ | " | 1 | " | 2 | 0 | " | C₁₂H₂₅ | " | 1 | " |
| 43 | C₁₀H₂₁ | O | 1 | 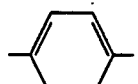 | 2 | 0 | C₄H₉ | C₁₀H₂₁ | O | 1 | 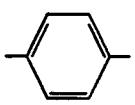 |
| 44 | " | " | 1 | " | 2 | 0 | C₅H₁₁ | " | " | 1 | " |
| 45 | " | " | 1 | " | 2 | 0 | (CH₂)₃OC₂H₅ | " | " | 1 | " |
| 46 | " | " | 1 | " | 2 | 1 | C₂H₅ | " | " | 1 | " |
| 47 | C₁₀H₂₁ | O | 1 | 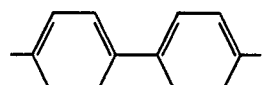 | 2 | 0 | C₅H₁₁ | C₁₀H₂₁ | O | 1 | 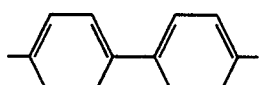 |
| 48 | " | " | 1 | 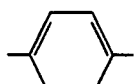 | 4 | 0 | " | " | " | 1 | 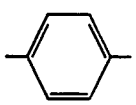 |
| 49 | C₁₂H₂₅ | " | 1 | " | 4 | 0 | C₂H₅ | C₁₂H₂₅ | " | 1 | " |
| 50 | " | " | 1 | " | 4 | 0 | C₃H₇ | " | " | 1 | " |
| 51 | C₁₂H₂₅ | O | 1 | 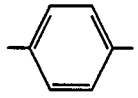 | 4 | 0 | C₄H₉ | C₁₂H₂₅ | O | 1 | 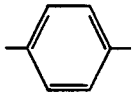 |
| 52 | C₁₀H₂₁ | " | 1 | " | 4 | 1 | C₂H₅ | C₁₀H₂₁ | " | 1 | " |
| 53 | " | " | 1 | " | 4 | 0 | (CH₂)₃OC₂H₅ | " | " | 1 | " |
| 54 | " | " | 1 | 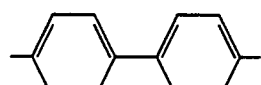 | 4 | 0 | C₃H₇ | " | " | 1 | 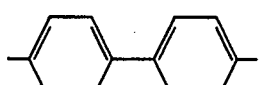 |
| 55 | C₁₀H₂₁ | O | 1 | 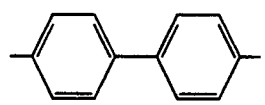 | 4 | 0 | (CH₂)₃OC₂H₅ | C₁₀H₂₁ | O | 1 | 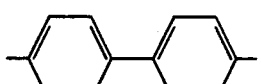 |
| 56 | " | " | 1 | 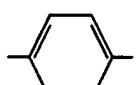 | 4 | 0 | C₃H₇ | " | " | 1 | 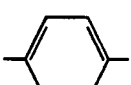 |
| 57 | " | " | 1 | 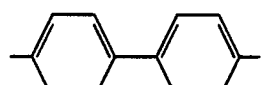 | 4 | 0 | " | " | " | 1 | 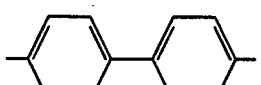 |

| | | | | | Optically active aromatic compound having trifluoromethyl group (1) | | |
|---|---|---|---|---|---|---|---|
| Example | X | n | p | R² | Yield (%) | [α]$_D^{20}$ (c = 1, CHCl₃) | Phase system (°C.) |
| 1 | COO | 0 | 0 | C₆H₁₃ | 92 | +23.1° | K —33— I |
| 2 | OCO | 3 | 0 | C₃H₇ | 93 | +2.1° | K —35— I |

TABLE 12-continued

| No. | Group | n1 | n2 | R | Yield | Rotation | Phase transitions |
|---|---|---|---|---|---|---|---|
| 3 | COO | 0 | 0 | " | 94 | +28.6° | |
| 4 | " | 0 | 0 | $C_5H_{11}$ | 92 | +21.7° | |
| 5 | " | 0 | 0 | $(CH_2)_3OC_2H_5$ | 91 | +26.6° | K —11— I |
| 6 | " | 0 | 1 | $C_5H_{11}$ | 94 | −34.2° | K —51— I |
| 7 | COO | 0 | 0 | $C_6H_{13}$ | 93 | +24.7° | K —34— I |
| 8 | " | 0 | 0 | " | 92 | +23.1° | |
| 9 | " | 0 | 0 | $C_3H_7$ | 94 | +19.5° | |
| 10 | " | 0 | 0 | $C_6H_{13}$ | 95 | +18.6° | K —16— Sc* —83— $S_A$ —92— I |
| 11 | " | 0 | 0 | " | 92 | +19.4° | $S_1$ —7— Sc* —40— $S_A$ —58— I |
| 12 | " | 0 | 1 | $C_5H_{11}$ | 92 | −36.1° | K —63— I |
| 13 | COO | 0 | 1 | $C_5H_{11}$ | 93 | −20.8° | K —94— I, 71 \ $S_A$ —76— Ch / 90 |
| 14 | " | 0 | 1 | " | 93 | −23.0° | K —71— I, 47 \ $S_A$ —52— Ch / 59 |
| 15 | " | 0 | 0 | $(CH_2)_3OC_2H_5$ | 89 | +16.8° | K —48— $S_1$ —55— Sc* —61— $S_A$ —83— Ch —84— I |
| 16 | " | 0 | 0 | " | 91 | +17.3° | K —55— I, 14 \ Sc* —27— $S_A$ —48— Ch / 52 |
| 17 | " | 0 | 0 | $C_6H_{13}$ | 93 | +15.9° | K —78— $S_A$ —85— Ch —88— I, 52 \ Sc* / 65 |
| 18 | " | 0 | 1 | $C_5H_{11}$ | 94 | −20.8° | $S_1$ —56— Sc* —63— $S_A$ —77— Ch —80— I |
| 19 | " | 0 | 0 | $(CH_2)_3OC_2H_5$ | 91 | +15.4° | K —87— Ch —88— I, 58 \ Sc* —65— $S_A$ / 74 |
| 20 | " | 3 | 0 | $C_3H_7$ | 91 | −1.4° | K —29— I, −1 \ $S_A$ —5— Ch / 15 |
| 21 | COO | 3 | 0 | $C_3H_7$ | 93 | −1.3° | K —39— I, 1 \ Sc* —7— $S_A$ —11— Ch / 20 |
| 22 | " | 3 | 0 | $C_2H_5$ | 94 | −1.7° | |
| 23 | " | 3 | 0 | $C_2H_5$ | 94 | −1.7° | |
| 24 | " | 3 | 0 | $C_5H_{11}$ | 94 | −1.3° | |
| 25 | " | 3 | 0 | $C_4H_9$ | 93 | +1.3° | K —4— $S_A$ —5— I |
| 26 | COO | 3 | 0 | $C_4H_9$ | 91 | +1.2° | |
| 27 | " | 3 | 0 | $(CH_2)_3OC_2H_5$ | 90 | +1.0° | |
| 28 | " | 3 | 1 | $C_2H_5$ | 93 | −1.6° | |
| 29 | " | 3 | 0 | $C_3H_7$ | 90 | −0.9° | |
| 30 | " | 3 | 0 | " | 92 | −1.0° | |

TABLE 12-continued

| | | | | | | | Phase sequence |
|---|---|---|---|---|---|---|---|
| 31 | " | 3 | 1 | $C_2H_5$ | 90 | −1.2° | |
| 32 | OCO | 3 | 0 | $C_3H_7$ | 89 | +1.9° | |
| 33 | " | 3 | 0 | $C_2H_5$ | 91 | +2.2° | |
| 34 | " | 3 | 0 | $C_5H_{11}$ | 90 | +1.7° | |
| 35 | " | 3 | 0 | " | 92 | +1.7° | |
| 36 | " | 3 | 0 | $C_3H_7$ | 92 | +1.1° | |
| 37 | " | 3 | 0 | " | 90 | +0.9° | |
| 38 | OCO | 3 | 0 | $C_5H_{11}$ | 90 | +1.0° | |
| 39 | COO | 2 | 0 | $C_2H_5$ | 93 | +3.1° | K —40— I, Sc* —6— $S_A$ —12— Ch, 1, 13 |
| 40 | " | 2 | 0 | " | 94 | +2.9° | K —44— I, 16 \ $S_A$ / 17 |
| 41 | " | 2 | 0 | $C_3H_7$ | 92 | −4.8° | K —36— I, −7 \ Sc* —1— $S_A$ / 6 |
| 42 | " | 2 | 0 | " | 92 | −4.4° | K —40— I, 9 \ Sc* / 10 |
| 43 | COO | 2 | 0 | $C_4H_9$ | 94 | −3.6° | −4 $S_2$ 23; $S_1$ I; −19 \ Sc* —$S_A$— / 1, −3 |
| 44 | " | 2 | 0 | $C_5H_{11}$ | 90 | −3.4° | K —22— I, −26 \ Sc* / −5 |
| 45 | " | 2 | 0 | $(CH_2)_3OC_2H_5$ | 88 | +2.5° | K —−6— I, −22 \ $S_1$ —Sc*— / −14, −19 |
| 46 | " | 2 | 1 | $C_2H_5$ | 93 | −7.8° | $S_1$ —52— I, −6 \ Sc* —Ch— / 6, 0 |
| 47 | COO | 2 | 0 | $C_5H_{11}$ | 91 | −2.9° | $S_2$ —42— Sc* —83— $S_A$ —108— Ch —118— I; 17 \ $S_1$ / 32 |
| 48 | " | 4 | 0 | " | 94 | −1.1° | K —33— I, −5 \ Sc* —$S_A$— / 12, −4 |
| 49 | " | 4 | 0 | $C_2H_5$ | 92 | −1.6° | K —37— I, 13 \ Sc* —$S_A$— / 30, 23 |
| 50 | " | 4 | 0 | $C_3H_7$ | 89 | −1.3° | K —32— I, 16 \ Sc* —$S_A$— / 23, 17 |

TABLE 12-continued

| | | | | | | | |
|---|---|---|---|---|---|---|---|
| 51 | COO | 4 | 0 | $C_4H_9$ | 91 | +0.9° | K —32— I, 7 \ Sc* —14— $S_A$ / 18 |
| 52 | " | 4 | 1 | $C_2H_5$ | 91 | −1.6° | K —25— I, −11 \ Sc* —6— $S_A$ / 14 |
| 53 | " | 4 | 0 | $(CH_2)_3OC_2H_5$ | 92 | +0.8° | $S_2$ —25— $S_1$ —−3— $S_A$ —8— I, −21 \ Sc* / −6 |
| 54 | " | 4 | 0 | $C_3H_7$ | 90 | −1.0° | $S_2$ —53— $S_1$ —70— Sc* —99— $S_A$ —133— I |
| 55 | COO | 4 | 0 | $(CH_2)_3OC_2H_5$ | 90 | +0.5° | $S_1$ —14— I, −23 \ Sc* —−5— $S_A$ / 4 |
| 56 | OCO | 4 | 0 | $C_3H_7$ | 89 | +1.4° | K —26— I, 3 \ Sc* —6— $S_A$ / 9 |
| 57 | " | 4 | 0 | " | 88 | +0.9° | $S_2$ —73— $S_1$ —76— Sc* —114— Ch —118— I |

Note: $S_1$ and $S_2$ denote unidentified smectic phase.

EXAMPLE 58-62

The liquid crystal compositions shown in Table 13 were prepared by using the specified liquid crystal compounds. For the preparation of each composition, weighed quantities of two specified compounds were put into a sample bottle and mixed while melting them by heating. The liquid crystal elements were produced by using the thus prepared liquid crystal compositions according to the method described below.

Liquid Crystal Element Producing Method

Polyimide type polymer films were formed on a pair of glass substrates provided with transparent electrodes of indium oxide, and said film-coated substrates were rubbed in a given direction with glass fiber (5 μm in diameter) used as spacer to constitute a liquid crystal cell, and said liquid crystal compositions were vacuum encapsulated in the thus formed respective cells to obtain liquid crystal elements.

When these liquid crystal elements were combined with a deflector and an electric field of 20 V was applied thereto, there was observed a change in strength of transmitted light. The values of spontaneous polarization determined at this time (according to Soya-Toya method) are shown in Table 13. The phase series of the respective liquid crystal compositions are also shown in the Table.

As seen from the above results, the optically active aromatic compounds having a trifluoromethyl group (1) according to the present invention, even if not assuming Sc* phase in themselves, can become a ferroelectric liquid crystal material operable in the room temperature region when they are made into a liquid crystal composition, and such a ferroelectric liquid crystal material can induce spontaneous polarization necessary for high-speed response.

TABLE 13

| Example No. | Components of liquid crystal compositions (wt %) | | Phase system (°C.) | Value of spontaneous polarization (nC/cm²) (measuring temp.) |
|---|---|---|---|---|
| 58 | Known compound A<br>Compound of Example 1 | (80)<br>(20) | $S_1$ —8— Sc* —57— I | −13<br>[20° C.] |
| 59 | Known compound A<br>Compound of Example 5 | (80)<br>(20) | $S_1$ —0— Sc* —45— S —57— I | −7<br>[18° C.] |
| 60 | Known compound A<br>Compound of Example 6 | (80)<br>(20) | $S_2$ —1— $S_1$ —18— Sc* —40— S —60— I | 3<br>[22° C.] |
| 61 | Known compound A<br>Compound of Example 8 | (80)<br>(20) | $S_1$ —10— Sc* —31— $S_A$ —58— I | −3<br>[15° C.] |

TABLE 13-continued

| Example No. | Components of liquid crystal compositions (wt %) | Phase system (°C.) | Value of spontaneous polarization (nC/cm²) (measuring temp.) |
|---|---|---|---|
| 62 | Known compound A (80) Compound of Example 25 (20) | $S_2 \xrightarrow{12} S_1 \xrightarrow{62} I$ <br> $\xrightarrow{20} Sc^* \xrightarrow{48} S_A \xrightarrow{62}$ | −2 [27° C.] |

Note:
$S_1$ and $S_2$ denote unidentified smectic phase.

Known Compound A $C_{10}H_{21}O$—⟨⟩—COO—⟨⟩—O(CH$_2$)$_3$CHC$_2$H$_5$
                                            |
                                           CH$_3$
                                            *

$K \xrightarrow{35} Sc^* \xrightarrow{70} S_A \xrightarrow{74} I$     Value of spontaneous
  $\searrow 30$                                      polarization:
   $S_B$                                             ~0 nC/cm²

EXAMPLES 63-82

Among the optically active aromatic compounds having a trifluoromethyl group (1) according to the present invention, those which exhibited Sc* phase in themselves and are shown in Table 14 were used singly for producing the liquid crystal elements according to the method described above, and the values of spontaneous polarization of the produced elements were measured. The results are shown in Table 14.

TABLE 14

| Example No. | Liquid crystal Preparation Example No. | Value of spontaneous polarization (nC/cm²) [Measuring temp.] |
|---|---|---|
| 63 | 10 | −105 [40° C.] |
| 64 | 11 | −27 [20° C.] |
| 65 | 15 | −93 [42° C.] |
| 66 | 16 | −28 [21° C.] |
| 67 | 17 | −119 [57° C.] |
| 68 | 18 | −68 [47° C.] |
| 69 | 19 | −8 [65° C.] |
| 70 | 39 | −6 [4° C.] |
| 71 | 43 | 20 [−7° C.] |
| 72 | 44 | 28 [−14° C.] |
| 73 | 46 | 13 [0° C.] |
| 74 | 47 | 35 [41° C.] |
| 75 | 49 | 5 [17° C.] |
| 76 | 50 | 16 [10° C.] |
| 77 | 51 | −15 [7° C.] |
| 78 | 52 | 20 [−4° C.] |
| 79 | 53 | −24 [−15° C.] |
| 80 | 54 | 13 [75° C.] |
| 81 | 55 | −19 [−16° C.] |
| 82 | 57 | −37 [84° C.] |

EXAMPLES 83-104

Among the liquid crystal elements obtained in Examples 58-82, those shown in Table 15 were combined with a deflector and an electric field of 10 V per 1 μm of element thickness was applied thereto. There was observed a change in strength of transmitted light. Response time was determined from said change in strength of transmitted light. The results are shown in Table 15. These results attest to excellent high-speed response of the liquid crystal materials according to the present invention.

TABLE 15

| Example No. | Example No. involving liquid crystal element used | Response time (μs) [Measuring temp.] |
|---|---|---|
| 83 | 58 | 110 [20° C.] |
| 84 | 62 | 586 [27° C.] |
| 85 | 63 | 66 [40° C.] |
| 86 | 64 | 23 [20° C.] |
| 87 | 65 | 65 [37° C.] |
| 88 | 66 | 14 [21° C.] |
| 89 | 67 | 10 [56° C.] |
| 90 | 68 | 31 [47° C.] |
| 91 | 69 | 34 [65° C.] |
| 92 | 70 | 586 [4° C.] |
| 93 | 71 | 566 [−7° C.] |
| 94 | 72 | 546 [−11° C.] |
| 95 | 73 | 625 [0° C.] |
| 96 | 74 | 121 [41° C.] |
| 97 | 75 | 292 [17° C.] |
| 98 | 76 | 81 [10° C.] |
| 99 | 77 | 39 [7° C.] |
| 100 | 78 | 165 [1° C.] |
| 101 | 79 | 175 [−10° C.] |
| 102 | 80 | 18 [75° C.] |
| 103 | 81 | 298 [−9° C.] |
| 104 | 82 | 21 [84° C.] |

What is claimed is:

1. Optically active aromatic compounds having a trifluoromethyl group represented by the following formula:

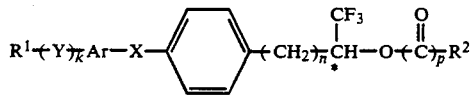

wherein R¹ is an alkyl group having 3-20 carbon atoms; R² is an alkyl or alkoxyalkyl group having 1-20 carbon atoms which may be substituted with a halogen atom; k is a number of 0 or 1; n is an integer of 0-5; p is a number of 0 or 1; Ar is

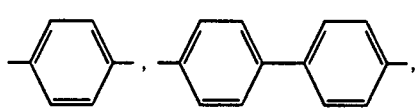

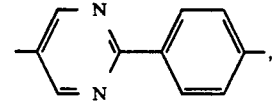

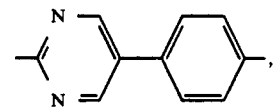

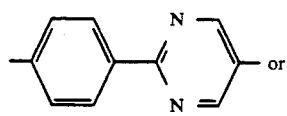 or

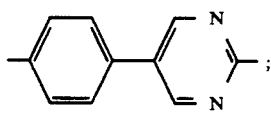

Y is —O—, —COO— or —OCO—; X is —COO— when n is 0 and —COO— or —OCO— when n is an integer of 1–5; and * mark denotes an asymmetric carbon atom.

2. The optically active aromatic compounds having a trifluoromethyl group according to claim 1, wherein X is —COO—.

3. The optically active aromatic compounds having a trifluoromethyl group according to claim 1, wherein X is —COO— and n is an integer of 1–5.

4. The optically active aromatic compounds having a trifluoromethyl group according to claim 1, wherein X is —COO—, n is 0, and Ar is

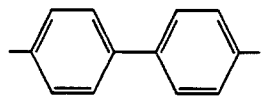

or

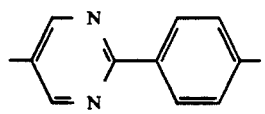

5. Liquid crystal-compositions containing at least one of the optically active aromatic compounds having a trifluoromethyl group according to claim 1 as an essential component.

6. Liquid crystal elements using the liquid crystal compositions containing at least one of the optically active aromatic compounds having a trifluoromethyl group according to claim 1 as an essential component.

7. Optically active benzoic acid derivatives represented by the following formula:

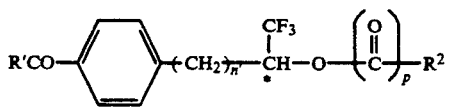

wherein $R^2$ is alkyl or alkoxyalkyl having 1–20 carbon atoms which may be substituted with halogen, R' is hydroxyl or halogen, p is a number of 0 or 1, * mark denotes an asymmetric carbon atom and n' is an integer of 1–5.

8. Optically active phenol derivatives represented by the following formula:

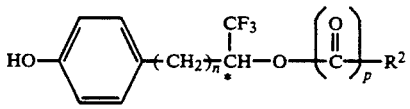

wherein $R^2$ is alkyl or alkoxyalkyl having 1–20 carbon atoms which may be substituted with halogen, n is an integer of 0–5, p is a number of 0 or 1, and * mark denotes an asymmetric carbon atom.

* * * * *